(12) United States Patent
Jovanovich et al.

(10) Patent No.: US 8,557,518 B2
(45) Date of Patent: Oct. 15, 2013

(54) MICROFLUIDIC AND NANOFLUIDIC DEVICES, SYSTEMS, AND APPLICATIONS

(75) Inventors: Stevan Bogdan Jovanovich, Livermore, CA (US); Iuliu I. Blaga, Fremont, CA (US); Michael Nguyen, San Jose, CA (US); William D. Nielsen, San Jose, CA (US); Mattias Vangbo, Fremont, CA (US)

(73) Assignee: IntegenX Inc., Pleasanton, CA (US)

( * ) Notice: Subject to any disclaimer, the term of this patent is extended or adjusted under 35 U.S.C. 154(b) by 109 days.

(21) Appl. No.: 12/845,650

(22) Filed: Jul. 28, 2010

(65) Prior Publication Data
US 2012/0115189 A1    May 10, 2012

Related U.S. Application Data

(63) Continuation of application No. 12/526,015, filed as application No. PCT/US2008/053099 on Feb. 5, 2008.

(60) Provisional application No. 60/899,630, filed on Feb. 5, 2007.

(51) Int. Cl.
  *C12Q 1/68* (2006.01)
  *C12P 19/34* (2006.01)
  *C12M 1/36* (2006.01)
  *B01L 3/00* (2006.01)

(52) U.S. Cl.
  USPC ... 435/6.1; 435/91.21; 435/283.1; 435/287.3; 435/288.5; 422/68.1; 422/502

(58) Field of Classification Search
  USPC ............ 435/6.1, 91.2, 283.1, 287.3, 288.5; 422/68.1, 502
  See application file for complete search history.

(56) References Cited

U.S. PATENT DOCUMENTS

| 3,190,310 A | 6/1965 | Honsinger |
| 3,352,643 A | 11/1967 | Ando et al. |

(Continued)

FOREIGN PATENT DOCUMENTS

| CA | 2433145 A1 | 5/2002 |
| EP | 0459241 B1 | 12/1991 |

(Continued)

OTHER PUBLICATIONS

Shaikh et al "A modular microfluidic archetecture for integrated biochemical analysis", PNAS, 2005, 102: 9745-9750.*

(Continued)

*Primary Examiner* — Betty Forman

(57) ABSTRACT

The present invention discloses the integration of programmable microfluidic circuits to achieve practical applications to process biochemical and chemical reactions and to integrate these reactions. In some embodiments workflows for biochemical reactions or chemical workflows are combined. Microvalves such as programmable microfluidic circuit with Y valves and flow through valves are disclosed. In some embodiments microvalves of the present invention are used for mixing fluids, which may be part of an integrated process. These processes include mixing samples and moving reactions to an edge or reservoir for modular microfluidics, use of capture regions, and injection into analytical devices on separate devices. In some embodiments star and nested star designs, or bead capture by change of cross sectional area of a channel in a microvalve are used. Movement of samples between temperature zones are further disclosed using fixed temperature and movement of the samples by micropumps.

11 Claims, 64 Drawing Sheets

Compact Integrated design.

(56) References Cited

U.S. PATENT DOCUMENTS

| | | |
|---|---|---|
| 3,433,257 A | 3/1969 | Jensen |
| 3,568,692 A | 3/1971 | Metzger et al. |
| 3,610,274 A | 10/1971 | Levesque et al. |
| 4,113,665 A | 9/1978 | Law et al. |
| 4,558,845 A | 12/1985 | Hunkapiller |
| 4,703,913 A | 11/1987 | Hunkapiller |
| 4,847,120 A | 7/1989 | Gent |
| 4,963,498 A | 10/1990 | Hillman et al. |
| 5,085,757 A | 2/1992 | Karger et al. |
| 5,275,645 A | 1/1994 | Ternoir et al. |
| 5,364,759 A | 11/1994 | Caskey et al. |
| 5,376,252 A | 12/1994 | Ekström et al. |
| 5,387,505 A | 2/1995 | Wu |
| 5,453,163 A | 9/1995 | Yan |
| 5,482,836 A | 1/1996 | Cantor et al. |
| 5,523,231 A | 6/1996 | Reeve |
| 5,571,410 A | 11/1996 | Swedberg et al. |
| 5,587,128 A | 12/1996 | Wilding et al. |
| 5,635,358 A | 6/1997 | Wilding et al. |
| 5,639,428 A | 6/1997 | Cottingham |
| 5,681,946 A | 10/1997 | Reeve |
| 5,705,628 A | 1/1998 | Hawkins |
| 5,705,813 A | 1/1998 | Apffel et al. |
| 5,726,026 A | 3/1998 | Wilding et al. |
| 5,741,462 A | 4/1998 | Nova et al. |
| 5,750,015 A | 5/1998 | Soane et al. |
| 5,770,029 A | 6/1998 | Nelson et al. |
| 5,775,371 A | 7/1998 | Pan et al. |
| 5,776,748 A | 7/1998 | Singhvi et al. |
| 5,830,662 A | 11/1998 | Soares et al. |
| 5,842,787 A | 12/1998 | Kopf-sill et al. |
| 5,856,174 A | 1/1999 | Lipshutz et al. |
| 5,863,502 A | 1/1999 | Southgate et al. |
| 5,872,010 A | 2/1999 | Karger et al. |
| 5,885,470 A | 3/1999 | Parce et al. |
| 5,898,071 A | 4/1999 | Hawkins |
| 5,900,130 A | 5/1999 | Benvegnu |
| 5,908,552 A | 6/1999 | Zimmermann et al. |
| 5,922,591 A | 7/1999 | Anderson et al. |
| 5,942,443 A | 8/1999 | Parce et al. |
| 5,948,684 A | 9/1999 | Weigl et al. |
| 5,971,158 A | 10/1999 | Yager et al. |
| 5,994,064 A | 11/1999 | Staub et al. |
| 6,001,229 A | 12/1999 | Ramsey |
| 6,007,690 A | 12/1999 | Nelson et al. |
| 6,007,775 A | 12/1999 | Yager |
| 6,010,607 A | 1/2000 | Ramsey |
| 6,048,100 A | 4/2000 | Thrall et al. |
| 6,056,860 A | 5/2000 | Amigo et al. |
| 6,073,482 A | 6/2000 | Moles |
| 6,074,827 A | 6/2000 | Nelson et al. |
| 6,103,199 A | 8/2000 | Bjornson et al. |
| 6,110,343 A | 8/2000 | Ramsey et al. |
| 6,120,184 A | 9/2000 | Laurence et al. |
| 6,136,212 A | 10/2000 | Mastrangelo et al. |
| 6,168,948 B1 | 1/2001 | Anderson et al. |
| 6,176,962 B1 | 1/2001 | Soane et al. |
| 6,190,616 B1 | 2/2001 | Jovanovich et al. |
| 6,197,595 B1 | 3/2001 | Anderson et al. |
| 6,207,031 B1 | 3/2001 | Adourian et al. |
| 6,235,471 B1 | 5/2001 | Knapp et al. |
| 6,238,538 B1 | 5/2001 | Parce et al. |
| 6,251,343 B1 | 6/2001 | Dubrow et al. |
| 6,280,589 B1 | 8/2001 | Manz et al. |
| 6,319,476 B1 | 11/2001 | Victor, Jr. et al. |
| 6,321,791 B1 | 11/2001 | Chow |
| 6,322,683 B1 | 11/2001 | Wolk et al. |
| 6,342,142 B1 | 1/2002 | Ramsey |
| 6,348,318 B1 | 2/2002 | Valkirs |
| 6,379,929 B1 | 4/2002 | Burns et al. |
| 6,387,234 B1 | 5/2002 | Yeung et al. |
| 6,387,707 B1 | 5/2002 | Seul et al. |
| 6,403,338 B1 | 6/2002 | Knapp et al. |
| 6,408,878 B2 | 6/2002 | Unger et al. |
| 6,423,536 B1 | 7/2002 | Jovanovich et al. |
| 6,429,025 B1 | 8/2002 | Parce et al. |
| 6,432,191 B2 | 8/2002 | Schutt |
| 6,432,290 B1 | 8/2002 | Harrison et al. |
| 6,454,924 B2 | 9/2002 | Jedrzejewski et al. |
| 6,489,112 B1 | 12/2002 | Hadd et al. |
| 6,521,188 B1 | 2/2003 | Webster |
| 6,524,456 B1 | 2/2003 | Ramsey et al. |
| 6,527,003 B1 | 3/2003 | Webster |
| 6,531,041 B1 | 3/2003 | Cong et al. |
| 6,531,282 B1 | 3/2003 | Dau et al. |
| 6,532,997 B1 | 3/2003 | Bedingham et al. |
| 6,533,914 B1 | 3/2003 | Liu |
| 6,534,262 B1 | 3/2003 | Mckernan et al. |
| 6,537,757 B1 | 3/2003 | Langmore et al. |
| 6,544,734 B1 | 4/2003 | Briscoe et al. |
| 6,551,839 B2 | 4/2003 | Jovanovich et al. |
| 6,581,441 B1 | 6/2003 | Paul |
| 6,581,899 B2 | 6/2003 | Williams |
| 6,605,454 B2 | 8/2003 | Barenburg et al. |
| 6,613,525 B2 | 9/2003 | Nelson et al. |
| 6,614,228 B2 | 9/2003 | Hofmann et al. |
| 6,618,679 B2 | 9/2003 | Loehrlein |
| 6,623,613 B1 | 9/2003 | Mathies et al. |
| 6,627,446 B1 | 9/2003 | Roach et al. |
| 6,629,820 B2 | 10/2003 | Kornelsen |
| 6,632,619 B1 | 10/2003 | Harrison et al. |
| 6,632,655 B1 | 10/2003 | Mehta et al. |
| 6,663,833 B1 | 12/2003 | Stave et al. |
| 6,685,442 B2 | 2/2004 | Chinn et al. |
| 6,685,809 B1 | 2/2004 | Jacobson et al. |
| 6,705,345 B1 | 3/2004 | Bifano |
| 6,752,922 B2 | 6/2004 | Huang et al. |
| 6,764,648 B1 | 7/2004 | Roach et al. |
| 6,782,746 B1 | 8/2004 | Hasselbrink et al. |
| 6,786,708 B2 | 9/2004 | Brown et al. |
| 6,787,111 B2 | 9/2004 | Roach et al. |
| 6,793,753 B2 | 9/2004 | Unger et al. |
| 6,802,342 B2 | 10/2004 | Fernandes et al. |
| 6,803,019 B1 | 10/2004 | Bjornson et al. |
| 6,807,490 B1 | 10/2004 | Perlin |
| 6,824,663 B1 | 11/2004 | Boone |
| 6,829,753 B2 | 12/2004 | Lee et al. |
| 6,833,246 B2 | 12/2004 | Balasubramanian |
| 6,852,287 B2 | 2/2005 | Ganesan |
| 6,870,185 B2 | 3/2005 | Roach et al. |
| 6,885,982 B2 | 4/2005 | Harris et al. |
| 6,899,137 B2 | 5/2005 | Unger et al. |
| 6,923,907 B2 | 8/2005 | Hobbs et al. |
| 6,929,030 B2 | 8/2005 | Unger et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 6,994,986 B2 | 2/2006 | Swartz et al. |
| 7,005,292 B2 | 2/2006 | Wilding et al. |
| 7,005,493 B2 | 2/2006 | Huang et al. |
| 7,015,030 B1 | 3/2006 | Fouillet et al. |
| 7,046,357 B2 | 5/2006 | Weinberger et al. |
| 7,049,558 B2 | 5/2006 | Baer et al. |
| 7,063,304 B2 | 6/2006 | Leys |
| 7,087,380 B2 | 8/2006 | Griffiths et al. |
| 7,097,809 B2 | 8/2006 | Van Dam et al. |
| 7,118,910 B2 | 10/2006 | Unger et al. |
| 7,157,228 B2 | 1/2007 | Hashmi et al. |
| 7,169,557 B2 | 1/2007 | Rosenblum et al. |
| 7,198,759 B2 | 4/2007 | Bryning et al. |
| 7,211,388 B2 | 5/2007 | Cash et al |
| 7,217,367 B2 | 5/2007 | Huang et al. |
| 7,232,656 B2 | 6/2007 | Balasubramanian et al. |
| 7,244,961 B2 | 7/2007 | Jovanovich et al. |
| 7,258,774 B2 | 8/2007 | Chou et al. |
| 7,279,146 B2 | 10/2007 | Nassef et al. |
| 7,282,361 B2 | 10/2007 | Hodge |
| 7,312,085 B2 | 12/2007 | Chou et al. |
| 7,312,611 B1 | 12/2007 | Harrison et al. |
| 7,323,305 B2 | 1/2008 | Leamon et al. |
| 7,361,471 B2 | 4/2008 | Gerdes et al. |
| 7,377,483 B2 | 5/2008 | Iwabuchi et al. |
| 7,416,165 B2 | 8/2008 | Ohmi et al. |
| 7,438,856 B2 | 10/2008 | Jedrzejewski et al. |

(56) References Cited

U.S. PATENT DOCUMENTS

| | | |
|---|---|---|
| 7,445,926 B2 | 11/2008 | Mathies et al. |
| 7,488,603 B2 | 2/2009 | Gjerde et al. |
| 7,501,237 B2 | 3/2009 | Solus et al. |
| 7,526,741 B2 | 4/2009 | Lee et al. |
| 7,537,886 B1 | 5/2009 | Nazarenko et al. |
| 7,575,865 B2 | 8/2009 | Leamon et al. |
| 7,645,580 B2 | 1/2010 | Barber et al. |
| 7,691,614 B2 | 4/2010 | Senapathy |
| 7,745,207 B2 | 6/2010 | Jovanovich et al. |
| 7,763,453 B2 | 7/2010 | Clemmens et al. |
| 7,766,033 B2 | 8/2010 | Mathies et al. |
| 7,790,368 B1 | 9/2010 | Fukuzono |
| 7,799,553 B2 | 9/2010 | Mathies et al. |
| 7,803,281 B2 | 9/2010 | Davies |
| 7,817,273 B2 | 10/2010 | Bahatt et al. |
| 7,832,429 B2 | 11/2010 | Young et al. |
| 7,863,357 B2 | 1/2011 | Madabhushi et al. |
| 7,867,713 B2 | 1/2011 | Nasarabadi |
| 7,885,770 B2 | 2/2011 | Gill et al. |
| 7,892,856 B2 | 2/2011 | Grate et al. |
| 7,942,160 B2 | 5/2011 | Jeon et al. |
| 7,943,305 B2 | 5/2011 | Korlach et al. |
| 7,959,875 B2 | 6/2011 | Zhou et al. |
| 7,972,561 B2 | 7/2011 | Viovy et al. |
| 7,976,789 B2 | 7/2011 | Kenis et al. |
| 7,976,795 B2 | 7/2011 | Zhou et al. |
| 8,007,746 B2 | 8/2011 | Unger et al. |
| 8,018,593 B2 | 9/2011 | Tan et al. |
| 8,037,903 B2 | 10/2011 | Wang et al. |
| 8,053,192 B2 | 11/2011 | Bignell et al. |
| 2001/0041357 A1 | 11/2001 | Fouillet et al. |
| 2002/0022587 A1 | 2/2002 | Ferguson et al. |
| 2002/0025529 A1 | 2/2002 | Quake et al. |
| 2002/0025576 A1 | 2/2002 | Northrup et al. |
| 2002/0047003 A1 | 4/2002 | Bedingham et al. |
| 2002/0048536 A1 | 4/2002 | Bergh et al. |
| 2002/0058332 A1 | 5/2002 | Quake et al. |
| 2002/0068357 A1 | 6/2002 | Mathies et al. |
| 2002/0098097 A1 | 7/2002 | Singh |
| 2002/0110900 A1 | 8/2002 | Jovanovich et al. |
| 2002/0119480 A1 | 8/2002 | Weir et al. |
| 2002/0119482 A1 | 8/2002 | Nelson et al. |
| 2002/0127736 A1 | 9/2002 | Chou et al. |
| 2002/0139084 A1 | 10/2002 | Tobolka |
| 2002/0144738 A1 | 10/2002 | Unger et al. |
| 2002/0148992 A1 | 10/2002 | Hayenga et al. |
| 2002/0157951 A1 | 10/2002 | Foret et al. |
| 2002/0160361 A1 | 10/2002 | Loehrlein et al. |
| 2003/0008308 A1 | 1/2003 | Enzelberger et al. |
| 2003/0021734 A1 | 1/2003 | Vann et al. |
| 2003/0029724 A1 | 2/2003 | Derand et al. |
| 2003/0070677 A1 | 4/2003 | Handique et al. |
| 2003/0077839 A1 | 4/2003 | Takei |
| 2003/0095897 A1 | 5/2003 | Grate et al. |
| 2003/0217923 A1 | 11/2003 | Harrison et al. |
| 2004/0003997 A1 | 1/2004 | Anazawa et al. |
| 2004/0013536 A1 | 1/2004 | Hower et al. |
| 2004/0014091 A1 | 1/2004 | Duck et al. |
| 2004/0018611 A1 | 1/2004 | Ward et al. |
| 2004/0021068 A1 | 2/2004 | Staats |
| 2004/0037739 A1 | 2/2004 | Mcneely et al. |
| 2004/0038385 A1 | 2/2004 | Langlois et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0086870 A1 | 5/2004 | Tyvoll et al. |
| 2004/0086872 A1 | 5/2004 | Childers et al. |
| 2004/0151629 A1 | 8/2004 | Pease et al. |
| 2004/0185484 A1 | 9/2004 | Costa et al. |
| 2004/0197845 A1 | 10/2004 | Hassibi et al. |
| 2004/0200724 A1 | 10/2004 | Fujii et al. |
| 2004/0209354 A1 | 10/2004 | Mathies et al. |
| 2004/0224380 A1 | 11/2004 | Chou et al. |
| 2005/0026300 A1 | 2/2005 | Samper et al. |
| 2005/0047967 A1 | 3/2005 | Chuang et al. |
| 2005/0053952 A1 | 3/2005 | Hong et al. |
| 2005/0142663 A1 | 6/2005 | Parthasarathy et al. |
| 2005/0161326 A1 | 7/2005 | Morita et al. |
| 2005/0161669 A1 | 7/2005 | Jovanovich et al. |
| 2005/0221373 A1 | 10/2005 | Enzelberger et al. |
| 2005/0224352 A1 | 10/2005 | Harrison et al. |
| 2005/0241941 A1 | 11/2005 | Parce et al. |
| 2005/0250199 A1 | 11/2005 | Anderson et al. |
| 2005/0255000 A1 | 11/2005 | Yamamoto et al. |
| 2005/0255003 A1 | 11/2005 | Summersgill et al. |
| 2005/0255007 A1 | 11/2005 | Yamada et al. |
| 2005/0266582 A1 | 12/2005 | Modlin et al. |
| 2005/0287572 A1 | 12/2005 | Mathies et al. |
| 2006/0027456 A1 | 2/2006 | Harrison et al. |
| 2006/0057209 A1 | 3/2006 | Chapman et al. |
| 2006/0073484 A1 | 4/2006 | Mathies et al. |
| 2006/0076068 A1 | 4/2006 | Young et al. |
| 2006/0140051 A1 | 6/2006 | Kim et al. |
| 2006/0163143 A1 | 7/2006 | Chirica et al. |
| 2006/0177832 A1 | 8/2006 | Brenner |
| 2006/0186043 A1 | 8/2006 | Covey et al. |
| 2006/0210998 A1 | 9/2006 | Kettlitz et al. |
| 2006/0260941 A1 | 11/2006 | Tan et al. |
| 2006/0263789 A1 | 11/2006 | Kincaid |
| 2006/0266645 A1 | 11/2006 | Chen et al. |
| 2006/0292032 A1 | 12/2006 | Hataoka et al. |
| 2007/0015179 A1 | 1/2007 | Klapperich et al. |
| 2007/0017812 A1 | 1/2007 | Bousse |
| 2007/0020654 A1 | 1/2007 | Blume et al. |
| 2007/0031865 A1 | 2/2007 | Willoughby |
| 2007/0034025 A1 | 2/2007 | Pant et al. |
| 2007/0105163 A1 | 5/2007 | Grate et al. |
| 2007/0113908 A1 | 5/2007 | Lee et al. |
| 2007/0122819 A1 | 5/2007 | Wu et al. |
| 2007/0175756 A1 | 8/2007 | Nguyen et al. |
| 2007/0184463 A1 | 8/2007 | Molho et al. |
| 2007/0202531 A1 | 8/2007 | Grover |
| 2007/0237686 A1 | 10/2007 | Mathies et al. |
| 2007/0238109 A1 | 10/2007 | Min et al. |
| 2007/0248958 A1 | 10/2007 | Jovanovich et al. |
| 2007/0289941 A1 | 12/2007 | Davies |
| 2007/0297947 A1 | 12/2007 | Sommers et al. |
| 2008/0014576 A1 | 1/2008 | Jovanovich et al. |
| 2008/0014589 A1 | 1/2008 | Link et al. |
| 2008/0047836 A1 | 2/2008 | Strand et al. |
| 2008/0064610 A1 | 3/2008 | Lipovsek et al. |
| 2008/0124723 A1 | 5/2008 | Dale et al. |
| 2008/0138809 A1 | 6/2008 | Kapur et al. |
| 2008/0164155 A1 | 7/2008 | Pease et al. |
| 2008/0179255 A1 | 7/2008 | Jung et al. |
| 2008/0179555 A1 | 7/2008 | Landers et al. |
| 2008/0237146 A1 | 10/2008 | Harrison et al. |
| 2008/0242560 A1 | 10/2008 | Gunderson et al. |
| 2008/0257437 A1 | 10/2008 | Fernandes et al. |
| 2008/0281090 A1 | 11/2008 | Lee et al. |
| 2008/0302732 A1 | 12/2008 | Soh et al. |
| 2008/0311585 A1 | 12/2008 | Gao et al. |
| 2009/0004494 A1 | 1/2009 | Blenke et al. |
| 2009/0011959 A1 | 1/2009 | Costa et al. |
| 2009/0023603 A1 | 1/2009 | Selden et al. |
| 2009/0035770 A1 | 2/2009 | Mathies et al. |
| 2009/0053799 A1 | 2/2009 | Chang-yen et al. |
| 2009/0056822 A1 | 3/2009 | Young et al. |
| 2009/0060797 A1 | 3/2009 | Mathies et al. |
| 2009/0084679 A1 | 4/2009 | Harrison et al. |
| 2009/0092970 A1 | 4/2009 | Williams |
| 2009/0134069 A1 | 5/2009 | Handique |
| 2009/0137413 A1 | 5/2009 | Mehta et al. |
| 2009/0148933 A1 | 6/2009 | Battrell et al. |
| 2009/0178934 A1 | 7/2009 | Jarvius et al. |
| 2009/0181411 A1 | 7/2009 | Battrell et al. |
| 2009/0253181 A1 | 10/2009 | Vangbo et al. |
| 2009/0269504 A1 | 10/2009 | Liao |
| 2009/0286327 A1 | 11/2009 | Cho et al. |
| 2009/0311804 A1 | 12/2009 | Mcbrady et al. |
| 2009/0314972 A1 | 12/2009 | Mcavoy et al. |
| 2009/0325277 A1 | 12/2009 | Shigeura et al. |
| 2010/0068723 A1 | 3/2010 | Jovanovich et al. |
| 2010/0111770 A1 | 5/2010 | Hwang et al. |

(56) References Cited

U.S. PATENT DOCUMENTS

| | | | |
|---|---|---|---|
| 2010/0129810 A1 | 5/2010 | Greiner et al. |
| 2010/0165784 A1 | 7/2010 | Jovanovich et al. |
| 2010/0172898 A1 | 7/2010 | Doyle et al. |
| 2010/0173398 A1 | 7/2010 | Peterman |
| 2010/0197507 A1 | 8/2010 | Rothberg et al. |
| 2010/0210008 A1 | 8/2010 | Strand et al. |
| 2010/0221726 A1 | 9/2010 | Zenhausern et al. |
| 2010/0224255 A1 | 9/2010 | Mathies et al. |
| 2010/0228513 A1 | 9/2010 | Roth et al. |
| 2010/0233696 A1 | 9/2010 | Joseph et al. |
| 2010/0243916 A1 | 9/2010 | Maurer et al. |
| 2010/0252123 A1 | 10/2010 | Mathies et al. |
| 2010/0266432 A1 | 10/2010 | Pirk et al. |
| 2010/0285578 A1 | 11/2010 | Selden et al. |
| 2010/0285606 A1 | 11/2010 | Phillips et al. |
| 2010/0285975 A1 | 11/2010 | Mathies et al. |
| 2010/0291666 A1 | 11/2010 | Collier et al. |
| 2010/0303687 A1 | 12/2010 | Blaga et al. |
| 2010/0304355 A1 | 12/2010 | Shuler et al. |
| 2010/0326826 A1 | 12/2010 | Harrison et al. |
| 2011/0003301 A1 | 1/2011 | Raymond et al. |
| 2011/0005932 A1 | 1/2011 | Jovanovich et al. |
| 2011/0008813 A1 | 1/2011 | Dilleen et al. |
| 2011/0020920 A1 | 1/2011 | Mathies et al. |
| 2011/0027913 A1 | 2/2011 | Bau et al. |
| 2011/0038758 A1 | 2/2011 | Akaba et al. |
| 2011/0039303 A1 | 2/2011 | Jovanovich et al. |
| 2011/0045505 A1 | 2/2011 | Warthoe et al. |
| 2011/0048945 A1 | 3/2011 | Harrison et al. |
| 2011/0053784 A1 | 3/2011 | Unger et al. |
| 2011/0070578 A1 | 3/2011 | Bell et al. |
| 2011/0076735 A1 | 3/2011 | Jovanovich et al. |
| 2011/0124049 A1 | 5/2011 | Li et al. |
| 2011/0126910 A1 | 6/2011 | May |
| 2011/0127222 A1 | 6/2011 | Chang-yen et al. |
| 2011/0136179 A1 | 6/2011 | Bin/lee et al. |
| 2011/0137018 A1 | 6/2011 | Chang-yen et al. |
| 2011/0171086 A1 | 7/2011 | Prins et al. |
| 2011/0172403 A1 | 7/2011 | Harrold et al. |
| 2011/0189678 A1 | 8/2011 | Mcbride et al. |
| 2011/0206576 A1 | 8/2011 | Woudenberg et al. |
| 2011/0212440 A1 | 9/2011 | Viovy et al. |
| 2011/0212446 A1 | 9/2011 | Wang et al. |
| 2011/0223605 A1 | 9/2011 | Bienvenue et al. |

FOREIGN PATENT DOCUMENTS

| | | |
|---|---|---|
| EP | 0637999 A1 | 2/1995 |
| EP | 0527905 B1 | 11/1995 |
| EP | 1065378 B1 | 4/2002 |
| EP | 1411340 A2 | 4/2004 |
| EP | 1411340 A3 | 5/2004 |
| EP | 1345697 B1 | 6/2007 |
| EP | 1658890 B1 | 5/2008 |
| EP | 1345551 B1 | 4/2009 |
| EP | 2345739 A2 | 7/2011 |
| JP | 2007-506430 A | 7/1995 |
| JP | 408327594 A | 12/1996 |
| JP | 2001-500966 A | 1/2001 |
| JP | 2001-521818 A | 11/2001 |
| JP | 2002-370200 A | 12/2002 |
| JP | 2003-536058 A | 12/2003 |
| JP | 2004-025159 A | 1/2004 |
| JP | 2004-108285 A | 4/2004 |
| JP | 2004-180594 A | 7/2004 |
| JP | 2005-323519 A | 11/2005 |
| JP | 2005-337415 | 12/2005 |
| JP | 2005-345463 A | 12/2005 |
| JP | 2007-155491 A | 6/2007 |
| JP | 2008-513022 A | 5/2008 |
| WO | WO 93/22053 A1 | 4/1993 |
| WO | WO 96/04547 A1 | 2/1996 |
| WO | WO 96/14934 A1 | 5/1996 |
| WO | WO 98/10277 A1 | 7/1997 |
| WO | WO 99/22868 A1 | 10/1998 |
| WO | WO 98/52691 A1 | 11/1998 |
| WO | WO 98/53300 A2 | 11/1998 |
| WO | WO 98/53300 A3 | 2/1999 |
| WO | WO 99/36766 A1 | 7/1999 |
| WO | WO 99/40174 A1 | 8/1999 |
| WO | WO 00/40712 A1 | 7/2000 |
| WO | WO 00/60362 A1 | 10/2000 |
| WO | WO 00/61198 | 10/2000 |
| WO | WO 01/32930 A1 | 5/2001 |
| WO | WO 01/38865 A1 | 5/2001 |
| WO | WO 01/85341 A1 | 11/2001 |
| WO | WO 02/43864 A2 | 11/2001 |
| WO | WO 02/24949 A1 | 3/2002 |
| WO | WO 02/41995 A1 | 5/2002 |
| WO | WO 02/43615 A2 | 6/2002 |
| WO | WO 02/043864 A3 | 8/2002 |
| WO | WO 02/043615 A3 | 3/2003 |
| WO | WO 03/044528 A2 | 5/2003 |
| WO | WO 03/085379 | 10/2003 |
| WO | WO 2004/038363 A2 | 5/2004 |
| WO | WO 03/044528 A3 | 6/2004 |
| WO | WO 2004/061085 A2 | 7/2004 |
| WO | WO 2004/061085 A3 | 10/2004 |
| WO | WO 2004/098757 A2 | 11/2004 |
| WO | WO 2004/038363 A3 | 12/2004 |
| WO | WO 2005/075081 A1 | 8/2005 |
| WO | WO 2005/091820 A2 | 10/2005 |
| WO | WO 2005/108620 A2 | 11/2005 |
| WO | WO 2005/118867 A2 | 12/2005 |
| WO | WO 2005/121308 A1 | 12/2005 |
| WO | WO 2006/032044 A2 | 3/2006 |
| WO | WO 2005/108620 A3 | 4/2006 |
| WO | WO 2004/098757 A3 | 5/2006 |
| WO | WO 2005/091820 A3 | 10/2006 |
| WO | WO 2006/032044 A3 | 1/2007 |
| WO | WO 2007/002579 A2 | 1/2007 |
| WO | WO 2007/064635 A1 | 6/2007 |
| WO | WO 2007/082480 A1 | 7/2007 |
| WO | WO 2007/109375 A2 | 9/2007 |
| WO | WO 2005/118867 A3 | 12/2007 |
| WO | WO 2008/012104 A2 | 1/2008 |
| WO | WO 2008/024319 A2 | 2/2008 |
| WO | WO 2008/024319 A3 | 4/2008 |
| WO | WO 2008/039875 A1 | 4/2008 |
| WO | WO 2008/012104 A3 | 5/2008 |
| WO | WO 2008/115626 A2 | 9/2008 |
| WO | WO 2007/109375 A3 | 10/2008 |
| WO | WO 2008/115626 A3 | 11/2008 |
| WO | WO 2009/008236 A1 | 1/2009 |
| WO | WO 2009/015296 A1 | 1/2009 |
| WO | WO 2007/002579 A3 | 9/2009 |
| WO | WO 2009/108260 A2 | 9/2009 |
| WO | WO 2009/129415 A1 | 10/2009 |
| WO | WO 2009/108260 A3 | 12/2009 |
| WO | WO 2010/041174 A1 | 4/2010 |
| WO | WO 2010/041231 A2 | 4/2010 |
| WO | WO 2010/042784 A2 | 4/2010 |
| WO | WO 2010/042784 A3 | 7/2010 |
| WO | WO 2010/041231 A3 | 9/2010 |
| WO | WO 2010/109392 A1 | 9/2010 |
| WO | WO 2010/130762 A2 | 11/2010 |
| WO | WO 2010/141921 A1 | 12/2010 |
| WO | WO 2011/003941 A1 | 1/2011 |
| WO | WO 2010/130762 A3 | 2/2011 |
| WO | WO 2011/012621 A1 | 2/2011 |
| WO | WO 2011/034621 A2 | 3/2011 |
| WO | WO 2011/084703 A2 | 7/2011 |
| WO | WO 2011/034621 A3 | 11/2011 |

OTHER PUBLICATIONS

Fuentes et al "Detecting minimal traces of DNA using DNA covalently attached to superparamagnetic nanoparticles and direct PCR-ELISA" Biosensors and Bioelectronics Aug. 29, 2005, 21: 1574-1580.*

U.S. Appl. No. 13/202,877, filed Aug. 23, 2011, Vangbo et al.

U.S. Appl. No. 13/202,884, filed Aug. 23, 2011, Jovanovich et al.

(56) References Cited

OTHER PUBLICATIONS

Bennett, et al. Toward the 1,000 dollars human genome. Pharmacogenomics, 6 (4) 373-382. (Jun. 2005).
Chinese office action dated Jan. 31, 2011 for CN 200580035911.7. (In Chinese with English translation).
Erratum for Margulies, et al. Genome sequencing in microfabricated high-density picolitre reactors. Nature. 2005;437(7057):376-80.: Margulies, et al. Nature. 441(7089):120. (May 4, 2006).
International search report dated Sep. 1, 2010 for PCT/US2010/040490.
U.S. Appl. No. 90/011,453, filed Jan. 21, 2011, Mathias et al.
European search report and search opinion dated Aug. 17, 2011 for Application No. 08799648.4.
Notice of allowance dated Sep. 8, 2011 for U.S. Appl. No. 12/820,390.
U.S. Appl. No. 13/349,832, filed Jan. 13, 2012, Eberhart et al.
U.S. Appl. No. 13/367,326, filed Feb. 6, 2012, Jovanovich et al.
U.S. Appl. No. 13/384,753, filed Jan. 18, 2012, Stern et al.
Allowed Claims dated May 6, 2010 for U.S. Appl. No. 11/726,701.
Allowed Claims dated Jul. 1, 2010 for U.S. Appl. No. 11/139,018.
Allowed Claims dated Aug. 13, 2008 for U.S. Appl. No. 10/750,533.
Auroux, et al. Micro Total Analysis Systems 2. Analytical Standard Operations and Applications. Anal. Chem. 2002; 2637-2652.
Belgrader, et al. A Minisonicator to Rapidly Disrupt Bacterial Spores for DNA Analysis. Anal. Che. 1999; 4232-4236.
Belgrader, et al. PCR Detection of Bacteria in Seven Minutes. Science Magazin. 1999; 284(5413):449-450.
Belgrader, et al. Rapid PCR for Identity Testing Using a Battery-Powered Miniature Thermal Cycler. J Forensic Sci. 1998; 315-319.
Birnboim. A Rapid Alkaline Extraction Method for the Isolation of Plasmid DNA. Methods of Enzymology. 1983; 100:243-255.
Blazej, et al. Inline injection microdevice for attomole-scale sanger DNA sequencing. Anal Chem. Jun. 15, 2007;79(12):4499-506. Epub May 12, 2007.
Burns, et al. An Integrated Nanoliter DBA Analysis Device. Science Magazine. 1998; 484-487.
Call, et al. Detecting and genotyping *Escherichia coli* 0157:H7 using multiplexed PCR and nucleic acid microarrays. International Journal of Food Microbiology. 2001; 67:71-80.
Cameron, et al. High Internal Phase Emulsions (HIPEs) Structure, Properties and Use in Polymer Preparation. University of Strathclyde. 1995; 163214.
Canadian Office Action dated Jun. 10, 2011 for CA Application No. 2512071.
Capanu, et al. Design Fabrication and Testing of a Bistable Electromagnetically Actuated Microvalve. Journal of Microeclectromechanical System. 2000; 9:181-189.
Chandler, et al. Automated immunomagnetic separation and microarray detection of *E. coli* 0157:H7 from poultry carcass rinse. International Journal of Food Microbiology. 2001; 70:143-154.
Charlieu, et al. 3' Alu PCR: a simple and rapid method to isolate human polymorphic markers. Nucleic Acids Res. Mar. 25, 1992;20(6):1333-7.
Chinese office action dated Jan. 18, 2012 for CN 200980108368.7. (In Chinese with English translation).
Chinese Office Action dated Jan. 25, 2008 for Application No. 2003801100666.
Chinese office action dated Feb. 24, 2010 for CN Application No. 200780018073.1.
Delehanty, et al. A Microarray Immunoassay for Simultaneous Detection of Proteins and Bacteria. Anal. Chem. 2002; 74:5681-5687.
Dodson, et al. Fluidics Cube for Biosensor Miniaturization. Anal. Chem. 2001; 3776-3780.
Duffy, et al. Rapid Prototyping of Microfluidic Systems in Poly(dimethylsiloxane). Anal. Chem. 1998; 4974-4984.
European office action dated Apr. 7, 2011 for EP Application No. 05804847.1.

Gau, et al. A MEMS based amperometric detector for *E. coli* bacteria using self-assembled monolayers. Biosensors & Bioelectronic. 2001; 16:745755.
Hansen, et al. Polymerase chain reaction assay for the detection of *Bacillus cereus* group cells. FEMS Microbology Letters. 2001; 202:209-213.
Hartmann, et al. Direct immobilization of antibodies on phthalocyaninato-polysiloxane photopolymers. Thin Solid Films. 1994; 245:206-210.
Hartmann, et al. One-step immobilization of immunoglobulin G and potential of the method for application in immunosensors. Sensors and Actuators. 1995; 28 (2):143-149.
He, et al. Fabrication of Nanocolumns for Liquid Chromatography. Anal. Chem. 1998; 3790-3797.
Hjerten. High-performance electrophoresis : Elimination of electroendosmosis and solute adsorption. J. Chromotography. 1985; 347:191-198.
Hosokawa, et al. A Pneumatically-Actuated Three-Way Microvalve Fabricated with Polydimcthylsiloxanc Using the Membrane Transfer Technique. J. Micinicch. Microeng. 2000; 10:415-420.
International search report and written opinion dated Oct. 29, 2007 for PCT/US2005/018678.
International search report and written opinion dated Mar. 16, 2012 for PCT/US2011/048528.
International search report and written opinion dated Jul. 15, 2008 for PCT/US2007/007381.
Jacobson, et al. High-Speed Separations on a Microchip. Anal. Chem. 1994; 1114-1118.
Jacobson, et al. Integrated Microdevice for DNA Restriction Fragment Analysis Anal. Chem. 1996; 720-723.
Japanese office action dated Jan. 5, 2012 for Application No. 2007-532553 (in Japanese with English translation).
Japanese Office Action dated Jan. 13, 2010 for JP Application No. 2005508628.
Japanese office action dated Mar. 1, 2011 for JP Application. No. 2007-515379.
Japanese Office Action dated Aug. 10, 2010 for JP Application No. 2005508628.
Kamei, et al. Integrated Amorphous Silicon Photodiode Detector for Microfabricaqted Capillary Electrophoresis Devices. Micro Total Analysis Systems. 2002; 257-259.
Kamei, et al. Integrated hydrogenated amorphous Si photodiode detector for microfluidic bioanalytical devices. Anal Chem. Oct. 15, 2003;75(20):5300-5.
Kimura, et al. Restriction-Site-Specific PCR as a Rapid Test to Detect Enterohemorrhagic *Escherichia coli* 0157:H7 Strains in Environmental Samples. Applied and Environmental Microbiology. Jun. 2000; 25132519.
Koch, et al. Optical flow-cell multichannel immunosensor for the detection of biological warfare agents. Biosens Bioelectron. Jan. 2000;14(10-11):779-84.
Kong, et al. Rapid detection of six types of bacterial pathogens in marine waters by multiplex PCR. Water Research. 2002; 36: 2802-2812.
Korean office action dated Mar. 5, 2012 for KR 10-2007-7008423. (In Korean with English translation).
Kourentzi, et al. Microbial identification by immunohybridization assay of artificial RNA labels. Journal of Microbiological Methods. 2002; 49:301-306.
Kuhnert, et al. Detection System for *Escherichia coli*-Specific Virulence Genes: Absence of Virulence Determinants in B and C Strains. applied and Environmental Microbiology. 1997:703-709.
Ligler, et al. Integrating Waveguide Biosensor. Anal Chem. Feb. 1, 2002;74(3):713-9.
Manz, et al. Miniaturized Total Chemical Analysis Systems: A Novel Concept for Chemical Sensing. Sensors & Actuators. 1990; 244-248.
McLaughlin, et al. Molecular Approaches to the Identification of Streptococci. Methods in Molecular Medicine. 1998; 15:117-139.
Medintz, et al. Genotyping Energy-Transfer Cassette Labeled Short Tandem Repeat Amplicons with Capillary Array Electrophoresis Microchannel Plates. Clinical Chemistry. 2001; 1614-1621.

(56) References Cited

OTHER PUBLICATIONS

Medintz, et al. High-Performance Genetic Analysis Using Microfabricated Capillary Array Electroporesis Microplates. Electrophoresis. 2001; 38453856.
Medintz, et al. High-Performance Multiplex SNP Analysis of Three Hemochmromatosis-Related Mutations with Capillary Array Electrophoresis Microplates. Genome Research. 2001; 413-421.
Medintz, et al. Novel Energy Transfer Fluorescence Labeling Cassette. BioTechniques. 2002; 32(2):270.
Nataro, et al. Diarrheagenic *Escherichia coli*. Clinical MicroBiology Reviews. Jan. 1998;142-201.
Notice of Allowance dated May 6, 2010 for U.S. Appl. No. 11/726,701.
Notice of Allowance dated Jul. 1, 2010 for U.S. Appl. No. 11/139,018.
Notice of Allowance dated Aug. 13, 2008 for U.S. Appl. No. 10/750,533.
Office action dated Jan. 7, 2011 for U.S. Appl. No. 12/844,544.
Office action dated Jan. 20, 2010 for U.S. Appl. No. 11/978,224.
Office action dated Feb. 22, 2010 for U.S. Appl. No. 11/139,018.
Office action dated Mar. 2, 2008 for U.S. Appl. No. 10/540,658.
Office action dated Mar. 29, 2012 for U.S. Appl. No. 12/789,186.
Office action dated Mar. 30, 2012 for U.S. Appl. No. 12/795,515.
Office action dated Apr. 11, 2012 for U.S. Appl. No. 11/139,018.
Office action dated Apr. 29, 2009 for U.S. Appl. No. 11/139,018.
Office action dated Aug. 27, 2008 for U.S. Appl. No. 11/139,018.
Office action dated Oct. 8, 2008 for U.S. Appl. No. 10/540,658.
Office action dated Oct. 25, 2010 for U.S. Appl. No. 11/978,224.
Office action dated Nov. 6, 2009 for U.S. Appl. No. 11/139,018.
Office action dated Dec. 11, 2009 for U.S. Appl. No. 11/726,701.
O'Mahony, et al. A real time PCR assay for the detection and quantitation of *Mycobacterium avium* subsp. Paratuberculosis using SYBR Green and the Light Cycler. Journal of Microbiological Methods. 2002; 51:283-293.
Papadelli, et al. Rapid detection and identification of *Streptococcus macedonicus* by species-specific PCR and DNA hybridisation. International Journal of Food Microbiology. 2003; 81:231-239.
Peng, et al. Immuno-capture PCR for detection of *Aeromonas hydrophila* Journal of Microbiological Methods. 2002; 49:335-338.
Press, et al., An Integrated Microfluidic Processor for Single Nucleotide Polymorphism-based DNA Computing, Lab on a Chip. 2005, 5:10, 8 pages.
Press, et al., The Art of Scientific Computing, Numerical Recipes in C, 2nd Edition, Cambridge University Press, 1992, (table of Contents).
Quake, et al. From Micro-to Nanofabrication with Soft Materials. Science Magazine. 2000; 1536-1540.
Reyes, et al. Micro Total Analysis Systems. 1. Introduction Theory and Technology. Anal Chem. 2002; 2623-2636.
Roth, et al. Fundamentals of Logic Design, 3$^{rd}$ Edition, West Publishing Company, 1985 (Table of Content).
Rowe, et al. Array Biosensor for Simultaneous Identification of Bacterial, Viral and Protein Analytes. Anal. Chem. 1999; 71:3846-3852.
Rowe-Taitt, et al., Simultaneous detection of six biohazardous agents using a planar waveguide array biosensor. Biosensors & Bioelectronics. 2000; 15:579-589.
Ruan, et al. Immunobiosensor Chips for Detection of *Escherichia coli* 0157:H7 Using Electrochemical Impedance Spectroscopy. Anal. Chem. 2002; 74:4814-4820.
Sanford, et al. Photoactivatable Cross-Linked Polyacrylamide for the Site-Selective Immobilization of Antigens and Antibodies Chem Mater. 1998; 10(6): 15101520.
Shi, et al. Radial Capillary Array Electrophoresis Microplate and Scanner for High Performance Nucleic Acid Analysis. Anal. Chem. 1999; 5354-5361.
Soper, et al. Polymeric Microelectro-mechanical Systems. Anal. Chem 2000; 643-651.
Stumpfle, et al. Absence of DNA sequence homology with genes of the *Exchericia coli* hemB locus in Shiga-toxin producing *E. coli* (STEC) 0157 Strains. FEMS Microbiology Letters. 1999; 174:97-103.
Sun, et al. A Heater-Integrated Transparent Microchannel Chip for Continuous Flow PCR. Sensors and Actuators B. 2002; 84:283-289.
Tian, et al. Evaluation of Silica Resins for Direct and Efficient Extraction of DNA from Complex Biological Matrices in a Miniaturized Format. Analytical Biochemistry. 2000; 283:175-191.
Verlee, et al al. .Fluid Circuit Technology: Integrated Interconnect Technology for Miniature Fluidic Devices. Abbott Laboratories Hospital Division, Abbott Park, IL. 1996; 9-14.
Walt, et al. Biological Warefare Detection. Analytical Chemistry 2000; 739-746.
Waters, et al. Microchip Device for Cell Lysis, Multiplex PCR Amplification, and Electrophoretic Sizing Anal. Chem. 1999; 158-162.
Webster, et al. Monolithic Capillary Electrophoresis Device with Integrated Fluorescence Detector. Anal. Chem. 2001;1622-1626.
White, et al. Flash detection/identification of pathogens, bacterial spores and bioterrorism agent biomarker from clinical and environmental matrices. Journal of Microbiological Methods. 2002; 48:139-147.
Yacoub-George, et al. Chemiluminescence multichannel immunosensor for biodetection Analytica Chimica Acta. 2002; 457:3-12.
Yang, et al. An Integrated Stacked Microlaboratory for Biological Agent Detection with DNA and Immunoassays. Biosensors & Bioelectronics. 2002; 17:605-618.
Zhu, et al. High-Sensitivity Capillary Electrophoresis of Double-Stranded DNA Fragments Using Monomeric and Dimeric Fluorescent Intercalating Dyes. Anal Chem. 1994; 1941-1948.
Bianco, et al. Teflon-like coatings for micro devices. CPAC Satellite Workshops. Rome, Italy. Mar. 23, 2009.
Blaga, et al. Microfluidic device for automated sample preparation. Poster. MSB Conference. Dalian, China. Oct. 2009.
Blaga, et al. Plastic chips with valves and pumps. MSB Conference. Berlin, Germany. Mar. 2008. Abstract only.
Franklin, et al. Apollo 200: an integrated platform for DNA profiling. Poster. MCB Conference. Prague, Czech Republic. Mar. 2010.
International search report and written opinion dated Apr. 30, 2012 for PCT/US2012/021217.
Japanese office action dated May 11, 2012 for Application No. 2008-553535 (English translation).
Lee, et al. Polymer nanoengineering for biomedical applications. Annals Biomed. Eng. 2006; 34:75-88.
Lu, et al. New valve and bonding designs for microfluidic biochips containing proteins. Anal. Chem. 2007; 79:994-1001.
Office action dated May 22, 2012 for U.S. Appl. No. 12/526,015.
Oh, et al. A review of microvalves. J. Micromech. Microeng. 2006; 16:R13-R39.
Samel. Novel Microfluidic devices based on a thermally responsive PDMS composite. KTH Royal Institute of Technology, Stockholm, Sweden. 2007; 1-80.
Tajima, et al. Physiochemical properties and morphology of fluorocarbon films synthesized on crosslinked polyethylene by capacitively coupled octafluorocyclobutane plasma. J. Phys. Chem. C. 2007; 111(11):4358-4367.
Willis, et al. Monolithic teflon membrane valves and pumps for harsh chemical and low-temperature use. Lab Chip. 2007; 7:1469-1474.
Zhang, et al. PMMA/PDMS valves and pumps for disposable microfluidics. Lap Chip. 2009; 9:3088-3094.
U.S. Appl. No. 13/075,165, filed Mar. 29, 2011, Eberhart et al.
U.S. Appl. No. 13/113,968, filed May 23, 2011, Majlof et al.
Armani, et al. Re-configurable fluid circuits by PDMS elastomer micromachining. Proceedings of IEEE Micro Electro Mechanical Systems: MEMS. 1999; 222-227.
European search report and search opinion dated Jun. 6, 2011 for Application No. 10011511.2.
International search report and written opinion dated Jun. 9, 2011 for PCT Application No. US2011/30973.
Notice of allowance dated Jun. 9, 2011 for U.S. Appl. No. 12/831,949.

(56) References Cited

OTHER PUBLICATIONS

U.S. Appl. No. 13/287,398, filed Nov. 2, 2011, Jovanovich et al.
Amendment and Request for Correction of Inventorship mailed Jan. 10, 2008 in U.S. Appl. No. 10/750,533.
Anderson, et al. A miniature integrated device for automated multistep genetic assays. Nucleic Acids Research. 2000;28:e60.
Bings, et al. Microfluidic Devices Connected to Fused-Silica Capillaries with Minimal Dead Dead Volume. Analytical Chemistry. 1999;71(15):3292-3296.
Blazej, et al. Microfabricated bioprocessor for integrated nanoliter-scale Sanger DNA sequencing. Proc. Natl. Acad. Sci. USA 2006;103:7240-7245.
Blazej, et al. Polymorphism Ratio Sequencing: A New Approach for Single Nucleotide Polymorphism Discovery and Genotyping. Genome Research. 2003;13:287-293.
Brenner, et al. Gene expression analysis by massively parallel signature sequencing (MPSS) on microbead arrays. Nature Biotechnology. 2000;18(6):630-634.
Buchholz, et al. The use of light scattering for precise characterization of polymers for DNA sequencing by capillary electrophoresis. Electrophoresis. 2001;22:4118-4128.
CAPLUS abstract of Krokhin et al. Modified silica as a stationary phase for ion chromatography. Journal of Chromatography A. 1995;706:93-8.
Chan, et al. Microfabricated Polymer Devices for Automated Sample Delivery of Peptides for Analysis by Electrospray Ionization Tandem Mass Spectrometry. Analytical Chemistry. 1999;71(20):4437-4444.
Chiem, et al. Microchip systems for immunoassay: an integrated immunoreactor with electrophoretic separation for serum theophylline determination. Clinical Chemistry.1998;44(3):591-598.
Chiem, et al. Room temperature bonding of micromachined glass devices for capillary electrophoresis. Sensors and Actuators. 2000;B63(3):147-152.
Chinese office action dated Jul. 8, 2011 for CN 200580035911.7. (In Chinese with English translation).
Coleman, et al. A sequential injection microfluidic mixing strategy. Microfluidics and Nanofluidics. 2005;319-327.
Curcio, et al. Continuous Segmented-Flow Polymerase Chain Reaction for High-Throughput Miniaturized DNA Amplification. Analytical Chemistry. 2003;75(1):1-7.
Datasheet Cycle Sequencing, Retrieved from the internet, URL:http//answers.com/topic/cycle sequencing. Printed Sep. 3, 2010, pp. 1-2.
Diehl, et al. BEAMing: single-molecule PCR on microparticles in water-in-oil emulsions. Nature Methods. 2006;3(7):551-9.
Doherty, et al. Sparsely Cross-linked "Nanogel" Matrices as Fluid, Mechanically Stablized Polymer Networks for High-Throughput Microchannel DNA Sequencing. Analytical Chemistry. 2004;76:5249-5256.
Doherty, et al. Sparsely cross-linked "nanogels" for microchannel DNA sequencing. Electrophoresis. 2003;24(24):4170-4180.
Dorfman, et al. Contamination-Free Continuous Flow Microfluidic Polymerase Chain Reaction for Quantitative and Clinical Applications. Analytical Chemistry. 2005;77(11):3700-3704.
Doyle, et al. Self-Assembled Magnetic Matrices for DNA Separation Chips. Science. 2000;295:2237.
Dressman, et al. Transforming single DNA molecules into fluorescent magnetic particles for detection and enumeration of genetic variations. Proc Natl Acad Sci USA. 2003;100(15):8817-8822.
Emrich, et al. Microfabricated 384-Lane Capillary Array Electrophoresis Bioanalyzer for Ultrahigh-Throughput Genetic Analysis. Analytical Chemistry. 2002;74(19):5076-5083.
Ericson, et al. Electroosmosis- and Pressure-Driven Chromatography in Chips Using Continuous Beds. Analytical Chemistry. 2000;72(1):81-87.
European search report dated Dec. 18, 2009 for Application No. 03808583.3.
European search report dated Sep. 1, 2010 for Application No. 5804847.1.
Ewing, et al. Base-Calling of Automated Sequencer Traces Using Phred. I. Accuracy Assessment. Genome Research. 1998;8:175-185.
Ewing, et al. Base-Calling of Automated Sequencer Traces Using Phred. II. Error probabilities. Genome Research. 1998;8:186-194.
Figeys, et al. A Microfabricated Device for Rapid Protein Identification by Microelectrospray Ion Trap Mass Spectrometry. Analytical Chemistry. 1997;69(16):3153-3160.
Figeys, et al. An Integrated Microfluidics-Tandem Mass Spectrometry System for Automated Protein Analysis. Analytical Chemistry. 1998;70(18):3728-3734.
Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications in Mass Spectrometry. 1998;12:1435-1444.
Figeys, et al. Nanoflow Solvent Gradient Delivery from a Microfabricated Device for Protein Identifications by Electrospray Ionization Mass Spectrometry. Analytical Chemistry. 1998;70(18):3721-3727.
Francis, et al. Flow analysis based on a pulsed flow of solution: theory, instrumentation and applications. Talanta. 2002;58(6):1029-1042.
Ghadessy, et al. Directed evolution of polymerase function by compartmentalized self-replication. Proc Natl Acad Sci USA. 2001;98:4552-4557.
Giddings, et al. A software system for data analysis in automated DNA sequencing. Genome Research. 1998;8:644-665.
Goll, et al. Microvalves with bistable buckled polymer diaphragms. Journal of Micromechanics and Microengineering. 1996;6:77-79.
Grover, et al. An integrated microfluidic processor for single nucleotide polymorphism-based DNA computing. Lab on a Chip. 2005;5(10):1033-1040.
Grover, et al. Development and multiplexed control of latching pneumatic valves using microfluidic logical structures. Lab on a chip. 2006;6:623-631.
Grover, et al. Monolithic membrane valves and diaphragm pumps for practical large-scale integration into glass microfluidic devices. Sensors and Actuators. 2003;B89:315-323.
Grover, et al. Practical Valves and Pumps for Large-Scale Integration into Microfludic Analysis Devices. Micro Total Analysis Systems. 2002;1:136-138.
Hansen, et al. A robust and scalable microfluidic metering method that allows protein crystal growth by free interface diffusion. Proc Natl Acad Sci USA. 2002;99(26):16531-16536.
Harrison, et al. Micromachining a Miniaturized Capillary Electrophoresis-Based Chemical Analysis System on a Chip. Science. 1993;261(5123):895-897.
Hayes, et al. EDGE: A Centralized Resource for the Comparison, Analysis, and Distribution of Toxicogenomic Information. Molecular Pharmacology. 2005;67(4):1360-1368.
Hultman, et al. Bidirectional Solid-Phase Sequencing of In Vitro-Amplified Plasmid DNA. BioTechniques. 1991;10(1):84-93.
International Preliminary Report for corresponding PCT Application No. PCT/CA2000/01421 dated Feb. 14, 2002.
International Preliminary Report for corresponding PCT Application No. PCT/US2005/018678 dated Nov. 13, 2007.
International Preliminary Report for corresponding PCT Application No. PCT/US2005/033347 dated Mar. 20, 2007.
International Preliminary Report for corresponding PCT Application No. PCT/US2007/007381 dated Sep. 23, 2008.
International Preliminary Report for corresponding PCT Application No. PCT/US2007/02721 dated Aug. 5, 2008.
International Preliminary Report for corresponding PCT Application No. PCT/US2007/061573 dated Aug. 26, 2008.
International search report and written opinion dated Jan. 5, 2012 for PCT Application No. US2011/048527.
International search report and written opinion dated Oct. 26, 2011 for PCT Application No. US11/38180.
International search report dated Oct. 6, 2010 for PCT Application No. US10/37545.
International search report dated Apr. 5, 2001 for PCT Application No. CA2000/01421.
International search report dated May 14, 2010 for PCT Application No. US2009/06640.

(56) References Cited

OTHER PUBLICATIONS

International search report dated Jul. 11, 2008 for PCT Application No. US07/61573.
International search report dated Jul. 30, 2010 for PCT Application No. US2010/36464.
International search report dated Aug. 18, 2009 for PCT Application No. US09/00419.
International search report dated Aug. 23, 2006 for PCT Application No. US2005/033347.
International search report dated Aug. 26, 2004 PCT Application No. US2003/41466.
International search report dated Sep. 25, 2007 for PCT Application No. US2007/02721.
International Search Report for PCT/US2005/033347.
International written opinion dated Oct. 6, 2010 for PCT Application No. US10/37545.
International written opinion report dated Jul. 30, 2010 for PCT Application No. US2010/36464.
Jacobson, et al. Electrokinetic Focusing in Microfabricated Channel Structures. Anal. Chem., 1997, 69 (16), pp. 3212-3217.
Japanese office action dated May 27, 2011 for Application No. 2007-532553 (in Japanese with English translation).
Japanese office action dated Jul. 28, 2011 for Application No. 2008-553535 (in Japanese with English translation).
Ju, et al. Fluorescence energy transfer dye-labeled primers for DNA sequencing and analysis. Proc. Natl. Acad. Sci. USA. 1995;92:4347-4351.
Kan, et al. A novel thermogelling matrix for microchannel DNA sequencing based on poly-N-alkoxyalkylaclylamide copolymers. Electrophoresis. 2003;24(24):4161-4169.
Koh, et al. Integrating Polymerase Chain Reaction, Valving, and Electrophoresis in a Plastic Device for Bacterial Detection. Analytical Chemistry. 2003;75(17):4591-4598.
Kopp, et al. Chemical Amplification Continuous-Flow PCR on a Chip. Science. 1998;280:1046-1048.
LaGally, et al. Fully integrated PCR-capillary electrophoresis microsystem for DNA analysis. Lab on a Chip. 2001;1(2):102-107.
LaGally, et al. Integrated Portable Genetic Analysis Micro system for Pathogen/Infectious Disease Detection. Analytical Chemistry. 2004;76:3162-3170.
LaGally, et al. Monolithic integrated microfluidic DNA amplification and capillary electrophoresis analysis system. Sensors and Actuators. 2000;B63(3):138-146.
LaGally, et al. Single-Molecule DNA Amplification and Analysis in an Integrated Microfluidic Device. Analytical Chemistry. 2001;73(3): 565-570.
Lazar, et al. Subattomole-Sensitivity Microchip Nanoelectrospray Source with Time-of-Flight Mass Spectrometry Detection. Analytical Chemistry. 1999;71(17):3627-3631.
Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.
Li, et al. Rapid and sensitive separation of trace level protein digests using microfabricated devices coupled to a quadrupole—time-of-flight mass spectrometer. Electrophoresis. 2000;21:198-210.
Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.
Licklider, et al. A Micromachined Chip-Based Electrospray Source for Mass Spectrometry. Analytical Chemistry. 2000;72(2):367-375.
Lisec, et al. A bistable pneumatic microswitch for driving fluidic components. Sensors and Actuators. 1996;A54:746-749.
Liu, et al. Automated parallel DNA sequencing on multiple channel microchips. Proc. Natl. Acad. Sci. USA. 2000;97(10):5369-5374.
Liu, et al. Optimization of High-Speed DNA Sequencing on Microfabricated Capillary Electrophoresis Channels. Analytical Chemistry. 1999;71:566-573.
Margulies, et al. Genome sequencing in microfabricated high-density picolitre reactors. Nature. 2005;437(7057):376-80.
Melin, et al. A Passive 2-Dimensional Liquid Sample Micromixer. 7th International Conference on Miniaturized Chemical and Biochemical Analysis Systems. 2003;167-170.
Mitra, et al. Digital genotyping and haplotyping with polymerase colonies. Proc Natl Acad Sci USA. 2003.100(10):15926-5931.
Norris, et al. Fully-integrated, multiplexed STR-based human identification using a single microfluidic chip and automated instrument. Available at http://www.promega.com/geneticidproc/ussymp20proc/oralpresentations/landersbienvenue.pdf Accessed Jun. 2, 2010.
Obeid, et al. Microfabricated Device for DNA and RNA Amplification by Continuous-Flow Polymerase Chain Reaction and Reverse Transcription-Polymerase Chain Reaction with Cycle Number Selection. Analytical Chemistry. 2003;75(2): 288-295.
Ocvirk, et al. High Performance Liquid Chromatography Partially Integrated onto a Silicon Chip. Analytical Methods and Instrumentation. 1995;2:74-82.
Ocvirk, et al. Optimization of confocal epifluorescence microscopy for microchip-based miniaturized total analysis systems. The Analyst. 1998;123:1429-1434.
Office Action Final dated Feb. 19, 2008 issued in U.S. Appl. No. 10/540,658.
Office Action Final dated Feb. 6, 2008 issued in U.S. Appl. No. 11/139,018.
Office Action mailed Apr. 27, 2007 in U.S. Appl. No. 11/139,018, filed May 25, 2005.
Office Action mailed Jul. 2, 2007 in U.S. Appl. No. 10/540,658, filed Jun. 23, 2005.
Office Action mailed Jul. 12, 2007 in U.S. Appl. No. 10/750,533, filed Dec. 29, 2003.
Ohori, et al. Partly disposable three-way mirovalve for a medical micro total analysis system (muTAS). Sensors and Actuators. 1998;A64(1): 57-62.
Oleschuk, et al. Trapping of Bead-Based Reagents within Microfluidic Systems: On-Chip Solid-Phase Extraction and Electrochromatography. Analytical Chemistry. 2000;72:585-590.
Olsen, et al. Immobilization of DNA Hydrogel Plugs in Microfluidic Channels. Analytical Chemistry. 2002;74:1436-1441.
Paegel, et al. High-throughput DNA sequencing with a 96-lane capillary array electrophoresis bioprocessor. Proc Natl Acad Sci USA. 2002;99:574-579.
Paegel, et al. Microchip Bioprocessor for Integrated Nanovolume Sample Purification and DNA Sequencing. Analytical Chemistry. 2002;74(19):5092-5098.
Paegel, et al. Microfluidic devices for DNA sequencing: sample preparation and electrophoretic analysis. Current Opinion in Biotechnology. 2003;14(1):42-50.
Paegel, et al. Turn Geometry for Minimizing Band Broadening in Microfabricated Capillary Electrophoresis Channels. Analytical Chemistry. 2000;72:3030-3037.
PCT Notification of Transmittal of the International Search Report and The Written Opinion of the International Searching Authority, or the Declaration, mailed Jun. 17, 2008, Application No. PCT/US2007/082568.
Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.
Ramsey, et al. Generating Electrospray from Microchip Devices Using Electroosmotic Pumping. Analytical Chemistry. 1997;69(6):1174-1178.
Rohr, et al. Porous polymer monoliths: Simple and efficient mixers prepared by direct polymerization in the channels of microfluidic chips. Electrophoresis. 2001;22:3959-3967.
Rye, et al. High-sensitivity two-color detection of double-stranded DNA with a confocal fluorescence gel scanner using ethidium homodimer and thiazole orange. Nucleic Acids Research. 1991;19(2):327-333.
Scherer, et al. High-Pressure Gel Loader for Capillary Array Electrophoresis Microchannel Plates. Biotechniques. 2001;31(5):1150-1154.

(56) References Cited

OTHER PUBLICATIONS

Schomburg, et al. Design Optimization of Bistable Microdiaphragm Valves. Sensors and Actuators. 1998;A64:259-264.
Seifar, et al. Capillary electrochromatography with 1.8-mum ODS-modified porous silica particles. Journal of Chromatography. 1998; A808:71-77.
Simpson, et al. High-throughput genetic analysis using microfabricated 96-sample capillary array electrophoresis microplates. Proc Natl Acad Sci USA. 1998;95:2256-2261.
Simpson, et al. Microfabrication Technology for the Production of Capillary Array Electrophoresis Chips. Biomedical Microdevices. 1998;1:7-26.
Soper, et al. Sanger DNA Sequencing Reactions Performed in a Solid-Phase Nanoreactor Directly Coupled to Capillary Gel Electrophoresis. Analytical Chemistry. 1998;70:4036-4043.
Spiering, et al. Novel microstructures and technologies applied in chemical analysis techniques. 1997 International Conference on Solid-State Sensors and Actuators. 1997;1:511-514.
Takao, et al. A Pneumatically Actuated Full In-Channel Microvalve With MOSFET-Like Function in Fluid Channel Networks. Journal of Microelectromechanical Systems. 2002;11(5):421-426.
Takao, et al. Microfluidic Integrated Circuits for Signal Processing Using Analogous Relationship Betweeen Pneumatic Microvalve and MOSFET. Journal of Microelectromechanical Systems. 2003;12(4):497-505.
Thomas, et al. Application of Genomics to Toxicology Research. Environmental Health Perspectives. 2002;110(6):919-923.
Thorsen, et al. Microfluidic Large-Scale Integration. Science. 2002;298(5593):580-584.
Tice, et al. Formation of Droplets and Mixing in Multiphase Microfluidics at Low Values of the Reynolds and the Capillary Numbers. Langmuir. 2003;19:9127-9133.
Unger, et al. Monolithic Microfabricated Valves and Pumps by Multilayer Soft Lithography. Science. 2000;288:113-116.
Van Der Moolen, et al. A Micromachined Injection Device for CZE: Application to Correlation CZE. Analytical Chemistry. 1997;69(20):4220-4225.
Van Der Moolen, et al. Correlation Capillary Zone Electrophoresis, a Novel Technique to Decrease Detection Limits. Chromatographia. 1995;40(7/8):368-374.
Vazquez, et al. Electrophoretic Injection within Microdevices. Analytical Chemistry. 2002;74:1952-1961.
Veenstra, et al. The design of an in-plane compliance structure for microfluidical systems. Sensors and Actuators. 2002;B81:377-383.
Waller, et al. Quantitative Immunocapture PCR Assay for Detection of *Campylobacter jejuni* in Foods. Applied Environmental Microbiology. 2000; 66(9):4115-4118.
Weimer, et al. Solid-Phase Capture of Proteins, Spores, and Bacteria. Applied Environmental Microbiology. 2001;67(3):1300-1307.
Wen, et al. Microfabricated isoelectric focusing device for direct electrospray ionization-mass spectrometry. Electrophoresis. 2000;21:191-197.
Wikipedia brochure for defining stocahstic process. Sep. 2, 2009.
Williams, et al. Amplification of complex gene libraries by emulsion PCR. Nature Methods. 2006;3(7):545-50.
Woolley, et al. Functional Integration of PCR Amplification and Capillary Electrophoresis in a Microfabricated DNA Analysis Device. Analytical Chemistry. 1996;68(23):4081-4086.
Wright, et al. Behavior and Use of Nonaqueous Media without Supporting Electrolyte in Capillary Electrophoresis and Capillary Electrochromatography. Analytical Chemistry. 1997;69(16):3251-3259.
Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.
Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.
Xue, et al. Multichannel Microchip Electrospray Mass Spectrometry. Analytical Chemistry. 1997;69(3):426-430.
Yang, et al. A MEMS thermopneumatic silicone rubber membrane valve. Sensors and Actuators. 1998;A64(1):101-108.
Yu, et al. Preparation of Monolithic Polymers with Controlled Porous Properties for Microfluidic Chip Applications Using Photoinitiated Free Radial Polymerization. Journal of Polymer Science. 2002;40:755-769.
Yu, et al. Towards stationary phases for chromatography on a microchip: Molded porous polymer monoliths prepared in capillaries by photoinitiated in situ polymerization as separation media for electrochromatography. Electrophoresis. 2000;21:120-127.
Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.
Zhang, et al. Microfabricated Devices for Capillary Electrophoresis-Electrospray Mass Spectrometry. Analytical Chemistry. 1999;71(15):3258-3264.
U.S. Appl. No. 12/026,510, filed Feb. 5, 2008, Jovanovich et al.
U.S. Appl. No. 12/820,390, filed Jun. 22, 2010, Harrison et al.
U.S. Appl. No. 12/949,623, filed Nov. 18, 2010, Kobrin et al.
International search report and written opinion dated Mar. 24, 2011 for PCT Application No. US2010/58227.
International search report and written opinion dated Sep. 1, 2010 for PCT Application No. US2010/040490.
Japanese Office Action dated Dec. 21, 2010 for Application No. JP2001-540363 (in Japanese with English translation).
Japanese Office Action dated Apr. 27, 2010 for Application No. JP2001-540363 (in Japanese with English translation).
MillGat pump user manual, version 2.12, published 2005, pp. 1-28.
Norris, et al. Fully-integrated, multiplexed STR-based human identification using a single microfluidic chip and automated instrument. Available at http://www.promega.com/geneticidproc/ussymp20proc/oralpresentations/landersbienvenue.pdf. Accessed Jun. 2, 2010.
Dorfman, et al. Contamination-Free Continuous Flow Microfluidic Polymerase Chain Reaction for Quantitative and Clinical Applications. Analytical Chemistry: 2005;77(11):3700-3704.
LaGally, et al. Integrated Portable Genetic Analysis Microsystem for Pathogen/Infectious Disease Detection. Analytical Chemistry. 2004;76:3162-3170.
Margulies, et al. Genome sequencing in microfabricated high-density picolitre reactors. Nature. 2005;437(7057):376-80. (Abstact only).
Ohori, et al. Partly disposable three-way mirovalve for a medical micro total analysis system (muTAS). Sensors and Actuators. 1998;A64(1); 57-62.
Seifar, et al. Capillary electrochromatography with 1.8-mum ODS-modified porous silica particles. Journal of Chromatography. 1998;A808:71-77.
Wen, et al. Microfabricated isoelectric focusing device for direct electrospray ionization—mass spectrometry. Electrophoresis. 2000;21:191-197.
Office action dated Aug. 24, 2012 for U.S. Appl. No. 12/026,510.
Office action dated Nov. 14, 2012 for U.S. Appl. No. 12/526,015.

\* cited by examiner

*Figure 1. Pumping on a microchip.*

*Figure 2. MOV valve.*

Figure 3. MOV devices from top to bottom: valve, router, mixer, bead capture. Approximately to scale.

Figure 4. Mixing on a microchip.

*Figure 5. Mixing and pumping to a reactor.*

*Figure 6. Mixing on a microchip and delivery to an edge.*

*Figure 7. Input of two streams from an edge using microscale valves and movement to a reactor.*

Figure 8. Mixing more than two streams and moving them to a reactor.

*Figure 9. Mixing with reactor and moving the sample to an edge.*

*Figure 10. Mixing with a reactor and moving the sample to another chamber.*

Figure 11. Two microchip system.

Figure 12. Modular microfluidic interface to couple sample preparation with analysis.

*Figure 13. Modular microfluidic microchips with microvalves with an electrode incorporated on Microchip A.*

*Figure 14. Capturing the sample for improved injection.*

*Figure 15. Multiple channels of sample preparation and analysis.*

Figure 16. Integration of sample preparation, capture, and separation in capillaries using MOV valves and modular microfluidics.

*Figure 17. Moving the sample to a capture region on a second microchip or other device.*

*Figure 18. Injection of sample from capture region to an analysis device which may be a separation channel or other analytical device.*

MBI-026 integrated PCR or cycle sequencing and cleanup microchip. The top panel shows one circuit. The bottom panel shows an 8 channel microchip.

*Figure 20. Readlength (bars) and S/N at 600 bp for integrated on chip nanoliter cycle sequencing and bead-based cleanup. Green bar is the full volume control.*

NanoBioPrep$^{SEQ}$, automated NanoBioProcessor for CAE sequencing

Sample Capture and Purification Module

Figure 24. Flow through MOV valve. Closed configuration (left) allows for movement of fluid in the vertical channel while isolated from the horizontal channel. When in an open configuration (right), the channel can flow into one another.

*Figure 25. Use of flow through valve to eliminate dead volume at an intersection. Conventional MOV valve (left) intersection is less than ideal because it contains a section of dead volume, the section between the valve and the intersection of the tow channel is dead volume. The Flow Through valve system (right) eliminates this dead volume.*

Figure 26. Star (left) and Nested Star (right) for on chip bead capture

Figure 27. Bead capture through use of an increase in cross-section.

*Figure 28. Bead capture in MOV valve. Closed valve configuration (left) allows captures a small amount of beads. Open configuration (right) increases cross-section to capture beads more efficiently.*

*Figure 29. Reservoir (green circle in center) supplies reagent to two channels that in turn are divided again using y-valves.*

Figure 30. Reagent delivery system using a single set of *pumping valves.*

Figure 31. Reagent loop to reduce volume of reagents needed for reactions

Figure 32. Compact Integrated design.

Figure 33 Integrated design.

*Figure 34. Hybrid plastic microchip.*

*Figure 35. Prototype mechanically clamped chip design, exploded view and channel layout.*

View of a mechanically clamped microchip from the top in the top panel and from the bottom in the bottom panel

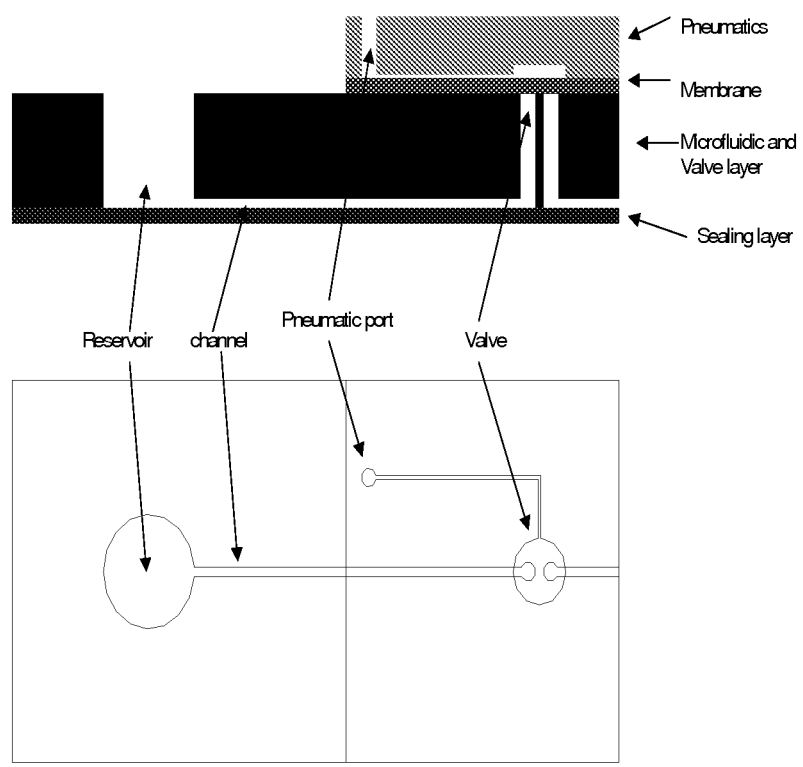
*Figure 37. Layout of mechanically clamped chip with reduced alignment requirements.*

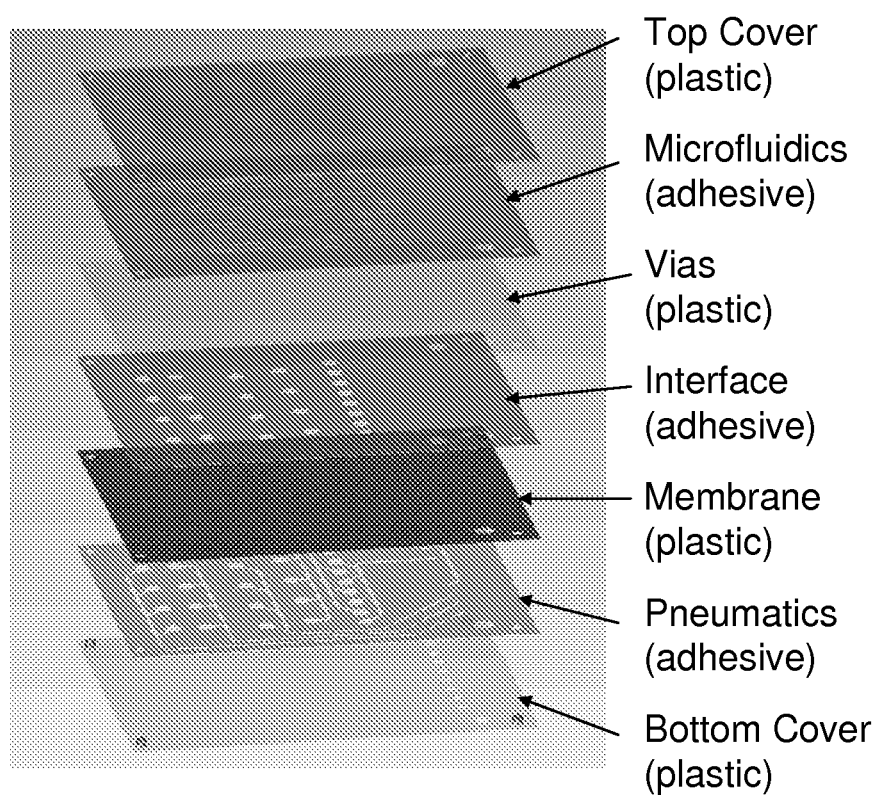
Figure 38. An embodiment of the adhered chip construction.

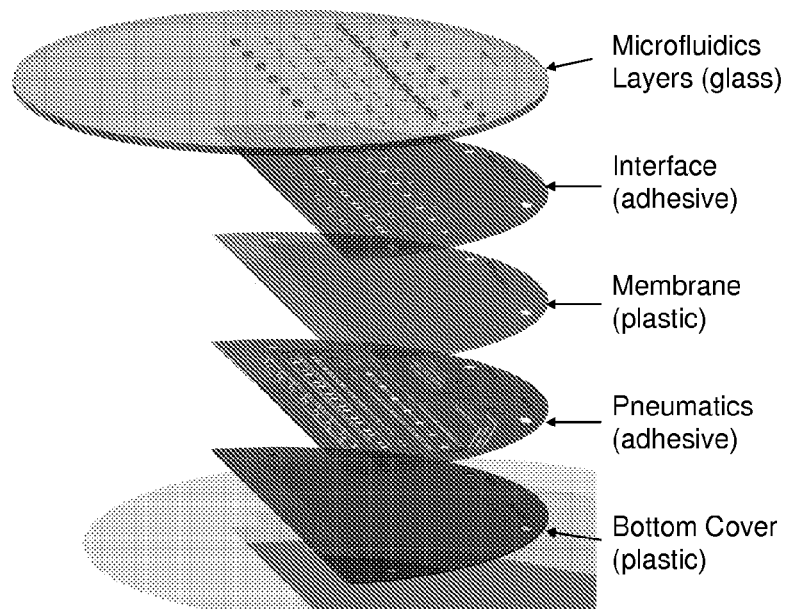
Figure 39. *An embodiment where only part of the chip uses the adhered chip construction. Note that the microfluidics layers could use a material different from glass, such as thermally bonded plastic layers.*

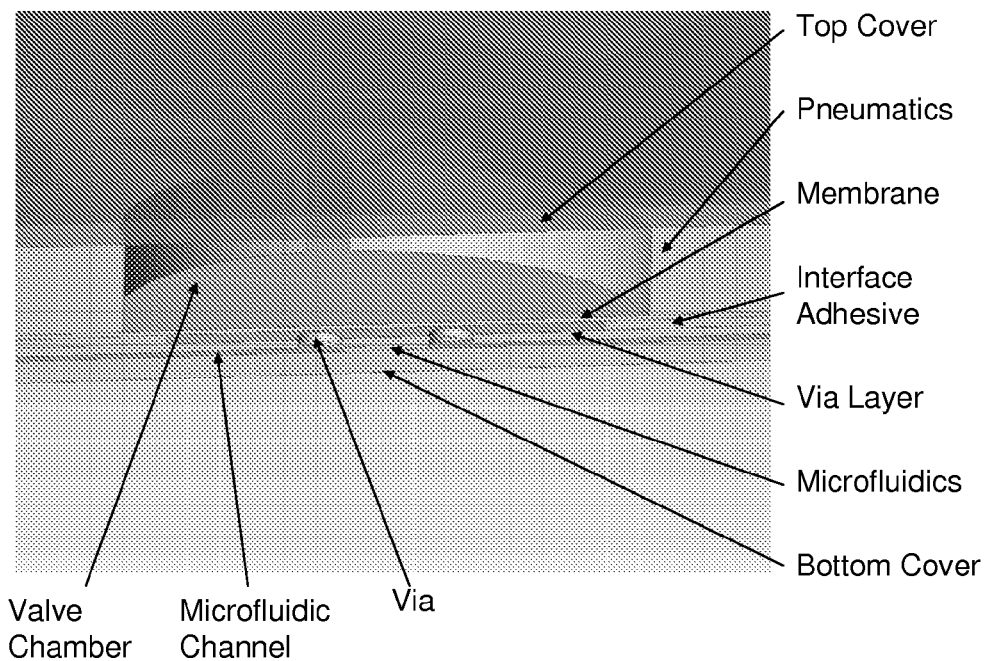
Figure 40. Close-up of a microfluidic valve made with adhesive lamination.

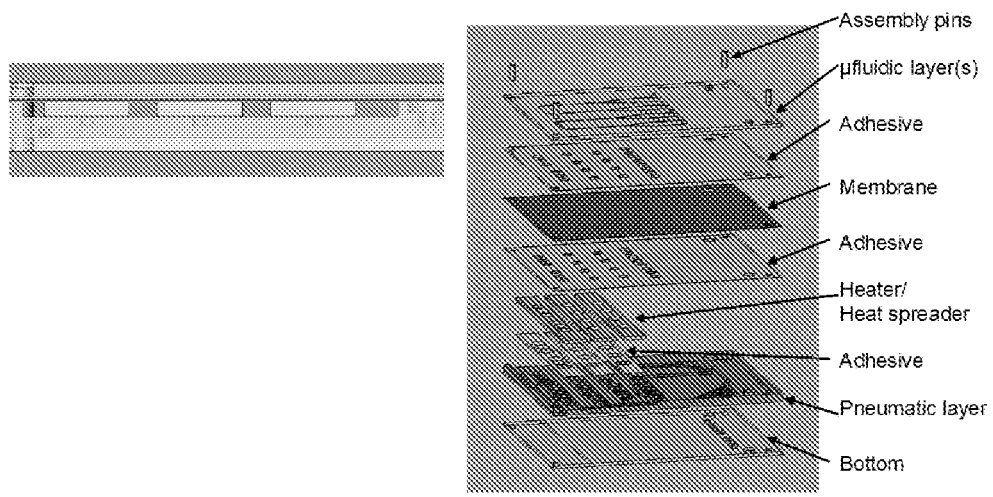
*Figure 41. An adhesive laminated chip incorporating heaters and heat spreaders.*

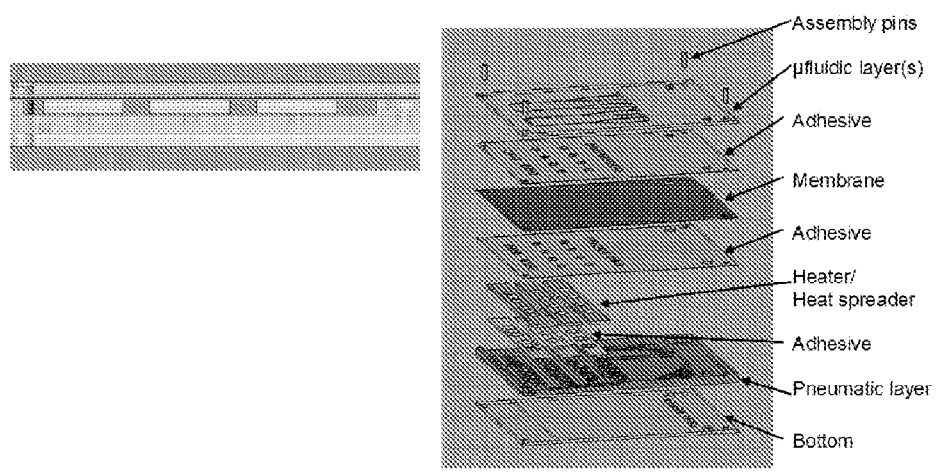
*Figure 42: Structure of a valve fabricated on a three layer plastic laminated microfluidic chip.*

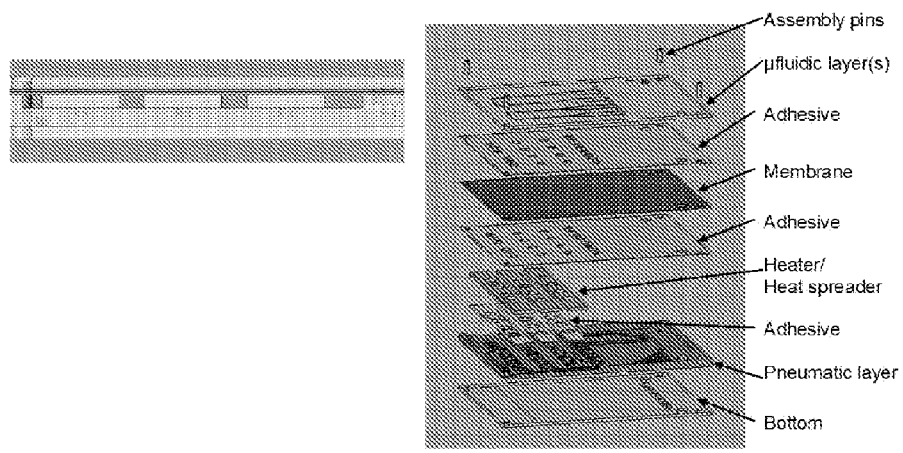
*Figure 43. Cross section of a normally open valve obtained by inflating the membrane during the lamination.*

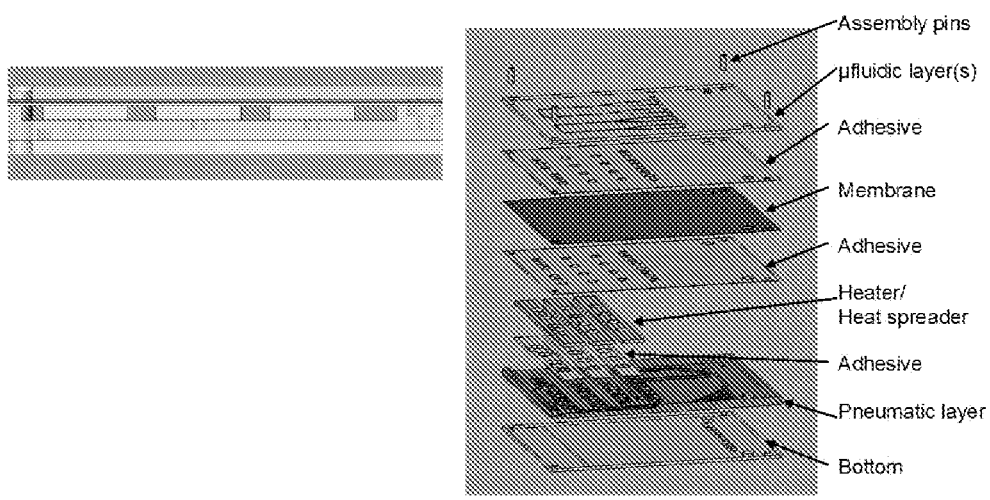
*Figure 44. Cross section of a four layer valve. The valve layer allows multiple air and microfluidic crossings without cross-talking between channels.*

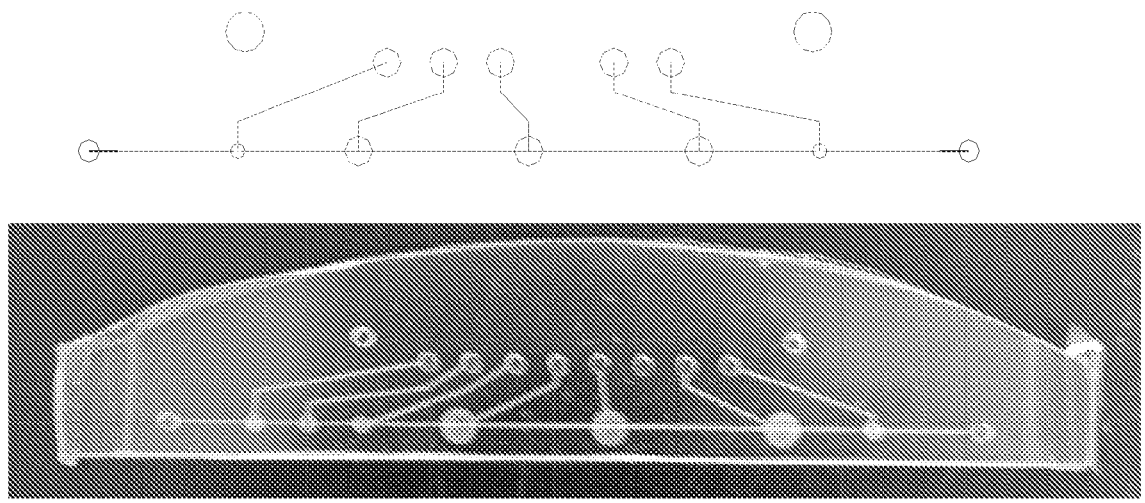
*Figure 45. Mask design and picture of a valve array acrylic chip for bead clean-up protocol.*

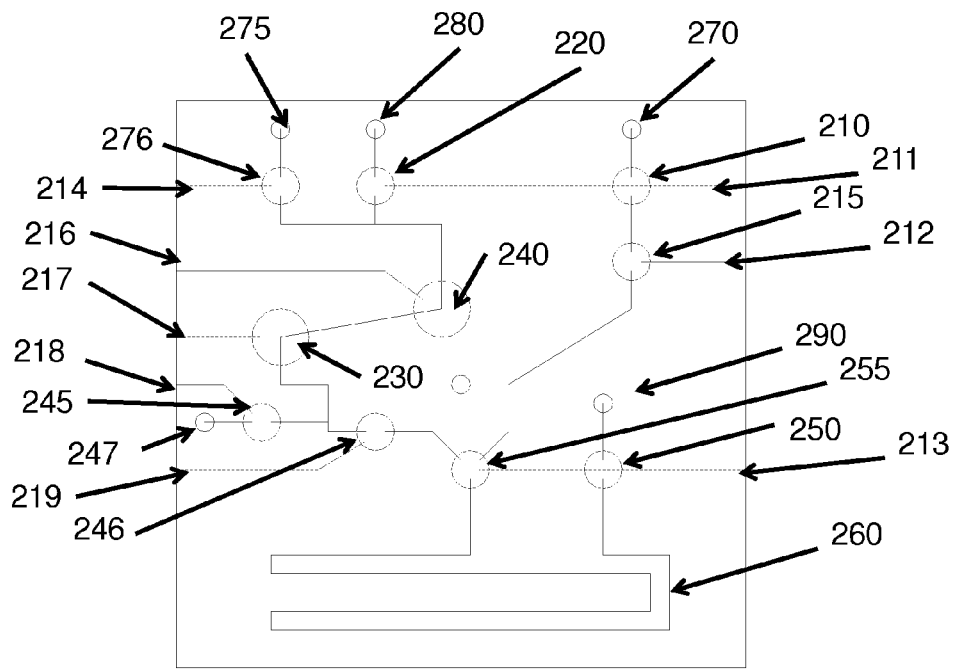
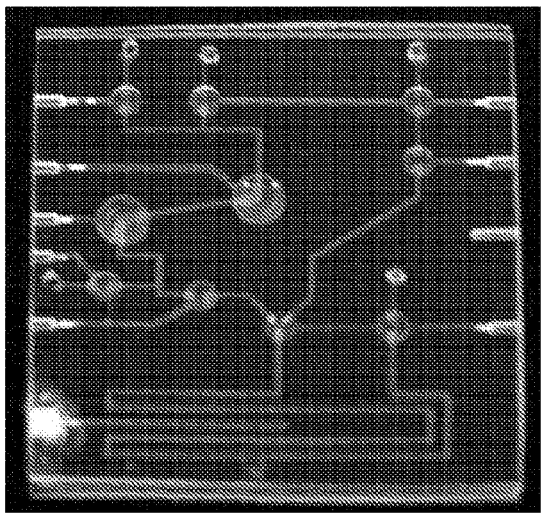
*Figure 46. Design and picture of a 3 layer acrylic chip for forensic applications. The actuation channels are exiting on chip edges for avoiding intersection with microfluidic channels.*

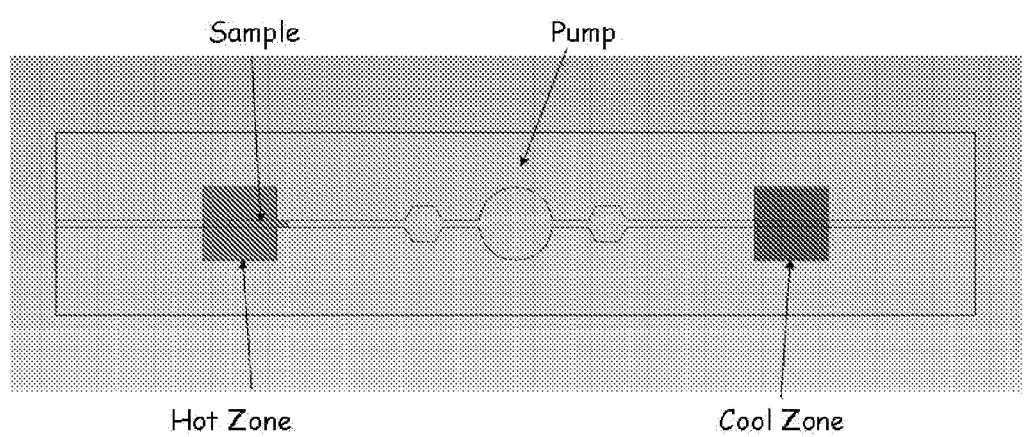
Figure47: Use pump(s) to move sample back & forth between hot & cool zones on the chip.

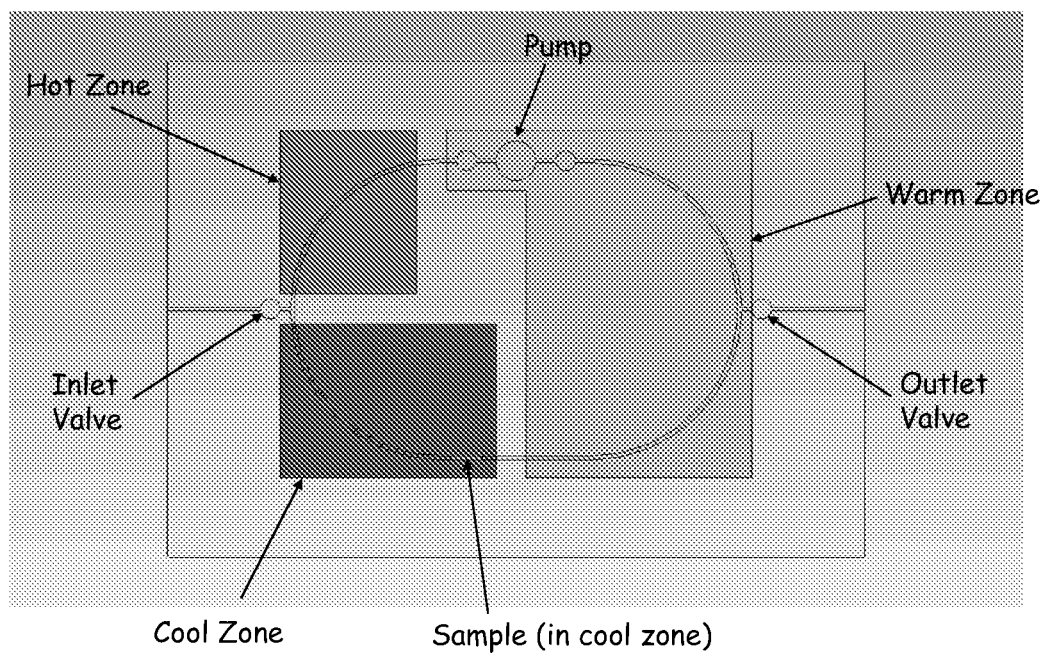
Figure 48. *An implementation of three temperature cycling using an on-chip pump to move the sample among temperature zones.*

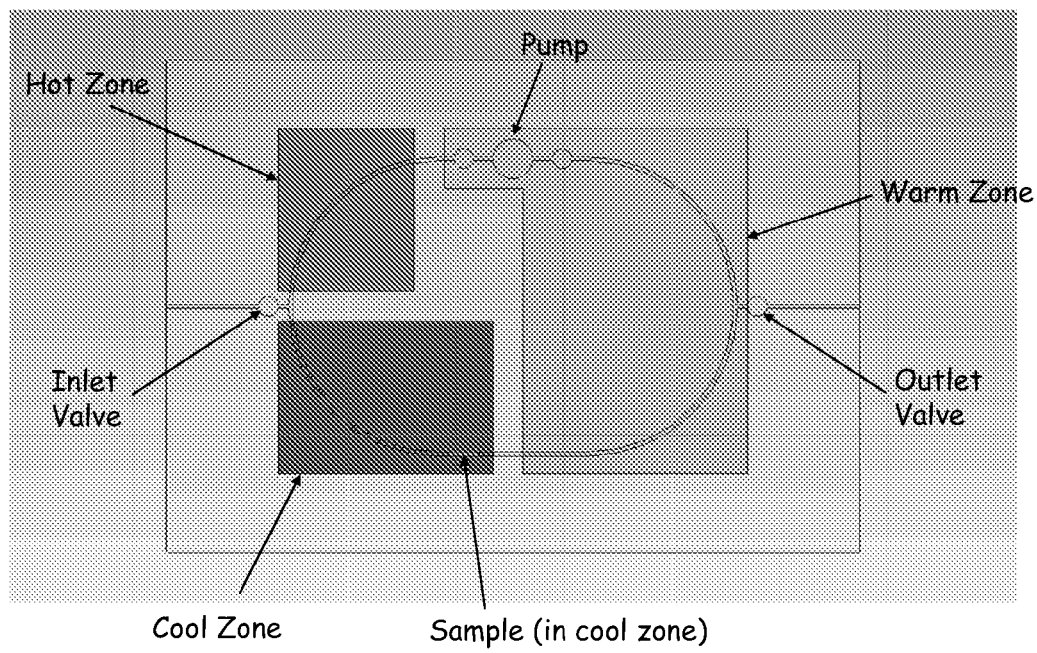
Figure 49: Alternative concept using an immiscible fluid on either side of the sample so the sample does not go through the pumps.

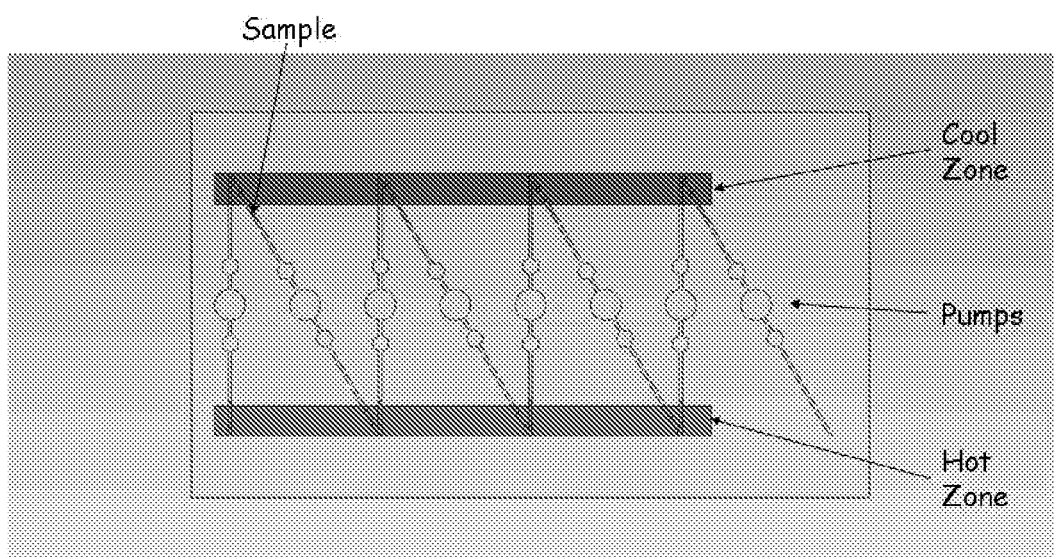
*Figure 50: Use a pipeline to increase throughput.*

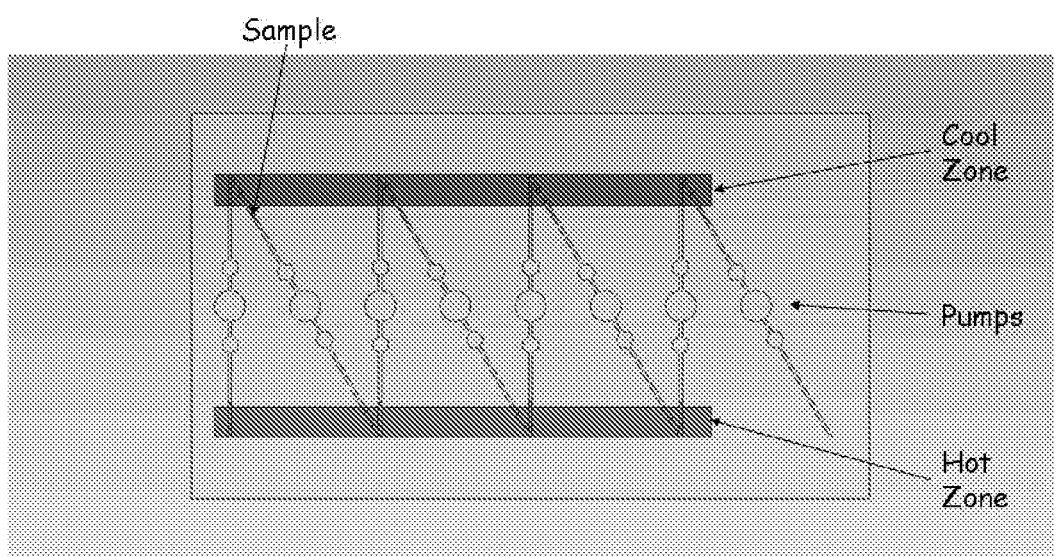
Figure 51. Shuttle cycling with channels and pumps for washing and/or rinsing.

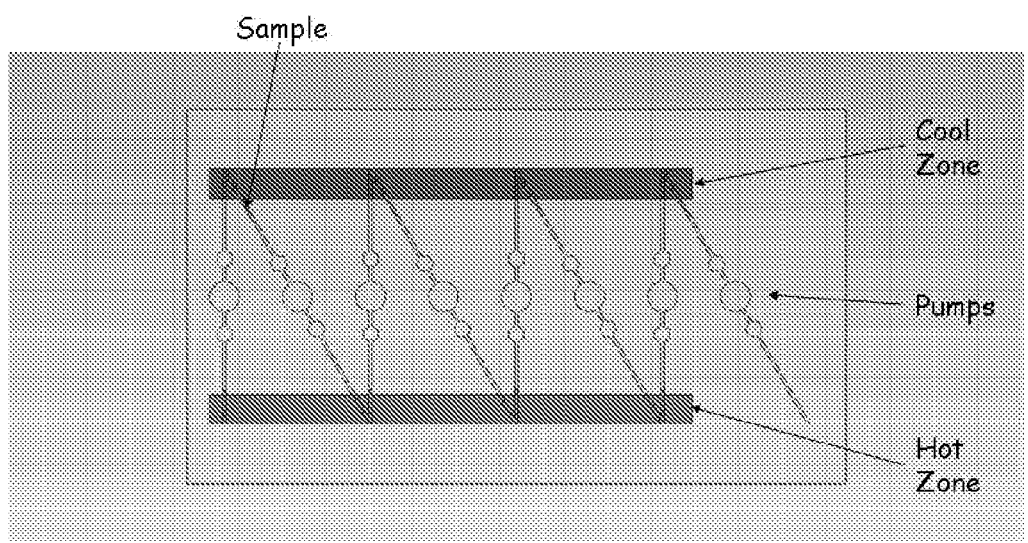
*Figure 52 Two Temperature Shuttle cycling with temperature zones co-located with valves.*

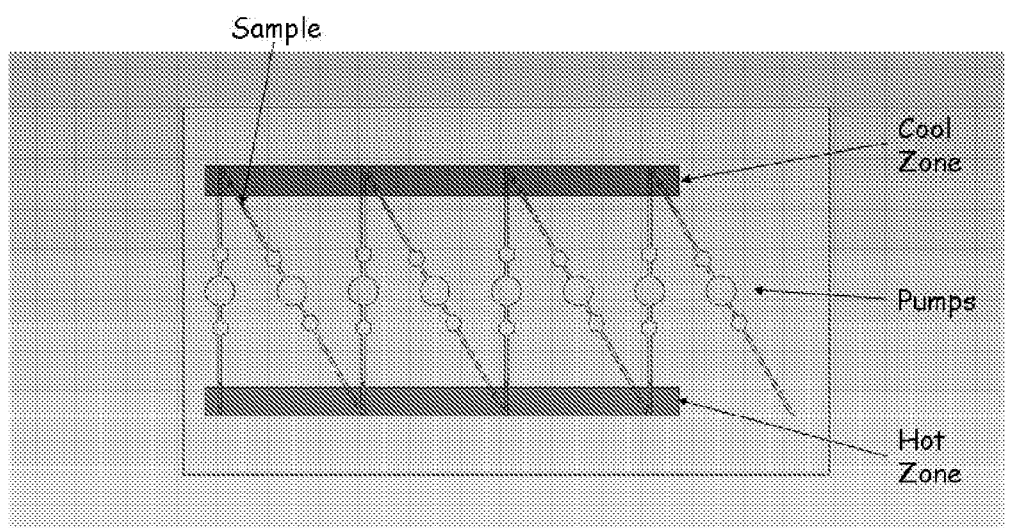
*Figure 53. Three-Temperature Shuttle cycling with temperature zones co-located with valves.*

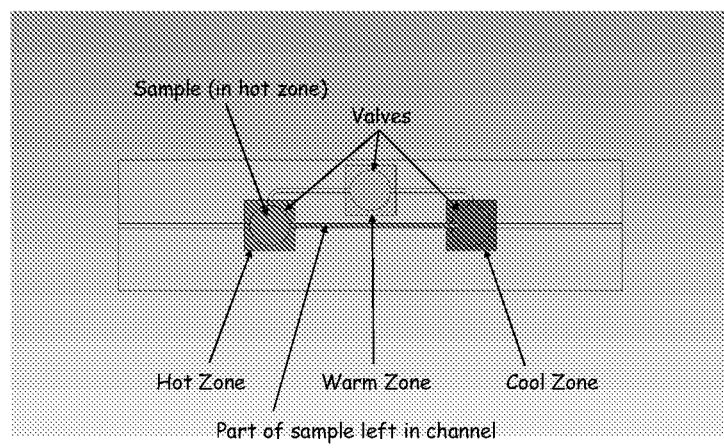
*Figure 54 Three-Temperature Shuttle cycling with temperature zones co-located with valves and circular pumping.*

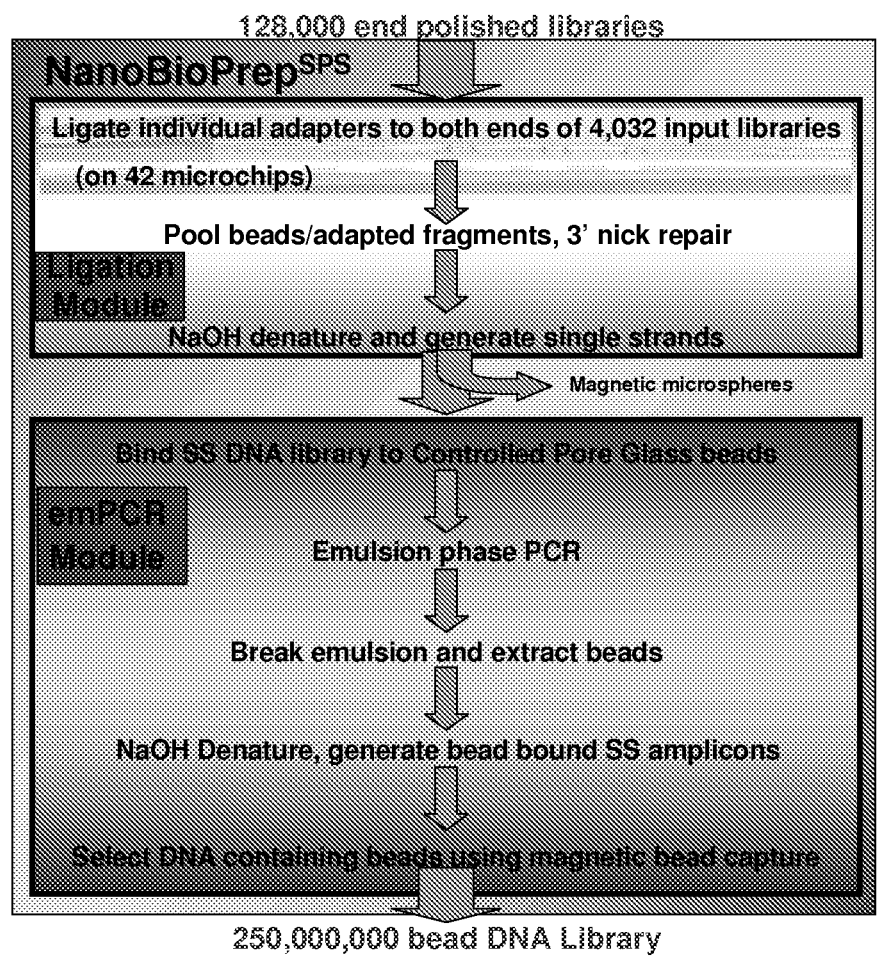
*Figure 55. NanoBioPrep$^{SPS}$ process and modules.*

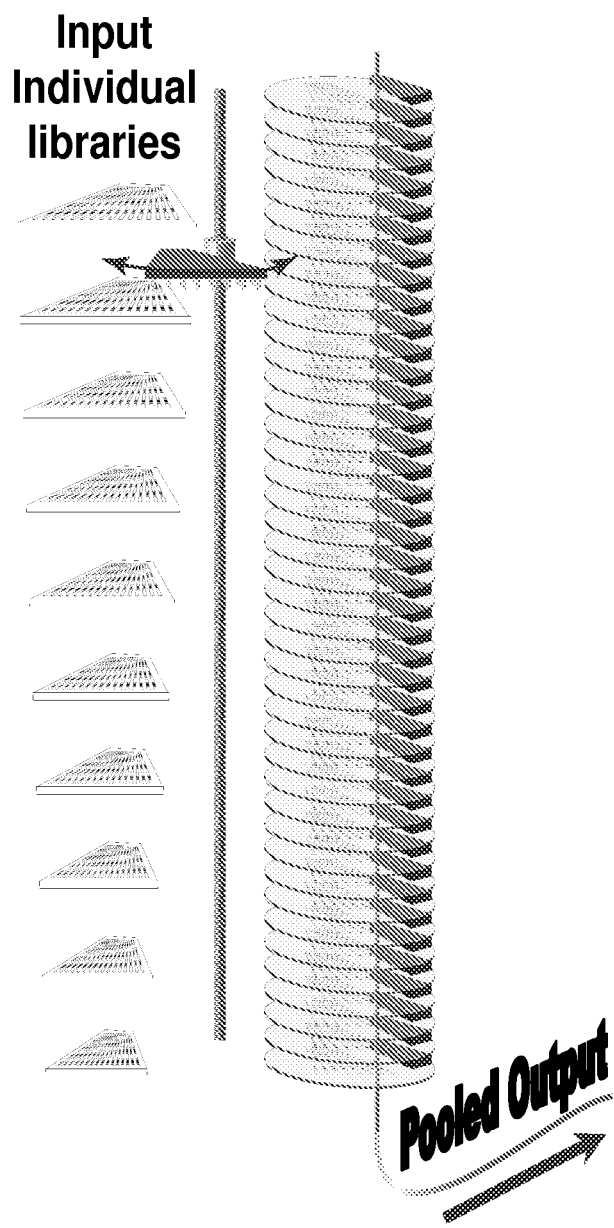
Figure 56. Ligation module microchip stack with 42 microchips with loading from microtiter plates

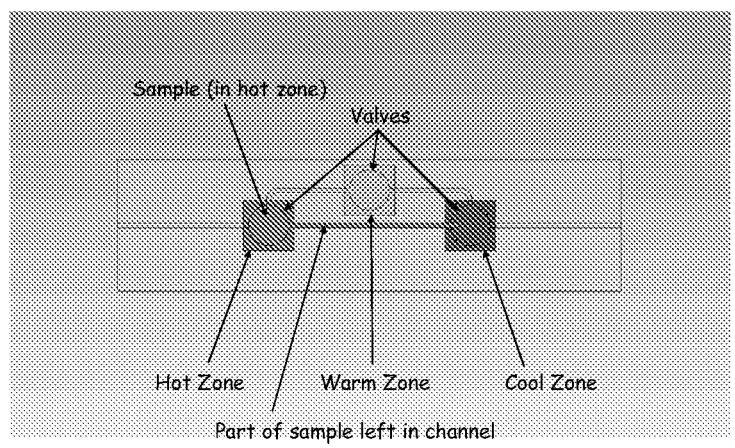
Figure 57. 96-channel capillary cassette to be adapted for loading

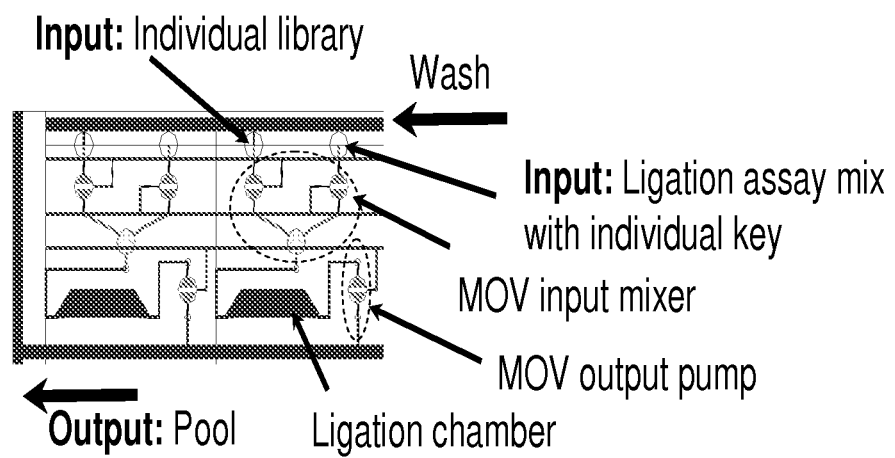
*Figure 58. Two microchip-based ligation circuits.*

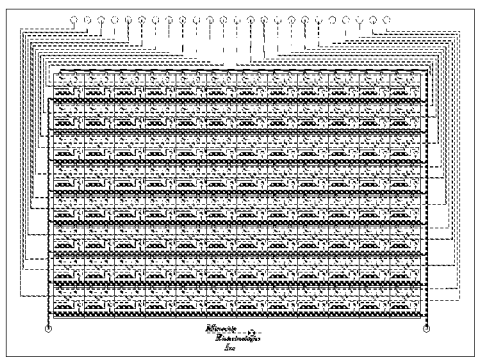
*Figure 59. 96 ligation circuits. The red 16 lines are pneumatics. The blue lines are microfluidics.*

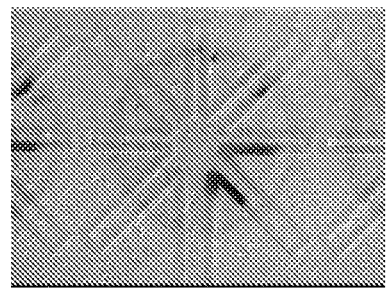
*Figure 60. Magnetic beads trapped on an MBI microchip. Rare earth magnets are used to capture beads in specifically designed "star" capture feature.*

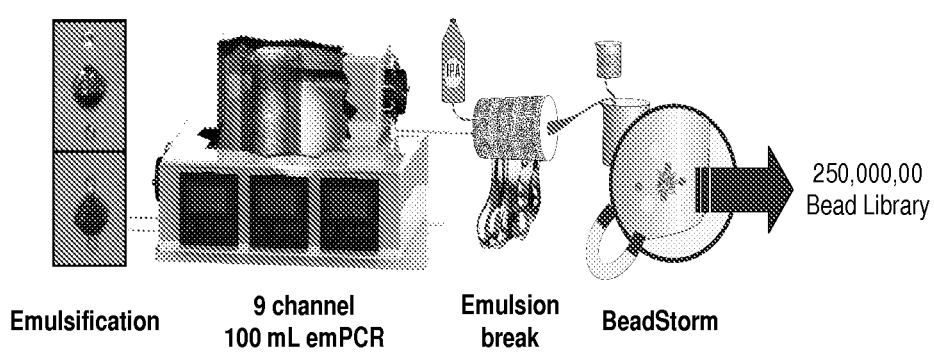
*Figure 61. emPCR amplification.*

Circulating water thermal cycling: three sets of three valves flank the reaction chamber.

Multiplexed latching valve test device, with a four-bit demultiplexer (top box) for routing pressure and vacuum pulses from the single "input" connection to each of sixteen latching valves (bottom box)

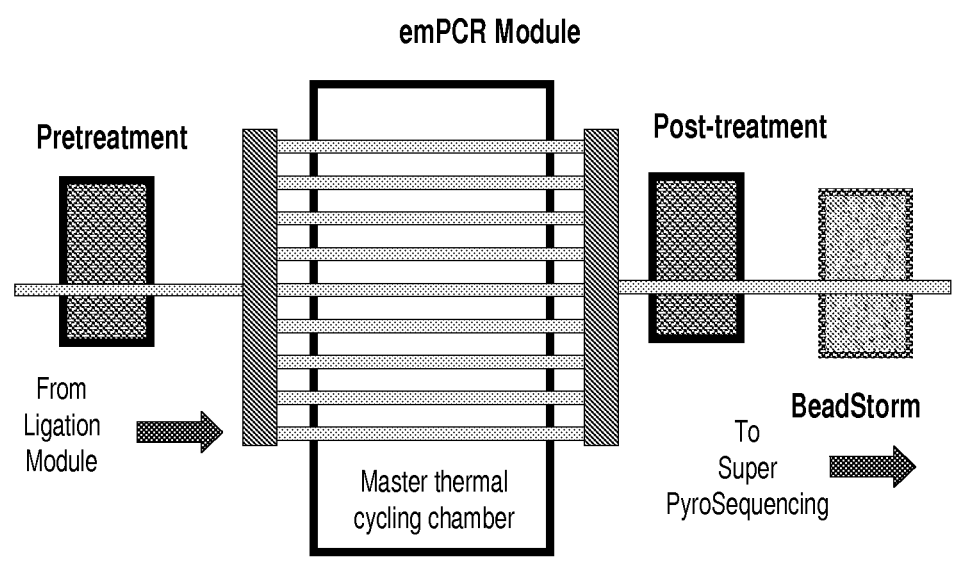
Figure 64. Thermal cycling in the emPCR module.

MICROFLUIDIC AND NANOFLUIDIC DEVICES, SYSTEMS, AND APPLICATIONS

CROSS-REFERENCE

This application is a Continuation Application which claims the benefit of U.S. application Ser. No. 12/526,015, filed Aug. 5, 2009; which is a U.S. National Stage application under 35 USC 371 of PCT Application No. PCT/US08/53099, filed Feb. 5, 2008; which claims the benefit of U.S. Provisional Application No. 60/899,630, filed Feb. 5, 2007. U.S. Provisional Application No. 60/899,630 is incorporated herein by reference in its entirety.

STATEMENT AS TO FEDERALLY SPONSORED RESEARCH

Aspects of this invention were made with government support under one or more of Project No. W911 SR-04-P-0047 awarded by the Department of Defense, Grant No. 5R01HG003583 awarded by the NIH, Contract No. NBCHC050133 awarded by HSARPA, Order No. TTA-1-0014 (Agreement No. W81XWH-04-9-0012) awarded by HSARPA. The government has certain rights in this invention.

BACKGROUND OF THE INVENTION

A variety of microfluidic devices of disparate, design have been developed in the past often with the goal of reducing sample volume requirements in bioanalytical methods, integrating multiple steps into automated processes, integrating sample preparation and analysis, and connecting to the full volume world of samples and procedures.

In the absence of standards controlling external dimensional form factors, the nature of the upstream and downstream external interface, and the length, cross-sectional geometry, and diameter of the internal microfluidic pathways, such microfluidic devices often proved incompatible with one another and with existing upstream purification and downstream analytical devices.

Despite advances in microfabrication, making possible analysis at microliter, even nanoliter or picoliter, scale, many biological and environmental samples are first acquired in volumes far greater than, the scale of existing microfluidic analytical devices.

Modular microfluidic technology can combine moving samples on microchips. While a focus in microfluidics has been integration of multiple functions onto a single device, the objects have been achieved through an alternative approach that allows modular integration of functions across multiple devices. This modular concept is based on technologies, that allow arrays of capillaries to be connected simply by plugging two connectors together (U.S. Pat. No. 6,551,839; U.S. patent application Ser. No. 11/229,065; U.S. Pat. Nos. 6,190,616; 6,423,536; U.S. patent application Ser. No. 09/770,412; U.S. Pat. No. 6,870,185; U.S. patent application Ser. Nos. 10/125,045; 10/540,658; 10/750,533; 11/138,018; all of which are herein incorporated by reference in their entirety). In addition to creating connectors, the interface between the arrays also creates true zero dead-volume valves and routers. The present disclosure provides guidance on how to connect and disconnect microchips containing fluidic circuits to other microchips or arrays of capillaries, develops new microchip designs incorporating two, three, or more microchips, provides new functionality, including fraction collection, new applications, and instrumentation design.

This new technology is termed modular nanofluidics and the use of microchips in modular nanofluidics is referred to as "modular microfluidic microchips" or "modular microchips."

Modular microfluidic microchips have many applications in the life sciences and medicine. Modular microchips create devices can perform single functions or logically clustered groups of functions. More complex processes are created by docking two microdevices and transferring the processed samples. For example, one microdevice might perform PCR amplification and cleanup of a series of target DNAs, a second might perform cycle sequencing reactions, and may connect to a third device that performs DNA sequence analysis. Similarly, for proteomics, one device might perform a first dimension of a separation and a second device a second orthogonal separation. The ability to connect devices in a "plug-and-play" manner permits processes with different rates, cycle times, or throughputs to proceed independently. Sets of modular microchips can be prepared and incubated in hotels. When one step in a sample preparation process is complete, modular microchips for the next step can be docked, loaded, and, if necessary, moved to hotels for incubation of the next step. When sample preparation is complete, the modular microchips can interface with a high throughput CAE microchip, mass spectrometer, flow cytometer, or other analysis devices.

The modular approach lets macroscale devices such as automation and robotics work with nanoscale sample preparation and analysis. The positional accuracy necessary for modular manipulation is well within the existing capability of current robotic systems and much less than required in the microelectronics industry. Stages and stepper motors are now capable of less than 1 μm positioning and greater than 5 μm positioning is fairly routine. Modular microchips can leverage the extensive automation capabilities directly to accelerate development and deployment of nanoscale devices.

The modular microfluidic approach can combine microchip-based technologies with automation systems to create a technology platform to completely automate nanoscale sample preparation methods and link it to many types of analysis. In this instant invention, examples of how to apply the invention to develop DNA sequence sample preparation and analysis, AFLP analysis, PCR analysis, MLVA analysis, cycle sequencing, DNA fragment analysis for genotyping, and fragment analysis for DNA sequencing.

In this invention, guidance is provided on how microscale and nanoscale devices can be connected and how to perform sample preparation and analysis on microchips. We also teach how to connect different microchips that perform specialized functions comprising microchip valves, reactors, movement of fluids, mixing, performance of different biochemistries, and analysis methods.

SUMMARY OF THE INVENTION

In one aspect this invention provides a microfluidic device comprising: a microfluidic layer, an actuation layer and elastomer layer sandwiched between them, wherein: the microfluidic layer comprises at least three microfluidic channels converging at a nexus and separated by discontinuities that interrupt the flow of fluid in said at least three microfluidic channels; the actuation layer comprises at least one actuation channel opening into a valve chamber, which valve chamber is disposed opposite the nexus; and wherein displacement of said elastomeric membrane modulates fluid flow across said at least three microfluidic channels, whereby a diaphragm valve is formed. In one embodiment, the elastomeric membrane simultaneously modulates fluid flow across said at least three microfluidic channels. In another embodiment, the elastomeric membrane prevents fluid flow across said at least three microfluidic channels. In another embodiment, the elastomeric membrane incompletely inhibits fluid flow across said at least three microfluidic channels. In another embodiment, diaphragm valve further comprises a vias layer. In another embodiment, the application of pressure or a vacuum to said at least one actuation channel causes said elastomeric membrane to modulate a flow of a fluid across said discontinuities, thereby forming at least a three channel valve. In another embodiment, the membrane naturally closes the valve and application of vacuum to the membrane deflects the membrane away from a valve seat, thereby opening the valve. In another embodiment the microfluidic layer comprises a surface facing the membrane, said surface comprising a groove which, when pressed against the membrane, forms the microfluidic channel. In another embodiment, the microfluidic layer comprises an internal microfluidic channel that intersects a bore in the layer that opens onto the nexus. In another embodiment, the actuation layer comprises a surface facing the membrane, said surface comprising a groove which, when pressed against the membrane, forms the actuation channel. In another embodiment the actuation layer comprises an internal actuation channel that opens onto the valve chamber. In another embodiment, at least three microfluidic channels converge at a nexus in a Y formation. In another embodiment, a plurality of said diaphragm values is actuated by a single actuation channel.

In another aspect this invention provides a microfluidic device comprising: a microfluidic layer, an actuation layer and elastomer layer sandwiched between them, wherein: the microfluidic layer comprises first and second microfluidic channels converging at a nexus and separated by discontinuities that interrupt the flow of fluid between the first and second channels but not along the second channel; the actuation layer comprises at least one actuation channel opening into a valve chamber, which valve chamber is disposed opposite the nexus; and wherein displacement of said elastomeric membrane modulates fluid flow across said at least three microfluidic channels, whereby a diaphragm valve is formed. In one embodiment, the fluid flow in said second microfluidic channel is not modulated by said elastomeric membrane. In another embodiment, the elastomeric membrane prevents fluid flow across at least one microfluidic channel. In another embodiment, the elastomeric membrane incompletely inhibits fluid flow across at least one microfluidic channel. In another embodiment, the diaphragm valve further comprises a valve layer. In another embodiment, the application of pressure or a vacuum to said at least one actuation channel causes said elastomeric membrane to modulate a flow of a fluid across at least one discontinuation. In another embodiment, at least two microfluidic channels converge at a nexus in a T formation. In another embodiment, a plurality of the diaphragm valves are actuated by a single actuation channel. In another embodiment, the second channel forms a loop having defined volume and comprises a positive displacement pump of predetermined volume. In another embodiment, a predetermined volume of liquid is pumped into the first channel of a microstructure device by opening the diaphragm valve and performing a plurality of strokes with the pump.

In another aspect this invention provides a microfluidic device comprising: a microfluidic layer, an actuation layer and a elastomeric membrane layer sandwiched between them, wherein: the microfluidic layer comprises a microfluidic channel; the actuation layer comprises at least one actuation channel opening into a valve chamber, which valve chamber is disposed along the microfluidic channel; and wherein fluid flows along the channel whether or not the elastomeric membrane is displaced, but displacement of said elastomeric membrane modulates fluid flow along said channel, thereby forming a diaphragm valve. In one embodiment, the elastomeric membrane modulates fluid flow by increasing or decreasing the cross section of said at least one microchannel. In another embodiment, the diaphragm valve further comprises a vias layer. In another embodiment, the application of pressure or a vacuum to at least one actuation channel causes said elastomeric membrane to modulate a flow of a fluid across at least one discontinuation. In another embodiment, a microfluidic device comprising a magnet that exerts a field at a diaphragm valve is provided. In another embodiment. The magnet is selected from the group consisting of a permanent magnet, an electromagnet, and a rare earth magnet. In another embodiment, the pathway of at least one microchannel forms a star or nested star adjacent to said diaphragm valve.

In another aspect this invention provides a system comprising: a first microfluidic device comprising: a first microfluidic circuit comprising an inlet, an outlet, a pump and at least one first functional component selected from a reactor, a capture region, a temperature cycling zone, a hot zone, a cool zone, separation channel, analysis circuit, mixer, bead processing unit, and a magnet, wherein the pump is configured to pump fluid through the circuit; and a second microfluidic device comprising: a plurality of second microfluidic circuits, each comprising an inlet, and outlet and at least one functional component which is different than a first functional component; wherein the first and second components are configured to engage in a plurality of positions, wherein in each position the outlet of the first circuit is mated with the inlet of one of the second circuits to allow fluid to flow from the first circuit into the mated second circuit. In one embodiment, the first microfluidic device further comprises an electrode configured to move fluids, molecules, chemicals or particles electrically. In another embodiment, the second microfluidic device further comprises an analysis region. In another embodiment, the second microfluidic device further comprises a capture region. In another embodiment, the second microfluidic device is mobile in comparison to said first microfluidic device. In another embodiment, the fluid input of said second microfluidic device delivers fluid from said first microfluidic device to multiple microfluidic channels. In another embodiment, the fluid output of said first microfluidic device delivers fluid from multiple microfluidic channels to said fluid input of said second microfluidic device. In another embodiment, the fluids, molecules, chemicals or particles are moved electrophoretically from said fluid output of said first microfluidic device to said fluid input of said second microfluidic device.

In another aspect this invention provides a method comprising: a) performing a first operation on a first sample in the first microfluidic circuit of the first microfluidic device of originally filed claim 26; b) engaging the first and second microfluidic devices of originally filed claim 26 so that the output of the first circuit is mated with the inlet of a first of the second microfluidic circuits; c) moving the first sample after the operation from the first circuit into the first of the second circuits; d) performing a second operation on the received first sample in the first of the second circuits; e) performing the first operation on a second sample in the first microfluidic circuit; f) engaging the first and second microfluidic devices so that the output of the first circuit is mated with the inlet of a next, different one of the second microfluidic circuits; g) moving the second sample after the operation from the first circuit into the next of the second circuits; and h) performing the second operation on the first reacted sample in the first of the second circuits. In one embodiment, a method is provided comprising repeating steps e)-h) on at least one more sample in the first circuit, wherein each sample is moved into a next different one of the plurality of second circuits. In another embodiment, the first operation comprises mixing a sample with a reagent. In another embodiment, the first operation is performed in less time than the second operation.

In another aspect this invention provides a method of making a microfluidic device comprising: joining a plurality of layers to form a plurality of microchannels and diaphragm valves; wherein said plurality of layers are sandwiched together; wherein said at least two layers of said plurality of layers are selected from the group consisting of an elastomeric membrane, an actuation layer, a microfluidic layer; a valve layer, heat spreaders, a vias layer, an interface layer, and a cover layer. In one embodiment, at least one of said plurality of layers is an adhesive layer. In another embodiment, the plurality of layers is joined together by adhesive layers. In another embodiment, the plurality of layers is joined together by at least one clamp. In another embodiment, the plurality of layers are joined except at the locations s of a diaphragm valve by reducing the pressure or temperature at the valve. In another embodiment, the plurality of layers are joined except at the locations s of a diaphragm valve by selectively placing a coating at the valve. In another embodiment, the coating is removable.

In another aspect this invention provides a microfluidic device comprising: a) a microfluidic channel; b) a first temperature zone disposed along the channel having a temperature above ambient temperature; c) a second temperature zone disposed along the channel having a temperature below ambient temperature; and d) a positive displacement pump disposed along the channel and configured to pump liquid into the first and second temperature zones. In one embodiment, a microfluidic device is provided comprising a microfluidic loop that is thermally coupled to at least one temperature zone. In another embodiment, a sample in at least one microfluidic channel is pumped at least two times between at least two different temperature zones. In another embodiment, the sample is isolated from said at least one three valve pump by an immiscible fluid. In another embodiment, at least one diaphragm valve is located in a temperature zone.

In another aspect this invention provides a method of analyzing a sample comprising: heating or cooling a nucleic acid sequence in the microfluidic device of originally filed claim 41; and analyzing said nucleic acid sequence. In one embodiment, the analyzing comprises sequencing, ligation or polymerase chain reaction amplification, transcription, translation, or coupled transcription and translation. In another embodiment, the nucleic acid is selected from the group consisting of genomic DNA, mitochondrial DNA, mRNA, tRNA, rRNA, and siRNA. In another embodiment, the analyzing comprises ligation of at least one adaptor to said nucleic acid sequence. In another embodiment, the adaptor comprises a unique nucleic acid sequence identifier. In another embodiment, the unique nucleic acid sequence identifier is used as an internal quality control metric. In another embodiment, the analyzing comprises binding of a single nucleic acid sequence that has been ligated to a bead. In another embodiment, a method is provided comprising amplification of a nucleic acid sequence.

In another aspect this invention provides a microfluidic device comprising: a microfluidic layer comprising a microfluidic channel, wherein the channel comprises at least one tight bend comprising two channel segments connected with each other and oriented in an acute angle; and means for producing a magnetic field that produces a magnetic field in the area of the tight bend, wherein paramagnetic particles flowing through the tight bend are retarded by the magnetic field. In one embodiment, a microfluidic device is provided that comprises a plurality of tight bends.

In another aspect this invention provides a microfluidic device comprising: a microfluidic layer comprising a microfluidic channel, wherein the channel comprises a first, second and third regions in sequence, wherein the second region has greater cross-sectional area than the first and third regions; and means for producing a magnetic field that produces a magnetic field in the area of the second region, wherein paramagnetic particles flowing through the second region are retarded by the magnetic field. In one embodiment, In another aspect this invention provides a method of performing biomolecular analysis on a microfluidic device comprising: mixing biomolecules and reagents in a first reaction chamber on the microfluidic device to create a first reaction mixture; moving the reaction mixture to a reaction area in the device and performing a reaction to create a product mixture; moving the product mixture to an area in the device and capturing product on paramagnetic capture particles in the area; moving the particles and captured product to a capture chamber in the device that is within a magnetic field, so as to detain the capture particles and product in the capture chamber; washing the particles in the capture chamber; moving the particles and product to a port on the device wherein the product can be removed from the device. In one embodiment, the biomolecules are selected from nucleic acids (DNA or RNA), proteins, carbohydrates, cells or lipids. In another embodiment, the reaction is a nucleic acid amplification reaction. In another embodiment, the amplification is isothermal. In another embodiment, the amplification comprises thermal cycling of the mixture. In another embodiment, a method is provided comprising performing a second reaction on the reaction mixture or product mixture.

In another aspect this invention provides a microfluidic device comprising: a) a plurality of microfluidic reaction circuits, each circuit comprising: at least two ports configured to receive sample, or from which sample can be removed; at least one pump configured to pump fluid through the circuit, at least one reaction chamber comprising means for performing a chemical or biochemical reaction; and at least one capture chamber comprising means to capture particles; b) at least one dispensing port in fluidic communication with a plurality of the microfluidic circuits and configured to deliver sample or reagent fluid to each of the circuits; wherein the plurality of circuits are configured to perform operations in parallel on a plurality of different materials delivered to one of the ports in each circuit. In one embodiment, the reaction chamber is configured to be heated or cooled by a thermal pump. In another embodiment, the capture chamber is disposed in a magnetic field configured to retard the movement of paramagnetic particles in the capture chamber. In another embodiment, the pumps are positive displacement pumps.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 37 shows the layout of a mechanically clamped microchip.

FIG. 38 shows assembly of a microchip using transfer tape or adhesive coated materials.

FIG. 39 shows a microchip made from adhered layers.

FIG. 40 shows a close-up of a valve with adhered layers.

FIG. 41 shows an adhesive laminated microchip incorporating heaters and heat spreaders.

FIG. 42 shows a plastic laminated microchip with a normally closed valve that can be controlled by programmable pneumatics.

FIG. 43 shows a plastic laminated microchip with a normally open valve that can be controlled by programmable pneumatics.

FIG. 44 shows four layer valve.

FIG. 45 shows a mask design top and a plastic microchip fabricated for bead cleanup.

FIG. 46 shows the design on the top of a microchip that can fabricated in plastic or other materials and the bottom shows a photo of an acrylic microchip.

FIG. 47 shows using MOV pumps to move the sample between a hot zone and a cool zone.

FIG. 48 shows using MOV pumps are used to move the sample between three temperature zones.

FIG. 49 shows moving the sample between hot and cool zones without passing through a pump.

FIG. 50 shows increasing the throughput by using multiple samples moving between temperature zones in a multichannel thermal cycling device.

FIG. 51 shows increasing the throughput by using multiple samples moving between temperature zones in a multichannel thermal cycling device with cleanup channels.

FIG. 52 shows two-temperature cycling in two microvalves.

FIG. 53 shows three-temperature cycling in three microvalves.

FIG. 54 shows three temperature shuttle cycling in microvalves.

FIG. 55 shows a high level depiction of the workflow and processes of the NanoBioPrep SuperPyroSequencing (NanoBioPrepSPS) process.

FIG. 56 shows a NanoBioPrepSPS Ligation module for 42 ligation microchips.

FIG. 57 shows a 96 channel capillary cassette.

FIG. 58 shows two programmable microfluidic circuits for ligation.

FIG. 59 shows a microchip with 96 ligations that uses programmable microfluidic circuit.

FIG. 60 shows magnetic beads trapped in a star capture region.

FIG. 61 shows a diagram of emPCR amplification.

FIG. 64 shows thermal cycling in the emPCR module.

DETAILED DESCRIPTION OF THE INVENTION

In one aspect this invention provides guidance on the use of programmable microfluidic circuits and devices to process biochemical or chemical samples. In some embodiments microfluidic processes are connected with inputs or sample volumes of milliliter or centiliter scale. Further chemical and biochemical processes and the integration of multiple processes are disclosed. In some embodiments, microfabrication of microvalves with different designs are taught.

In certain embodiments the microfluidic devices of this invention comprise a microfluidic layer, an actuation layer and an elastomeric membrane sandwiched therebetween. The fluidics layer comprises fluidic channels adapted to allow the flow of liquid. In certain embodiments, the fluidics channels are located on the surface of the microfluidics layer that touches the elastomeric membrane. In this embodiment, an open channel, furrow or groove can be etched into the surface of the layer. In other embodiments, the channel can be internal to the layer, e.g., in the form of a tunnel, tube or via. The internal channel can access either surface of the layer through bores from the surface into the channel. In one method of making, two or more sub-layers can be effaced against one another so that at least one sub-layer comprises a groove forming the closed channel when two sub-layers are mated. In this embodiment, one of the sub-layers comprises the bores that open onto a surface, e.g., at a port or at a nexus to allow flow across a valve. Diaphragm valves of this invention displace defined volumes of liquid. When placed in a series of three, diaphragm valves can function as a diaphragm pump, which functions as a positive displacement pump. Modular devices of the invention can comprise means to move modules with respect to one another (e.g., stepper motors) so that they can engage and mate fluidic channels across the different modules, for example in sequence. This allows coordination of rapid activities with slower ones by moving the module with the rapid activity across the module with the slower activity so that the rapid module delivers sample to each of the circuits in the slower module. A first single sample can be divided between many slower channels, or a number of different samples can be delivered to each of the second circuits.

Figure 1:
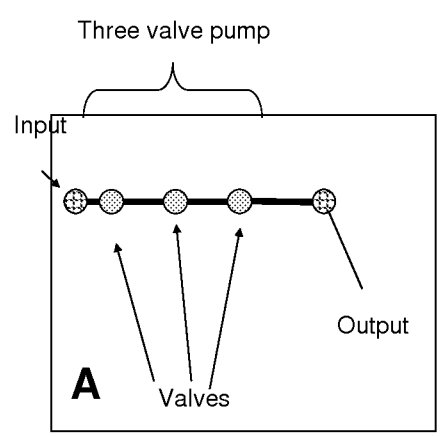
FIG. 1 shows the application of a pump on a microchip to move fluids from an input area to an output area.

In another aspect microstructures are used to move fluid on microchips. In some embodiments three or more valves can create pumps to move fluids (including but not limited to, 4, 5, 6, 7, 8, 9, 10, 11, 12, 13, 14, 15, 16, 17, 18, 19, or 20 valves). In one embodiment the valves are diaphragm valves. Diaphragm valves can be created by actuation of a deformable structure. In some embodiments a diaphragm valve comprises a valve seat. In some embodiments the diaphragm valve can allow or prevent fluid flow in a channel, such as a microchannel. In other embodiments diaphragm valves are created without a valve seat. In some embodiments the diaphragm valve can control the flow speed of a fluid through a microchannel by varying the cross-section of the channel. In another embodiment the diaphragm valve incompletely inhibits fluid flow, in other word the valve allows some fluid flow through the valve in both the open and closed positions. FIG. 1 shows the application of a pump on a microchip to move fluids from the Input area to the Output area on Microchip A.

In another embodiment the microstructures are used to move fluid which comprises analytes of interest. In one embodiment the analyte is a particle. Wherein, particles includes proteins, peptides, prions, toxins, infectious organisms (including but not limited to, bacteria, viruses, fungi), cells (including but not limited to, blood cells, white blood cells, NK cells, platelets, skin cells, cheek cells, sperm cells, trophoblasts, macrophages, granulocytes and mast cells), nucleic acids (such as DNA and RNA, including but not limited to, mRNA, rRNA, tRNA, siRNA, mitochodrial DNA, chromosomal DNA, genomic DNA, and plasmids), cell components, (including but not limited to, a nucleus, a chromosome, a ribosome, an endosome, a mitochondria, a vacuole, a chloroplast, and other cytoplasmic fragments), carbohydrates (including but not limited to, polysaccahrides, cellulose or chitin) and lipids (including, but not limited to cholesterol, triglycerides). In another embodiment the microstructures are used to move fluid which comprises analytes of interest, such as molecules or chemicals, (including but not limited to, dioxin, PCBs, heavy metals, organophosphates, estrogenic mimetics, rBST, drug metabolites, carcinogens or tetratogens)

Figure 2:
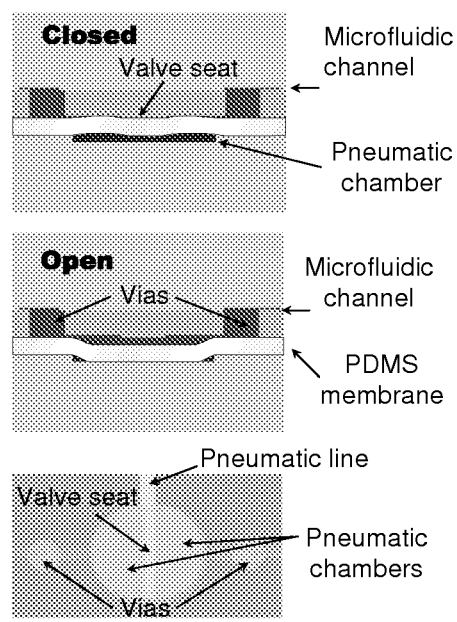
FIG. 2 shows a Microscale On-chip Valve (MOV) that is actuated by pneumatics.

In another aspect microstructures are used in sample capture and purification, such as micro-separations, microvalves, -pumps, and -routers, nanofluidic control, and nano-scale biochemistry. In one embodiment microstructures are used to miniaturize and automate complex workflows (FIG. 2). In one embodiment the Microscale On-chip Valves (MOV) valves, pumps, and routers and the instrumentation to operate them comprise a NanoBioProcessor platform. In another embodiment the microchip comprises microstructures that comprise one or more functional components, including, but not limited, to a reactor, a capture region, a temperature cycling zone, a hot zone, a cool zone, separation channel, analysis circuit, mixer, bead processing unit, a heat spreader, a pettier device, and a magnet. In some embodiments the capture zone may comprise binding moieties linked to a substrate, including, but not limited, antibodies, Fc fragments, Fab fragments, lectins, polysaccharides, receptor ligands, DNA sequences, PNA sequences, siRNA sequences, or RNA sequences. In another embodiment, one or more regions of the microstructure may comprise beads, such as magnetically responsive beads. In some embodiments the beads may comprise binding moieties, including, but not limited, antibodies, Fc fragments, Fab fragments, lectins, polysaccharides, receptor ligands, DNA sequences, PNA sequences, siRNA sequences, or RNA sequences. In some embodiments the magnetically responsive beads have dimensions smaller than 600 nm, such as 590 nm, 580 nm, 570 nm, 560 nm, 550 nm, 540 nm, 530 nm, 520 nm, 510 nm, 500 nm, 490 nm, 480 nm, 470 nm, 460 nm, 450 nm, 440 nm, 430 nm, 420 nm, 410 nm, 400 nm, 390 nm, 380 nm, 370 nm, 360 nm, 350 nm, 340 nm, 330 nm, 320 nm, 310 nm, 300 nm, 290 nm, 280 nm, 270 nm, 260 nm, 250 nm, 240 nm, 230 nm, 220 nm, 210 nm, 200 nm, 190 nm, 180 nm, 170 nm, 160 nm, 150 nm, 140 nm, 130 nm, 120 nm, 110 nm, 100 nm, 90 nm, 80 nm, 70 nm, 60 nm, 50 nm, 40 nm, 30 nm, 20 nm, or 10 nm. In some embodiments the magnetically responsive beads comprise an iron compound. In one embodiments the magnetically responsive beads is a ferrite bead.

In some embodiments, a magnetic bead has a diameter that is between 10-1000 nm, 20-800 nm, 30-600 nm, 40-400 nm, or 50-200 nm. In some embodiments, a magnetic bead has a diameter of more than 10 nm, 50 nm, 100 nm, 200 mu, 500 nm, 1000 nm, or 5000 nm. The magnetic beads can be dry or suspended in a liquid. Mixing of a fluid sample with a second liquid medium containing magnetic beads can occur by any means known in the art including those described in U.S. Ser. No. [Not Assigned], entitled "Methods and Systems for Fluid Delivery," filed Sep. 15, 2005.

In some embodiments, when an analyte in a sample (e.g., analyte of interest or not of interest) is ferromagnetic or otherwise has a magnetic property, such analyte can be separated or removed from one or more other analytes (e.g., analyte of interest or not of interest) or from a sample depleted of analytes using a magnetic field. For example, a first analyte is coupled to antibodies that specifically bind the first analyte and wherein the antibodies are also coupled to magnetic beads. When a mixture of analytes comprising the first analyte-magnetic bead complex and a second analyte are delivered into a magnetic field, the first analyte-magnetic bead complex will be captured while other cells continue to migrate through the field. The first analyte can then be released by removing the magnetic field.

The magnetic field can be external or internal to the microstructures disclosed herein. An external magnetic field is one whose source is outside a device herein (e.g., microchip, diaphragm valve, channel, obstacles) contemplated herein. An internal magnetic field is one whose source is within a device contemplated herein. In some embodiments the magnetic filed is generated by an electromagnet or a permanent magnet, such as a rare earth magnet. In some embodiments the magnet is mobile and can be moved in relation to the microstructure.

In some embodiments, when an analyte desired to be separated (e.g., analyte of interest or not of interest) is not ferromagnetic or does not have a magnetic property, a magnetic bead can be coupled to a binding moiety that selectively binds such analyte. Examples of binding moieties include, but are not limited to, lectins, polypeptides, antibodies, nucleic acids, etc. In preferred embodiments, a binding moiety is an antibody or antibody fragment (such as Fab, Fc, sfv) that selectively binds to an analyte of interest (such as a red blood cell, a cancer cell, a sperm cell, a nuclei, a chromosome, a white blood cell, an epithelial cell, a bacterium, a virus or fungi). Therefore, in some embodiments a magnetic bead may be decorated with an antibody (preferably a monoclonal antibody).

Magnetic particles may be coupled to any one or more of the microstructures disclosed herein prior to contact with a sample or may be mixed with the sample prior to delivery of the sample to the device(s).

In some embodiments, the systems herein include a reservoir containing a reagent (e.g., magnetic beads) capable of altering a magnetic property of the analytes captured or not captured. The reservoir is preferably fluidly coupled to one or more of the microstructures disclosed herein. For example, in some embodiments, a magnetic reservoir is coupled to a size-microchannel and in other embodiments a magnetic reservoir is coupled to a capture region.

The exact nature of the reagent will depend on the nature of the analyte. Exemplary reagents include agents that oxidize or reduce transition metals, reagents that oxidize or reduce hemoglobin, magnetic beads capable of binding to the analytes, or reagents that are capable of chelating, oxidizing, or otherwise binding iron, or other magnetic materials or particles. The reagent may act to alter the magnetic properties of an analyte to enable or increase its attraction to a magnetic field, to enable or increase its repulsion to a magnetic field, or to eliminate a magnetic property such that the analyte is unaffected by a magnetic field.

Any magnetic bead that responds to a magnetic field may be employed in the devices and methods of the invention. Desirable particles are those that have surface chemistry that can be chemically or physically modified, e.g., by chemical reaction, physical adsorption, entanglement, or electrostatic interaction.

In some embodiments capture moieties can be bound to magnetic beads by any means known in the art. Examples include chemical reaction, physical adsorption, entanglement, or electrostatic interaction. The capture moiety bound to a magnetic bead will depend on the nature of the analyte targeted. Examples of capture moieties include, without limitation, proteins (such as antibodies, avidin, and cell-surface receptors), charged or uncharged polymers (such as polypeptides, nucleic acids, and synthetic polymers), hydrophobic or hydrophilic polymers, small molecules (such as biotin, receptor ligands, and chelating agents), carbohydrates, and ions. Such capture moieties can be used to specifically bind cells (e.g., bacterial, pathogenic, fetal cells, fetal blood cells, sperm cells, cancer cells, and blood cells), organelles (e.g., nuclei), viruses, peptides, proteins, carbohydrates, polymers, nucleic acids, supramolecular complexes, other biological molecules (e.g., organic or inorganic molecules), small molecules, ions, or combinations (chimera) or fragments thereof.

Once a magnetic property of an analyte has been altered, it may be used to effect an isolation or enrichment of the analyte relative to other constituents of a sample. The isolation or enrichment may include positive selection by using a magnetic field to attract the desired analytes to a magnetic field, or it may employ negative selection to attract an analyte not of interest. In either case, the population of analytes containing the desired analytes may be collected for analysis or further processing.

In some embodiments the microstructures are used in a method of analysis, wherein at least one molecule, particle or chemical is analyzed. In one example a nucleic acid is analyzed. Analysis includes, but is not limited to, ligation or polymerase chain reaction amplification, transcription, translation, coupled transcription and translation.

In another example a labeled binding moiety is bound to a target analyte (such as a cell, protein, cell fragment, or nucleic acids). Wherein, the binding moiety includes, but is not limited to, an antibody, antibody fragment, receptor, receptor ligand, lectin, polysaccharide, or nucleic acid. Wherein, the label includes, but is not limited to, fluorescent labels (including, but not limited to, FITC, PE, Texas RED, Cyber Green, JOE, FAM, HEX, TAMRA, ROX, Alexa 488, Alexa 532, Alexa 546, Alexa 405 or other flurochromes), radioactive labels (including, but not limited to, $P_{32}$, $H_3$, or $C_{14}$), fluorescent proteins (including, but not limited to, GFP, RFP, or YFP), quantum dots, gold particles, sliver particles, biotin, beads (including but not limited magnetic beads or polystyrene beads).

In some embodiments MOV pumps, valves, and routers that transport, process, and enable analysis of samples are disclosed. Externally actuated, pneumatically-driven, on-chip valves, pumps, and routers) can control fluidic flow at manipulate volumes from 10 nL to 10 uL; including but not limited to 10 nl, 11 nl, 12 nl, 13 nl, 14 nl, 15 nl, 16 nl, 17 nl, 18 nl, 19 nl, 20 nl, 21 nl, 22 nl, 23 nl, 24 nl, 25 nl, 26 nl, 27 nl, 28 nl, 29 nl, 30 nl, 35 nl, 40 nl, 45 nl, 50 nl, 55 nl, 60 nl, 65 nl, 70 nl, 75 nl, 80 nl, 85 nl, 90 nl, 95 nl, 100 nl, 110 nl, 120 nl, 130 nl, 140 nl, 150 nl, 160 nl, 170 nl, 180 nl, 190 nl, 200 nl, 250 nl, 300 nl, 350 nl, 400 nl, 450 nl, 500 nl, 550 nl, 600 nl, 650 nl, 700 nl, 750 nl, 800 nl, 850 nl, 900 nl, 950 nl, 1000 nl, 1.1 ul, 1.2 ul, 1.3 ul, 1.4 ul, 1.5 ul, 1.6 ul, 1.7 ul, 1.8 ul, 1.9 ul, 2.0 ul, 2.5 ul, 3.0 ul, 3.5 ul, 4.0 ul, 4.5 ul, 5.0 ul, 5.5 ul, 6.0 ul, 6.5 ul, 7.0 ul, 7.5 ul, 8.0 ul, 8.5 ul, 9.0 ul, 9.5 ul, 10.0 ul (see, Grover, W. H. et al., 2003. Sensors and Actuators B89:315-323; U.S. patent application Ser. Nos. 10/750,533; 10/540,658; all of which are herein incorporated by reference in their entirety).

In one embodiment the MOV valves and pumps combine two glass microfluidic layers with a polydimethyl siloxane (PDMS) deformable membrane layer that opens and closes the valve, and a pneumatic layer to deform the membrane and actuate the valve (FIG. 2). The microfluidic channel etched in the top glass fluidic wafer is discontinuous and leads to vias through the "via wafer" and microfluidic channels to a valve seat which is normally closed (FIG. 2 top panel). When a vacuum is applied to the pneumatic displacement chamber by conventional-scale vacuum and pressure sources, the normally closed PDMS membrane lifts from the valve seat to open the valve (FIG. 2 middle panel). The bottom panel of FIG. 2 shows a top view of the valve as the same scale as the other panels.

Figure 3:
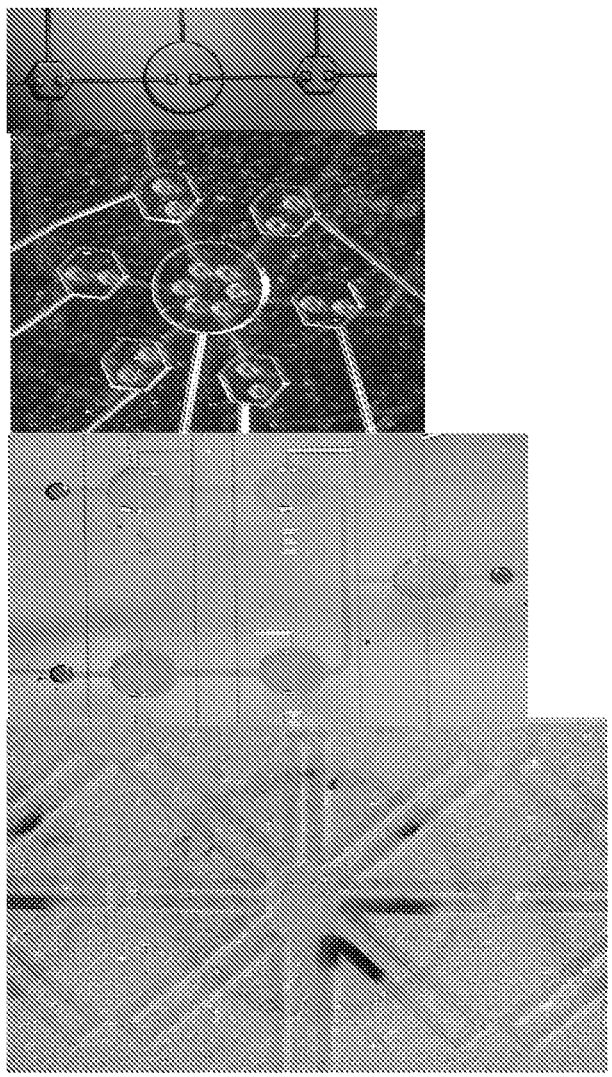
FIG. 3 shows self-priming MOV pumps in the top panel, routers in the top middle panel, mixers in the bottom middle panel, and capture of beads in channels in the bottom panel.

In another embodiment, self-priming MOV pumps (FIG. 3, top) are made by coordinating the operation of three or more valves and can create flow in either direction. In another embodiment, routers are made from three or more MOV valves (FIG. 3, top middle panel). In another embodiment, MOV mixers (FIG. 3, bottom middle panel) rapidly mix samples and reagents. In a further embodiment, MOV devices work exquisitely with magnetic beads to pump or trap sets of beads (FIG. 3, bottom panel).

The normally closed MOV valves, pumps, and routers are durable, easily fabricated at low cost, can operate in dense arrays, and have low dead volumes. Arrays of MOV valves, pumps, and routers are readily fabricated on microchips, such as NanoBioProcessor microchips. In one embodiment, all the MOV valves, pumps, and routers on a microchip are created at the same time in a simple manufacturing process using a single membrane, such as a sheet of Teflon, silicone elastomers, polydimethylsiloxane (PDMS), polyimide, Mylar, Latex, Viton, polycarbonate, acrylic, santaprene, polyurethane, or buna. This technology provides the ability to create complex micro- and nanofluidic circuits on microchips.

Figure 35:
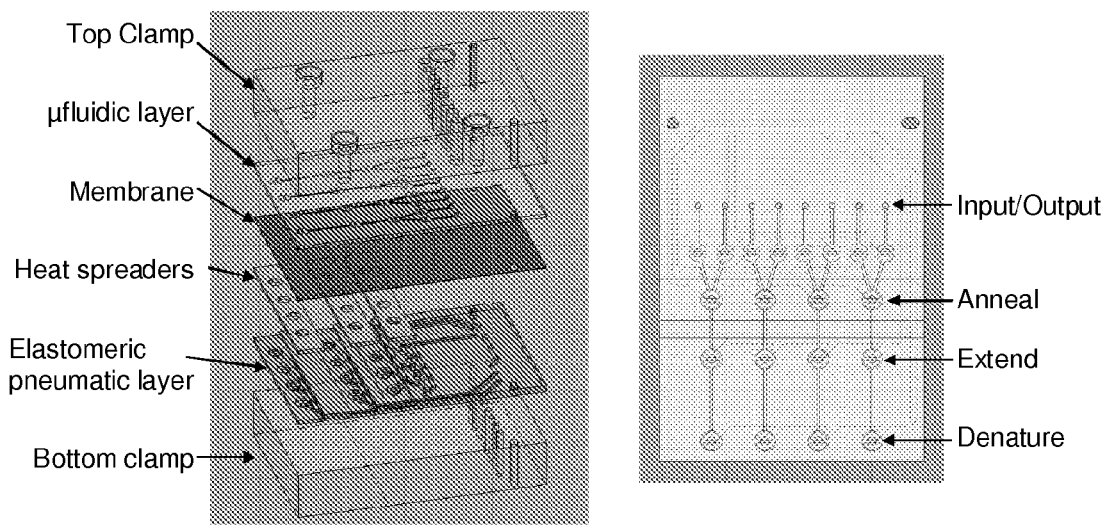
FIG. 35 shows the design of a mechanically clamped microchip.
Figure 36:
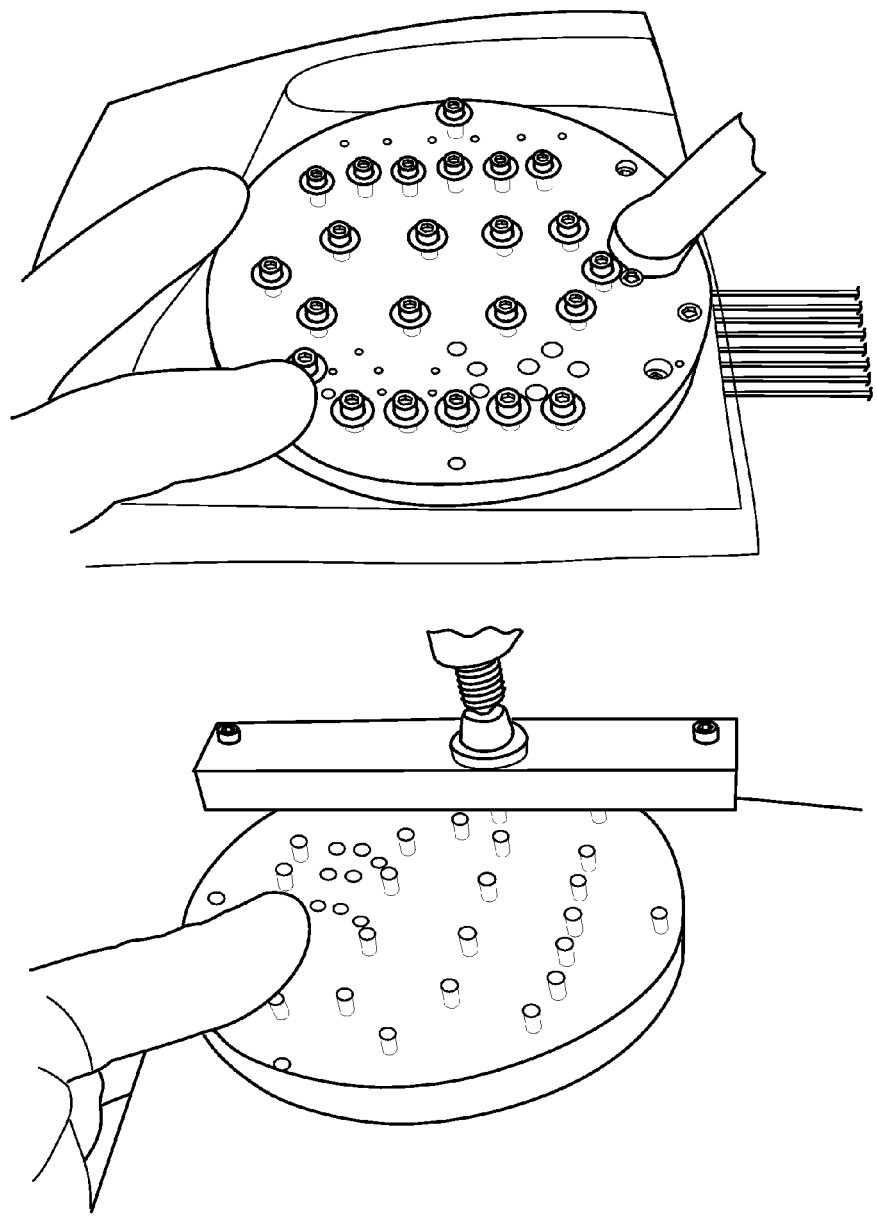
FIG. 36 shows a picture of a mechanically clamped microchip from the top in the top panel and from the bottom in the bottom panel.

In one aspect methods of manufacturing a microfludic structure are disclosed. In one embodiment the structure is manufactured by sandwiching multiple layers of material together to form a complete microfludic structure. In one embodiment these layers are joined together through the use of adhesives (FIGS. 38-41). In another embodiment the layers are joined together by at least one clamp, including but not limited to 2, 3, 4, 5, 6, 7, 8, 9, 10, 11, 12, 13, 14, 15, 16, 17, 18, 19, 20, 25, 30, 40, 45, or 50 clamps (FIGS. 35 and 36). In another embodiment the layers are joined together by a combination of adhesives and clamps or pins. In one embodiment the multiple layers of material which are sandwiched together comprise at least three layers selected from the group consisting of a top cover, microfluidics layer, a vias, an interface, a membrane, a pneumatics layer, a bottom cover, a heat spreader, a heater, an actuation layer and a valve layer. In another embodiment the layers are comprised of more than one substrate. For example, substrates that can be used to create microvalves include, but are not limited to, quartz, glass (such as borosilicate glass, include, but are not limited to, pyrex, borofloat, Corning 1737), silicon, and plastics (including, but not limited to, acrylic, polycarbonate, liquid crystal polymer, polymethylmethoxyacrylate (PMMA), Zeonor, polyolefin, polypropylene, and polythiols). In another example substrates that can be used as membranes include, but are not limited to, Teflon, silicone elastomers, polydimethylsiloxane (PDMS), polyimide, Mylar, Latex, Viton, polycarbonate, acrylic, santaprene, polyurethane, and buna. In another example substrates that can be used as adhesives include, but are not limited to, transfer tape, adhesive coated tape such as silicone based, acrylic, or other materials in thin sheets or films.

In some embodiments the microstrucure comprises multiple microchannels. In some embodiments the microchannels have the same width and depth. In other embodiments the micro channels have different widths and depths. In one embodiment a microchannel is characterized as having a channel wider than the average size of an analyte of interest in a sample delivered to the microstructure. In another embodiment a micro channel has a width equal to or larger than the largest analyte (such as the largest cell) separated from the sample. For example, in some embodiments, a microchannel in a microstructure can have a width greater than 50, 60, 70, 80, 90, 100, 110, 120, 130, 140, 150 microns. In some embodiments, a microchannel has a width of less than 100, 90, 80, 70, 60, 50, 40, 30, or 20 microns. In some embodiments a microchannel in a microstructure can have a depth greater than 50, 60, 70, 80, 90, 100, 110, 120, 130, 140, 150 microns. In some embodiments, a microchannel has a depth of less than 100, 90, 80, 70, 60, 50, 40, 30, or 20 microns. In some embodiments a microchannel has side walls that are parallel to each other. In some other embodiments a microchannel has a top and bottom that are parallel to each other. In some other embodiments a microchannel comprises regions with different cross sections. In some embodiments, a microchannel has a cross section in the shape of a cheese wedge, wherein the pointed end of the wedge is directed downstream.

In some embodiments microchannels or microstructures are etched as grooves or trenches into a substrate. In some embodiments holes may be drilled, bored, cut or etched through a substrate. In other embodiments microchannels are formed in a substrate as a tunnel or a bore that is enclosed within the substrate of a single layer of a microchip.

In some embodiments microstructures are formed using standard photolithography. For example, photolithography can be used to create a photoresist pattern of obstacles on a silicon-on-insulator (SOI) wafer. A SOI wafer consists of a 100 μm thick Si(100) layer atop a 1 μm thick SiO$_2$ layer on a 500 μm thick Si(100) wafer. To optimize photoresist adhesion, the SOI wafers may be exposed to high-temperature vapors of hexamethyldisilazane prior to photoresist coating. UV-sensitive photoresist is spin coated on the wafer, baked for 30 minutes at 90° C., exposed to UV light for 300 seconds through a chrome contact mask, developed for 5 minutes in developer, and post-baked for 30 minutes at 90° C. The process parameters may be altered depending on the nature and thickness of the photoresist. The pattern of the contact chrome mask is transferred to the photoresist and determines the geometry of the microstructures.

Upon the formation of the photoresist pattern that is the same as that of the microstructures, the etching is initiated. $SiO_2$ may serve as a stopper to the etching process. The etching may also be controlled to stop at a given depth without the use of a stopper layer. The photoresist pattern is transferred to the 100 μm thick Si layer in a plasma etcher. Multiplexed deep etching may be utilized to achieve uniform microstructures. For example, the substrate is exposed for 15 seconds to a fluorine-rich plasma flowing $SF_6$, and then the system is switched to a fluorocarbon-rich plasma flowing only $C_4F_8$ for 10 seconds, which coats all surfaces with a protective film. In the subsequent etching cycle, the exposure to ion bombardment clears the polymer preferentially from horizontal surfaces and the cycle is repeated multiple times until, e.g., the $SiO_2$ layer is reached.

To couple a binding moiety to the surfaces of the obstacles, the substrate may be exposed to an oxygen plasma prior to surface modification to create a silicon dioxide layer, to which binding moieties may be attached. The substrate may then be rinsed twice in distilled, deionized water and allowed to air dry. Silane immobilization onto exposed glass is performed by immersing samples for 30 seconds in freshly prepared, 2% v/v solution of 3-[(2-aminoethyl)amino] propyltrimethoxysilane in water followed by further washing in distilled, deionized water. The substrate is then dried in nitrogen gas and baked. Next, the substrate is immersed in 2.5% v/v solution of glutaraldehyde in phosphate buffered saline for 1 hour at ambient temperature. The substrate is then rinsed again, and immersed in a solution of 0.5 mg/mL binding moiety, e.g., anti-CD71, in distilled, deionized water for 15 minutes at ambient temperature to couple the binding agent to the obstacles. The substrate is then rinsed twice in distilled, deionized water, and soaked overnight in 70% ethanol for sterilization.

There are multiple techniques other than the method described above by which binding moieties may be immobilized onto regions of the microstructures and the surfaces of the device. Simply physio-absorption onto the surface may be the choice for simplicity and cost. Another approach may use self-assembled monolayers (e.g., thiols on gold) that are functionalized with various binding moieties. Additional methods may be used depending on the binding moieties being bound and the material used to fabricate the device. Surface modification methods are known in the art. In addition, certain cells may preferentially bind to the unaltered surface of a material. For example, some cells may bind preferentially to positively charged, negatively charged, or hydrophobic surfaces or to chemical groups present in certain polymers.

The microstructure device may be made out of different materials including, but not limited to, pyrex, borofloat, Corning 1737, silicon acrylic, polycarbonate, liquid crystal polymer, polymethylmethoxyacrylate (PMMA), Zeonor, polyolefin, polystyrene, polypropylene, and polythiols. Depending on the choice of the material different fabrication techniques may also be used. The device may be made out of plastic, such as polystyrene, using a hot embossing technique. The obstacles and the necessary other structures are embossed into the plastic to create the bottom surface. A top layer may then be bonded to the bottom layer. Injection molding is another approach that can be used to create such a device. Soft lithography may also be utilized to create either a whole chamber out of plastic or only partial microstructures may be created, and then bonded to a glass substrate to create the closed chamber. Yet another approach involves the use of epoxy casting techniques to create the obstacles through the use of UV or temperature curable epoxy on a master that has the negative replica of the intended structure. Laser or other types of micromachining approaches may also be utilized to create the flow chamber. Other suitable polymers that may be used in the fabrication of the device are polycarbonate, polyethylene, and poly(methyl methacrylate). In addition, metals like steel and nickel may also be used to fabricate the device of the invention, e.g., by traditional metal machining. Three-dimensional fabrication techniques (e.g., stereolithography) may be employed to fabricate a device in one piece. Other methods for fabrication are known in the art.

Mixing Fluids

Figure 4:
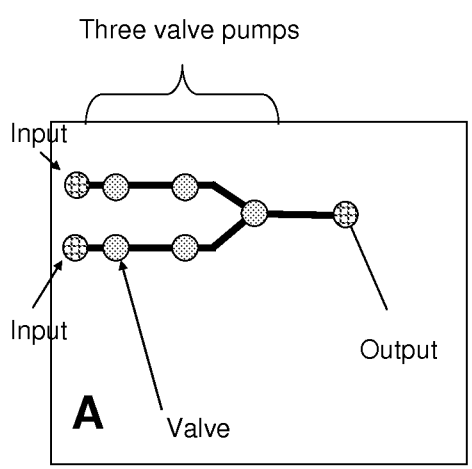
FIG. 4 shows the application of using five valves to make a fluidic circuit with two pumps on a microchip sharing a common valve.

The ability to mix fluids on microchips and capillaries is disclosed. FIG. 4 shows the application of using five valves to make a fluidic circuit with two pumps on a microchip sharing a common valve. The terms fluidics includes without limitation to connote simple liquids with only one component, mixtures, liquids containing beads, particles, gels, and other materials well known to one skilled in the art, gases, and other matrices. The circuit can move fluids from two Input area, mix them and deliver the mixture to the Output area on Microchip A. The individual fluid streams can be moved by pumps comprising three or more valves including MOV valves or other valves. The streams can contain samples, reagents, buffers, and other components. The valves can be created actuation of a deformable structure, changes in temperature, pressure. Two (FIG. 3, bottom middle panel) or more streams (FIG. 3, upper middle panel) can be combined using MOV and other microvalves. In one embodiment the MOV valves are self priming and are under computer control, they may be driven in either direction and the same circuit can be used to split a sample into two streams by simply running the two co joined pumps to move samples from the area labeled Output to the two areas labeled Input.

Figure 5:
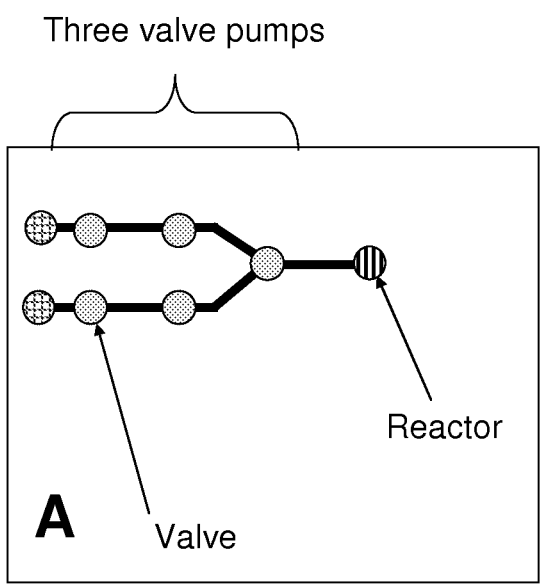
FIG. 5 shows a programmable microfluidic circuit mixing two fluid streams on a microchip and movement to a reactor.

FIG. 5 illustrates mixing two fluid streams on a microchip and movement to a reactor. In some embodiments the reactor could be located in a MOV valve to improve optical path lengths for detection, the surface-to-volume ratio, thermal control, and other advantages. In the examples that follow, additional methods to perform reactions with microchips with microvalves such as MOV valves, pumps, and routers are disclosed.

Figure 6:
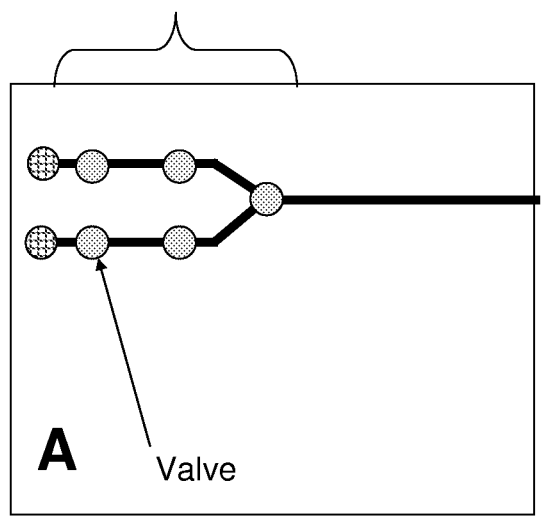
FIG. 6 shows a programmable microfluidic circuit mixing of two streams and moving the mixed stream to an edge where it might be coupled to another process.

FIG. 6 illustrates the mixing of two streams, and moving the mixed stream to an edge where it may be coupled to another process. The mixing may be done with MOV valves.

Figure 7:
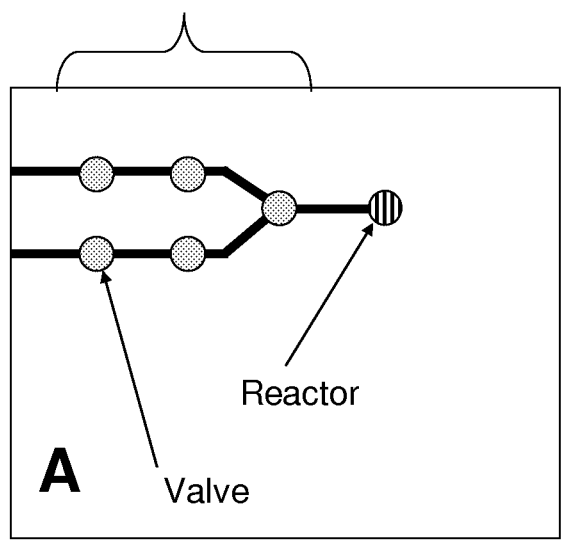
FIG. 7 shows a programmable microfluidic circuit inputting samples from an edge, combining the samples as the stream are brought together in a microvalve, and moving them to a reactor which could be a MOV valve.

FIG. 7 illustrates inputting samples from an edge, combining the samples as the stream are brought together in a microvalve, and moving them to a reactor which could be a MOV valve or a chamber created using the deflection of a membrane, for example an elastomeric membrane such as polydimethylsiloxane (PDMS).

Figure 8:
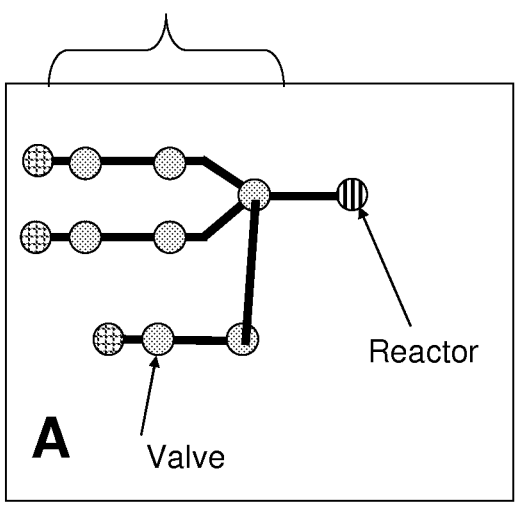
FIG. 8 shows a programmable microfluidic circuit mixing and loading a reactor connected to the edge

Three or more streams can also be combined with a MOV valve, (FIG. 3, upper middle panel), and moved into a reactor (FIG. 8). The streams can contain liquids, particles, magnetic beads, nanoparticles, colloids, gases, and other material. The MOV valves enable facile manipulation of magnetic and other beads and particles as well as fluids.

Reactions on Microchips

In one aspect a sample can be moved to a reactor, FIG. 8, comprised of an etched channel, a microvalve, a vial, flows cell, a capillary, reservoir, or other structures well known to one skilled in the art. MOV valves can be used to create microchips which combine two or more streams to perform different biochemistries. The sample can then be interrogated in the reactor. This can include, but is not limited to, optical sensing such as LIF, absorbance, chemiluminescence, surface plasmon resonance.

Figure 9:
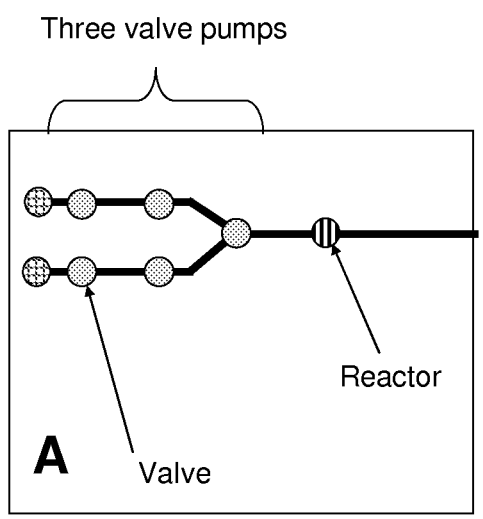
FIG. 9 shows a programmable microfluidic circuit that can move samples from two chambers to a reactor and then move the samples or product to an edge for further processing or analysis.

FIG. 9 illustrates the use of two ganged pumps to move samples to a reactor and then further move the sample or product to an edge for further processing or analysis as will be enabled below. The term sample includes, but is not limited, a fluid comprising an analyte of interest, a material comprised of a single compound or element, a complex sample such as bodily fluids, aerosols, mixtures, biological or chemical materials, including DNA, RNA, microRNAs, proteins, lipids, polysaccharides, cell walls, small molecules, and all other biological components of a biological sample, fluids comprising microbeads or particles. Further, a sample may be combined with one or more reagents prior to delivery to the microstructure.

Figure 10:
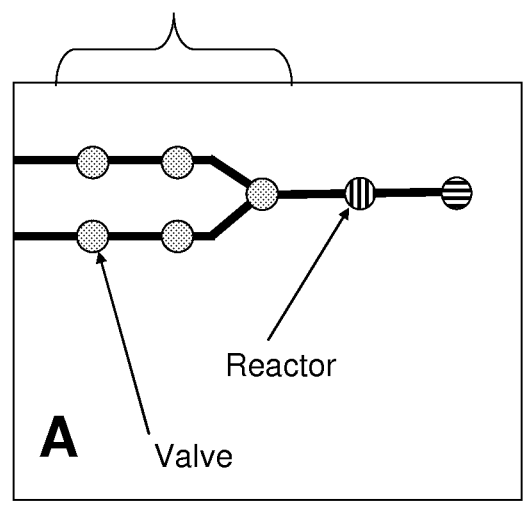
FIG. 10 shows programmable microfluidic circuit moving the sample from the reactor to a location where a second process might occur such as another biochemical or chemical reaction.

FIG. 10 illustrates moving two samples from an edge to a reactor and then to a location where a second process can occur, such as another biochemical or chemical reaction. The location can also be used to output a sample using a microfluidic device to move the sample to a robot to pipette or other mechanisms. Beads including magnetic beads can be used to move the sample when desired.

Integration of Two or More Processes

Figure 11:
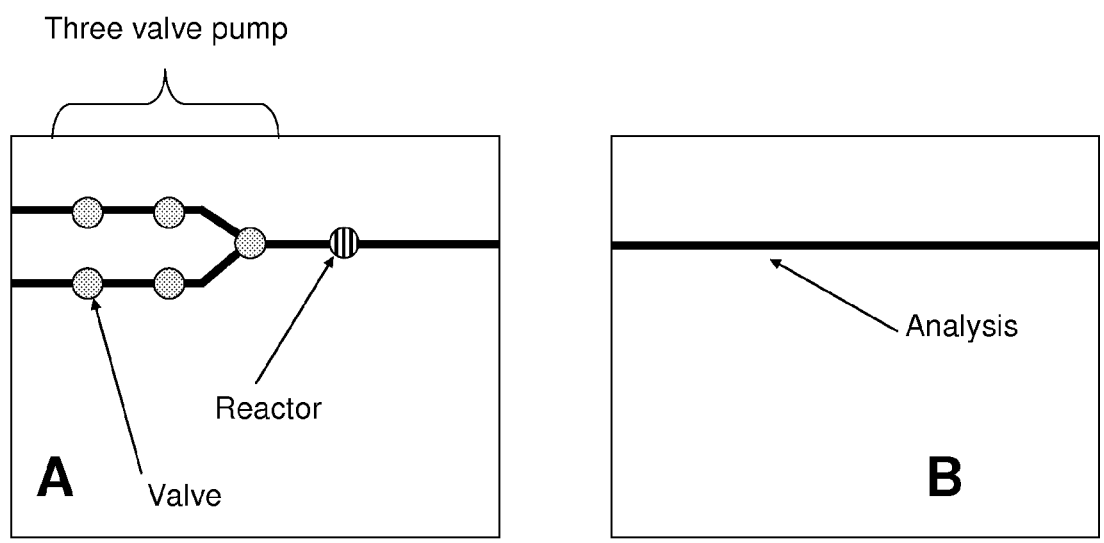
FIG. 11 shows two devices where different functions are performed on each device.

In another aspect, modular microfluidic docking and undocking are extended to use two or more processes where one or more microchips incorporate MOV valves, pumps, and routers. FIG. 11 shows one embodiment where Device A prepares samples which are then analyzed on Device B. In one embodiment the devices may be microchips or full scale devices using tubing, plumbing, or other means to prepare samples. In another preferred embodiment, Device B may be a capillary, a separate instrument comprising a capillary electrophoresis system or microchip capillary electrophoresis; multidimensional gel and capillary electrophoresis; mass spectroscopy, multidimensional mass spectroscopy with HPLC, ICP, Raman spectroscopy, particle, nanoparticles, and bead based detection, imaging, comprising fluorescence, IR, optical, or any other analytical systems well know to one in the art. The streams or fluids can be placed in reservoirs as in FIG. 6 before processing on Device A or come from the sides or other geometries as shown in FIG. 11. In this manner, a microchip, microchip A, with sample preparation functions such as reactions, routers, sample cleanup, may be used to prepare samples by many means including PCR, cycle sequencing, sandwich assays, isothermal nucleic acid amplifications, isotachaphoresis, isoelectric focusing, hybridization, affinity capture, or other methods well known to one skilled in the art. The sample can then be moved to Device B which can be a microchip, mass spectrometer, analytical instrument, or other detector including separation devices where the prepared sample may be analyzed.

Figure 12:
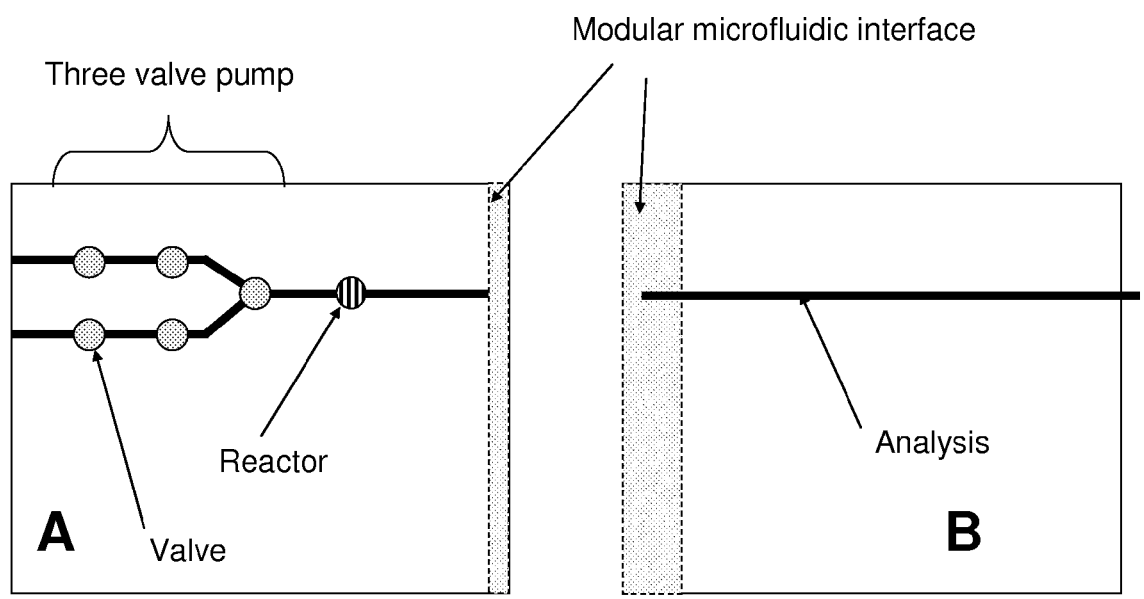
FIG. 12 shows where the analysis device may be coupled to the sample preparation microchip with modular microfluidic connections.

FIG. 12 illustrates where the analysis device may be coupled to a sample preparation microchip with modular microfluidic connections. A sample can then be moved from Device A to Device B by MOV pumps, external pressure pumps, electroosmotic flow, magnetic separations, or other methods.

Figure 13:
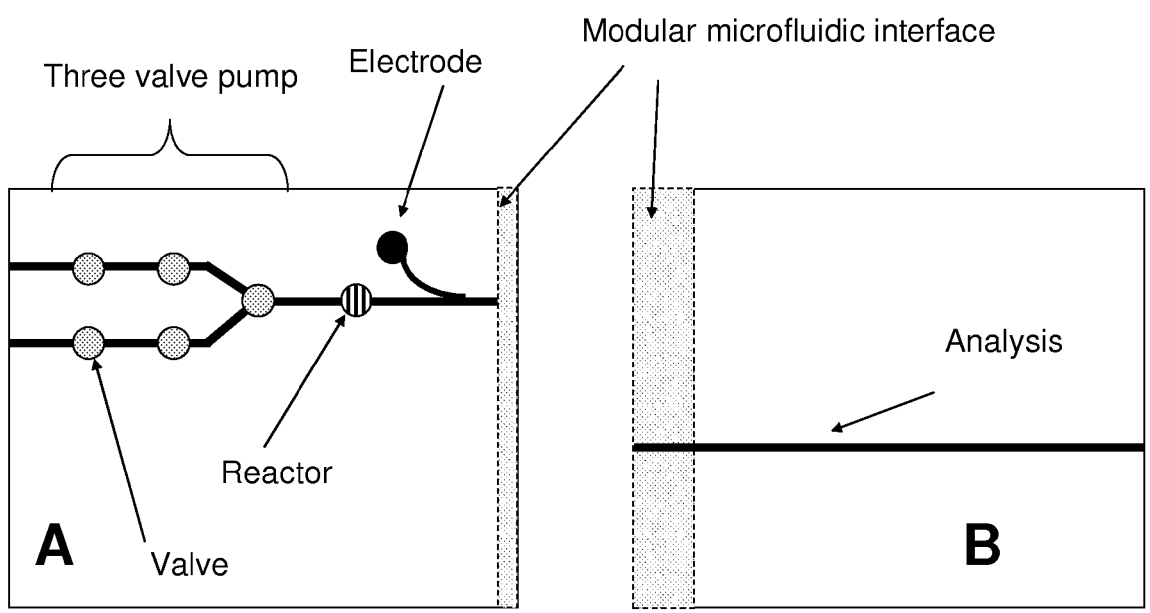
FIG. 13 shows microchips using modular microfluidic connections with one or both microchips having electrodes.

In one embodiment an electrode can be incorporated to move the sample by electrical potential, such as electrophoresis. FIG. 13 shows one configuration. In one embodiment an analyte of interest is moved in a first direction. In another embodiment an analyte not of interest is moved in a second direction. In some embodiments multiple electrodes can be used. In one example, a sample may be processed in a reactor and then pumped to the region where an electrical potential can move the sample from a device A into an analysis device B. This can occur when the two devices are moved to a proximal location which may include direct physical contact, close contact with a small gap, or further distant contact separated by a connector or interface. The circuit can be completed by use of one or more electrodes on Device B to produce an electrical field that moves the sample or components of the sample into Device B. In another embodiment additional electrodes are present in a downstream device that Device B is attached to. In another embodiment one or more electrodes are present in a reservoir that connects to Device B (FIG. 13).

Figure 14:
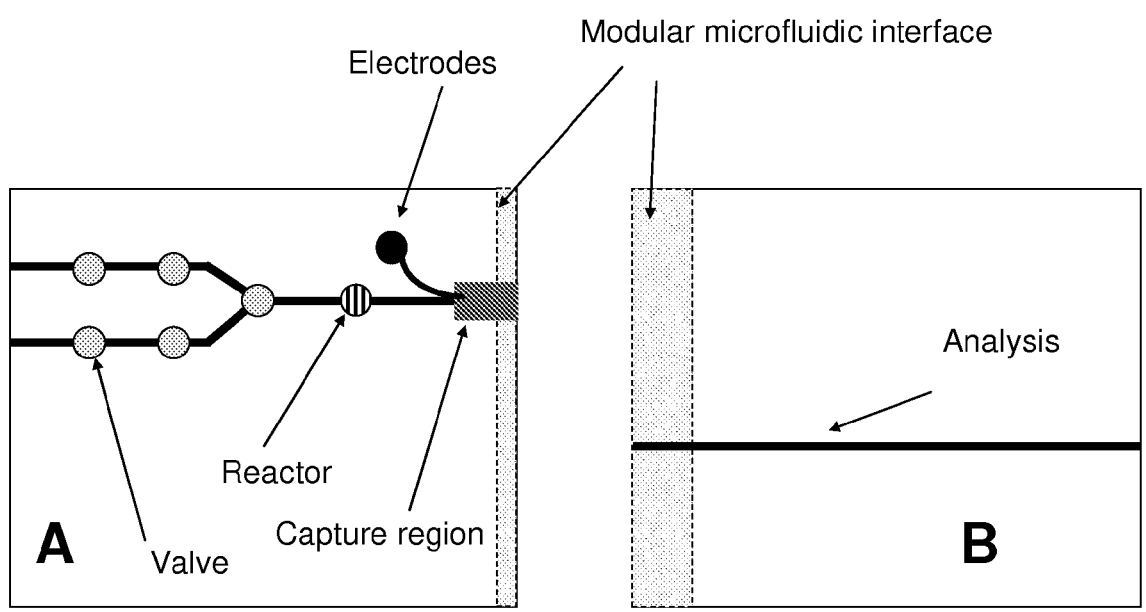
FIG. 14 shows having a capture region on one device to concentrate, purify, or capture a sample in a region and transfer it to a second device.

In another embodiment a sample can also be moved using MOV micropumps or other means to a capture region which may have capture moieties or binding moieties attached. In some embodiment the capture region can be used in a method such as hybridization, affinity capture, or other methods known to one skilled in the art. In another embodiment the capture region may comprise a non-specific capture means such as hydrophobic or hydrophilic properties, solid phase extraction, metal binding, adsorption, non-covalent interactions, covalent, light induced binding or other means to capture an analyte of interest or not of interest (FIG. 14). In one embodiment microchip A and Device B can be moved together as by modular microfluidics. In one embodiment the capture region can be used as a region for injection into an analytic device comprised as a capillary electrophoresis (CE) instrument, microchip with CE, capillary array electrophoresis (CAE). The microchip A can then be moved adjacent to microchip B which can have functions, including, but not limited to, capillary array electrophoresis (CAE), mass spectrometry, HPLC, PCR, isothermal nucleic acid amplifications, isotachaphoresis, isoelectric focusing, hybridization, affinity capture. In another embodiment the capture region can be used to concentrate the sample or purify the sample before movement to a second device which may perform additional sample preparation or analysis.

Figure 15:
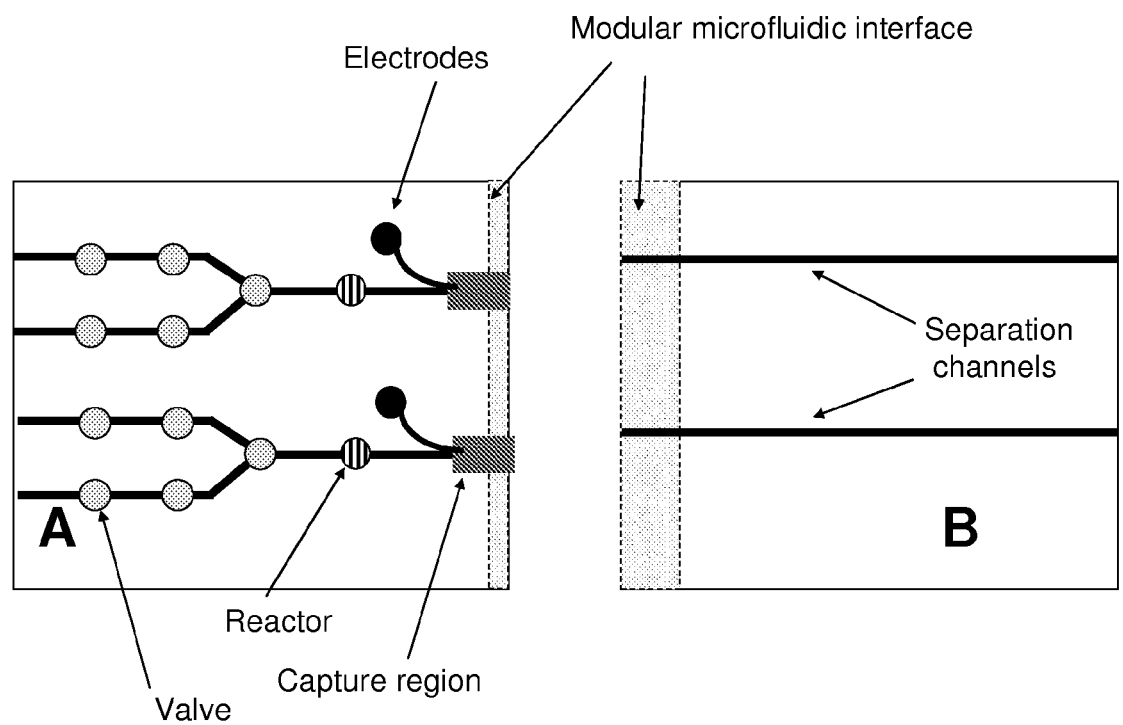
FIG. 15 shows two channels each with a capture region.
Figure 16:
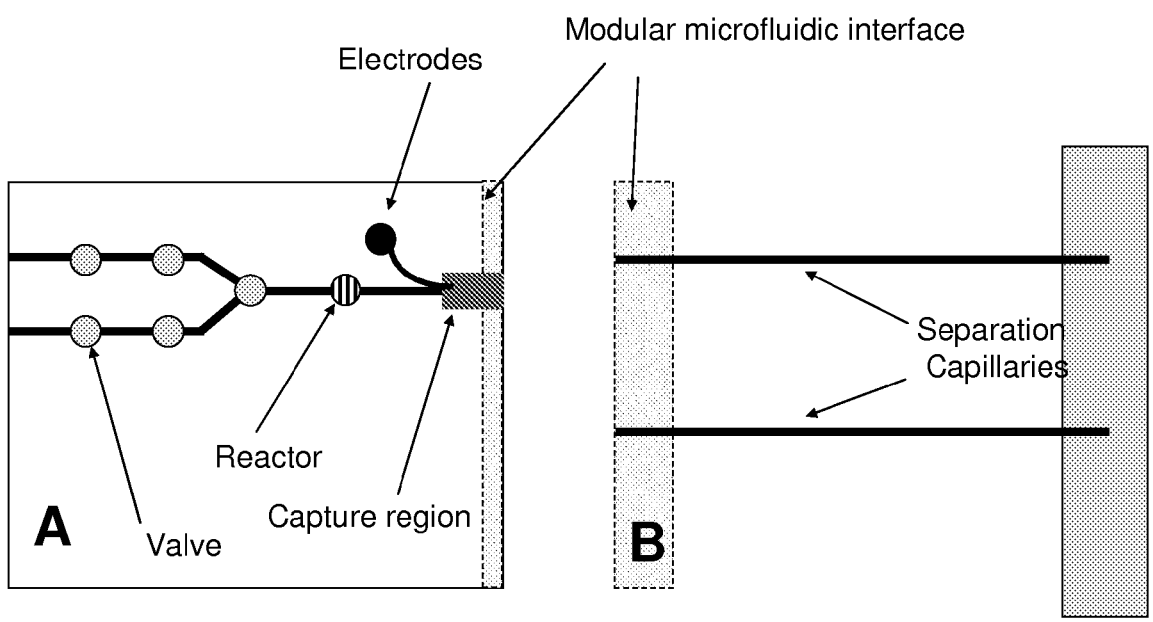
FIG. 16 shows a device A with a capture region connected to a device B with multiple analysis channels.

In one example, two devices, such as microchips, are brought either in contact or close to each other. FIG. 15 shows two channels each with a capture region. The channels can then move the samples close to device B. An electrical potential can then be applied to move the sample from the region for injection into device B. With sufficient voltage the sample can 'hop' across a gap. The sample will be quantitatively injected onto device B if so desired. The number of channels can be adjusted such that device A could have many more channels than device B and do repeated injections or device A could have fewer channels than device B. In a preferred embodiment, Device B is a microchip containing separation channels for CAE. In one embodiment Device B could comprise separation capillaries that in one embodiment might be connected through a modular microfluidic interfaces. For a 2D separation, where the first dimension was an isoelectric focusing in Device A, Device B may be repeatedly moved and a portion of a sample in microchip A can be injected into multiple microchannels on microchip B. FIG. 16 illustrates a device A with a capture region connected to a device B with multiple microchannels, which can be used for analyte analysis, such as CAE, mass spectroscopy, HPLC.

In one embodiment injection of samples into a microchip uses a "Twin T" injector. While the Twin T defines a small plug between the Twin Ts, as the sample is moved across the Twin T, a separation may occur as a sample is electrophoresed from a sample reservoir to the waste. (Liu S, Ren H, Gao Q, Roach D J, Loder R T Jr, Armstrong T M, Mao Q, Blaga I, Barker D L, Jovanovich S B. Automated parallel DNA sequencing on multiple channel microchips. Proc Natl Acad Sci USA. 2000 May 9; 97(10):5369-74.).

In another embodiment a separation channel is fabricated in one device while the injector is fabricated on a second device. In some embodiments, the two devices can be docked or undocked.

Figure 17:
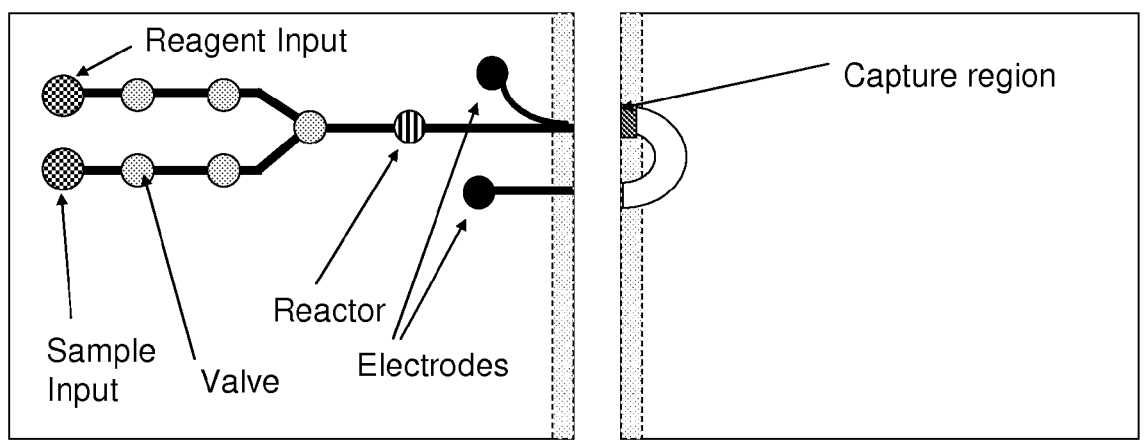
FIG. 17 shows a device with multiple electrodes connect to a device with a capture region.
Figure 18:
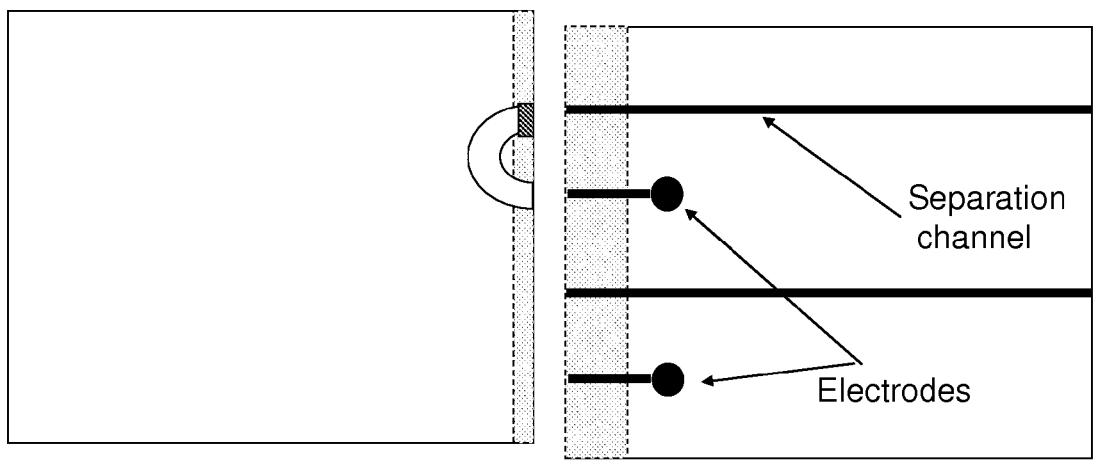
FIG. 18 shows connecting the device in FIG. 17 with a device with two or more separation channels.

In one embodiment, a sample is moved to a capture region on a separate capillary, microchip or other device. FIG. 17 shows a device which may be a microchip on the right with a capture region. A sample can be moved using first pumping by MOV valves and then electrical field to remove uncaptured analytes and purify the sample. In one embodiment a microchip with the capture region is then moved to a separation device as shown in FIG. 18, the complete sample can then be injected after desorption. The desorption might be by changing the temperature, chemical means, light desorption, or other methods well known to one skilled in the art.

Integration of Processes on Microchip for Sample Preparation and Cleanup

Figure 19:
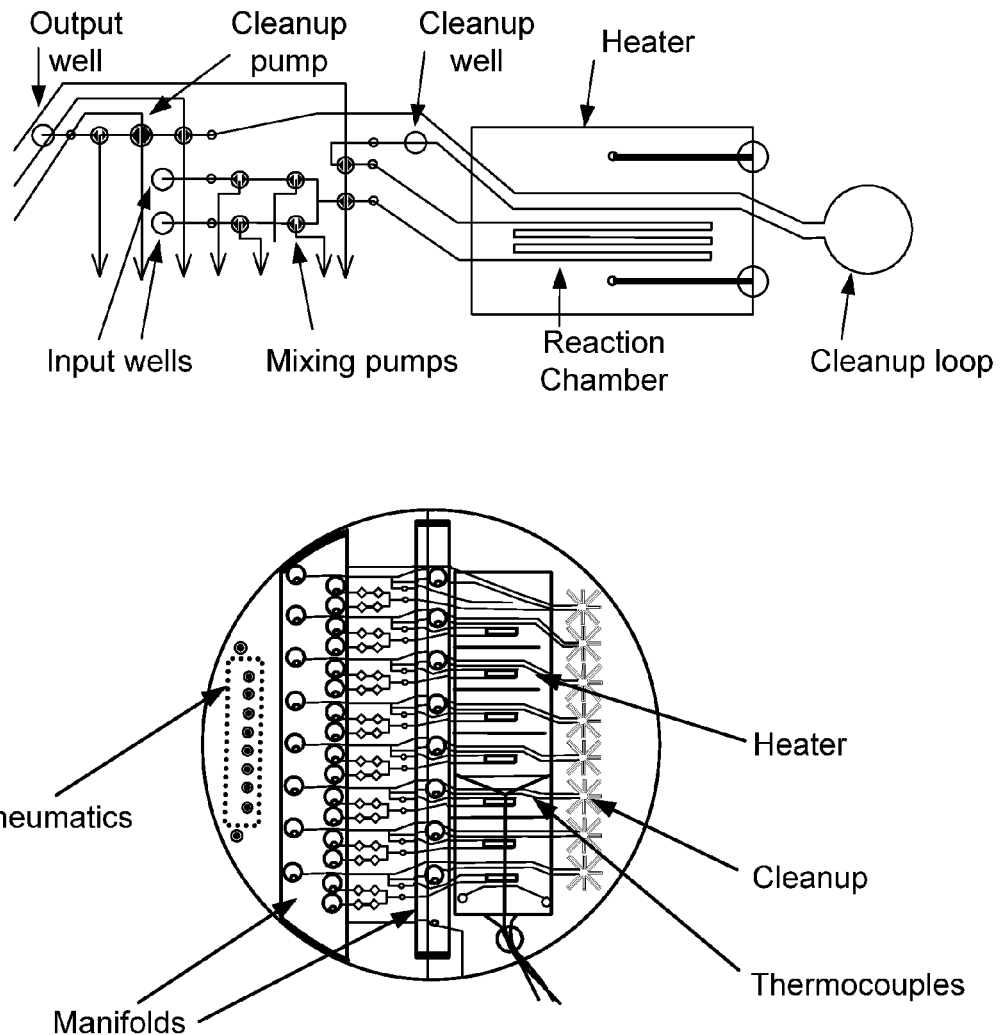
FIG. 19 shows in the top panel one circuit of an 8 channel circuit on a MBI-026 microchip which includes MOV-based mixing, a thermal cycling reaction, and bead-based sample cleanup; and in the bottom panel the completed glass MBI-026 microchip.
Figure 20:
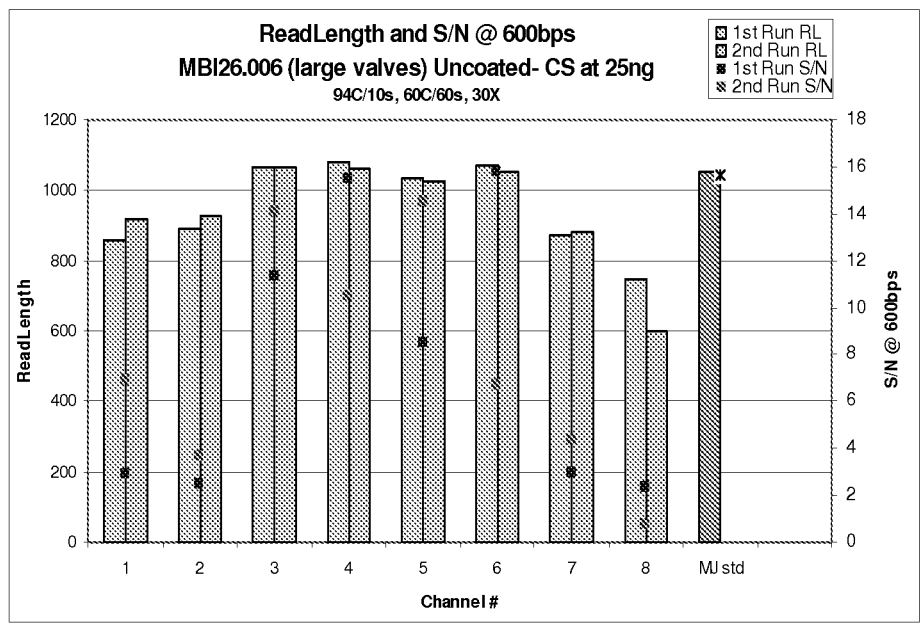
FIG. 20 shows the readlength and signal to noise from the MBI-026 microchip.

In one aspect MOV technology can be applied to microchip-based sample preparation and analysis for many fields such as DNA sequencing, biodefense, forensics, proteomics and cell biology. In one embodiment MOVE technology can be used to perform automated cycle nucleic acid sequencing and cleanup, such as Sanger sequencing. FIG. 19, top panel, illustrates one circuit of an 8 channel circuit on a MBI-026 microchip which includes MOV-based mixing, a thermal cycling reaction, and bead-based sample cleanup; the completed glass microchip is shown in the bottom panel. The MBI-026 has been used to demonstrate readlengths of over (FIG. 20) 1,000 bases of Phred 15 data on a modified MegaBACE DNA Analysis instrument using on-chip integrated cycle sequencing and cleanup to prepare Ready-to-Inject™ sequencing samples. By using PowerPlex 16 STR reactions on the MBI-026 microchip MBI has demonstrated 16-plex STR PCR amplification for forensics. Many of the elements, i.e. MOV mixer, pumps, and valves, of the MBI-026 microchip can be used in a wide range of applications.

Figure 21:
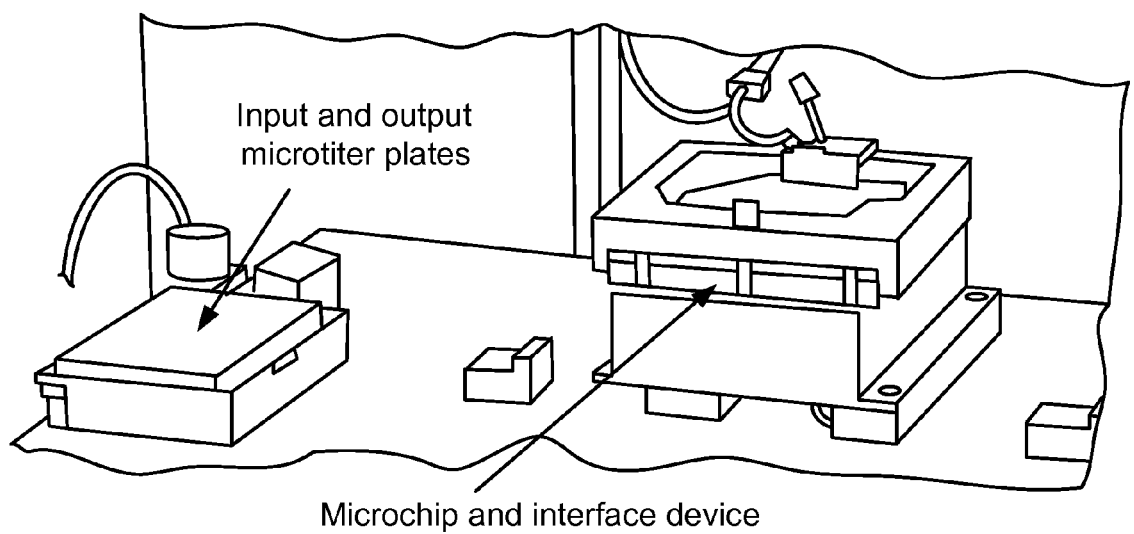
FIG. 21 shows automating microchips with microtiter plates.

In one aspect the operation of the MBI-026 microchip using NanoBioProcessor technology can be automated using one or more robots (FIG. 21). In one embodiment a robot under software control moves samples using either fixed tip or probes from a microtiter plate to a microchip (such as MBI-026) that is contained in an interface device. In one embodiment a microchip interfaces with a device that can contain functions to heat and cool the microchip. The heating device can comprise resistive heaters attached to the microchip, as shown in FIG. 19. In other embodiments the microchip is heated using resistive heaters located off the microchip, by using air or gases of different temperatures, by using infrared heating, Peltier/thermoelectric heating, contact with fluidics of different temperatures, or other means. In some embodiments the microchip is cooled by using air or other gases (such as refrigerants), Peltier devices, contact with liquids (such as refrigerants), or other means well known to one skilled in the art.

Interface with Large Volume Samples

In one aspect microfluidic devices, such as microchips are connected either directly or indirectly to devices that prepare a sample for the microfluidic device. The sample may be concentrated and/or purified.

Figure 22:
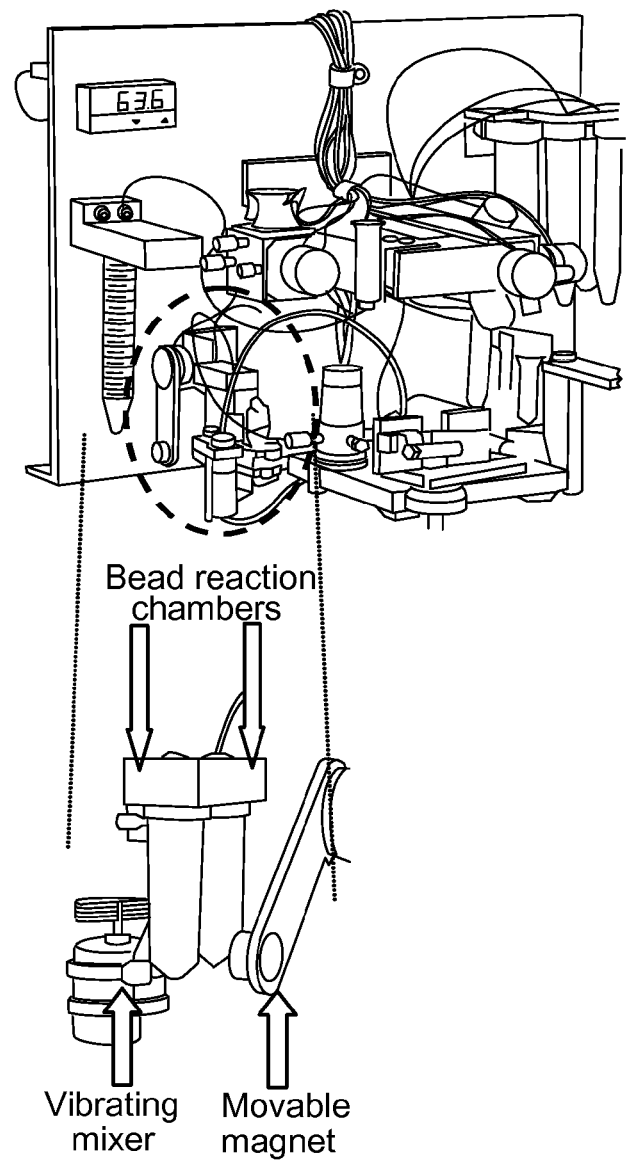
FIG. 22 shows a device, the Sample Capture and Purification Module (SCPM) that uses immunomagnetic separations (IMS) and pressure-driven flow to dispense magnetic beads, concentrate and purify bioagents onto beads.

In one embodiment, environmental aerosols are processed using fluidics to prepare samples for further microchip sample preparation and analysis. FIG. 22 shows a device, the Sample Capture and Purification Module (SCPM) that uses immunomagnetic separations (IMS) and pressure-driven flow to dispense magnetic beads, concentrate and purify bioagents onto beads. In one embodiment a prepared sample may be eluted from the beads and the eluate moved to a downstream device such as a microchip or the beads may be moved to the downstream device. In one embodiment, the beads may be introduced into microchips for miniaturized Real-Time PCR and/or microscale capillary array electrophoresis (μCAE). In some embodiments a vibrating mixer which can vibrate to mix the samples, reagents and beads can be used with a microchip (FIG. 22). In another embodiment an actuation moves magnet to trap and release magnetic beads (such as paramagnetic beads) in a microstructure.

In one embodiment hardware can be operated by software such as MBI's DevLink™ software or embedded software. DevLink defines a set of communication and command protocols in a standardized automation architecture that is simpler, more flexible, and quicker to implement than other software development approaches. The DevLink implementation framework is based on core technologies that span multiple operating systems, development languages, and communication protocols. Software drivers wrap individual smart components of the system, greatly reducing the time needed for typical de novo system software development. Integrating the operation of multiple system modules (pumps, valves, temperature controllers, I/O controllers, etc.) that are either COM- or .NET-based is straightforward. DevLink provides a professional quality software development system for prototyping through product release and maintenance.

Y-valve

Figure 23:
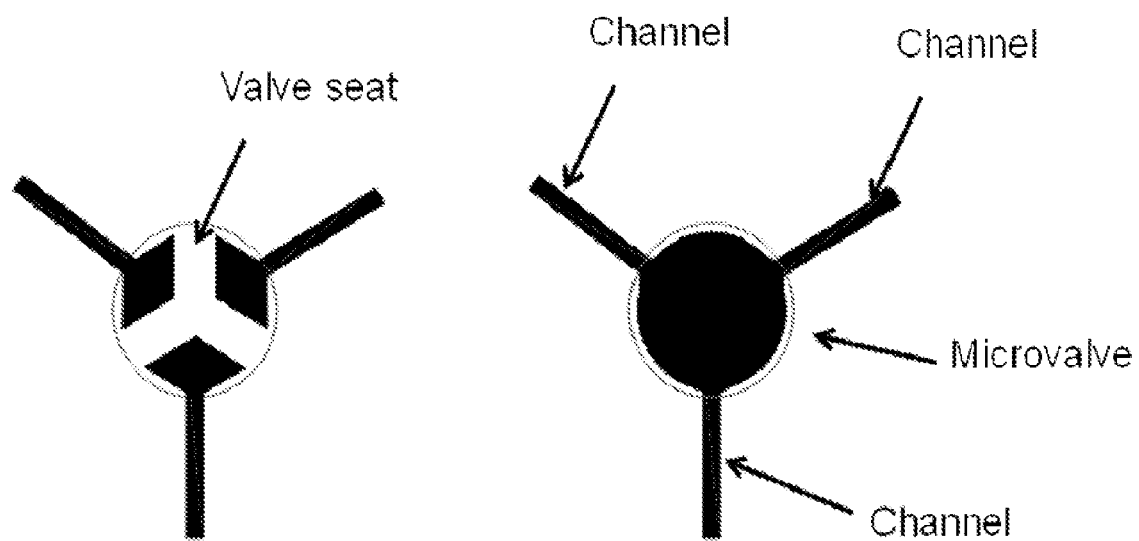
FIG. 23 shows an improved method of construction of a MOV microvalve, termed a 'Y-valve,' that has three connections.

In another aspect, MOV technology can be used to create valves that route fluid from three or more microchannels. In one embodiment a router can use a microvalve with or without a valve seat. FIG. 23 illustrates a method of construction of a MOV microvalve, termed a 'Y-valve,' that has three connections. FIG. 23 shows fluids represented by black and a valve seat represented by the white color. The valve seat may be fabricated by many methods well known to one skilled in the art comprised of photolithography, embossing, injection molding, and other microfabrication methods. When the Y-valve is in the closed position, the valve seat segregates the three channels that intersect within the valve. When open, the three channels in this drawing are allowed to communicate with one another. The volume of the valve chamber increases when the valve is open and decreases when closed. This change in volume causes movement in the liquids aiding in the mixing of liquids that come together in this valve. In the embodiment shown in FIG. 23, there can be two inlet channels where liquids are brought in and one outlet channel or one inlet and two outlets.

Flow-Through Valve

In another aspect a MOV valve as illustrated in FIG. 2 can be adapted to be a flow-through valve where two or more liquids come together. The flow-through valve in FIG. 24, termed a 'T-valve,' when closed, as shown in the left panel, allows for fluid to pass from the top to bottom through the vertical channel in this example while isolating the horizontal channel. When the valve is open as shown of the right panel of FIG. 24, fluid can be moved from the vertical channel to the horizontal or from the horizontal to the vertical.

Figure 25:
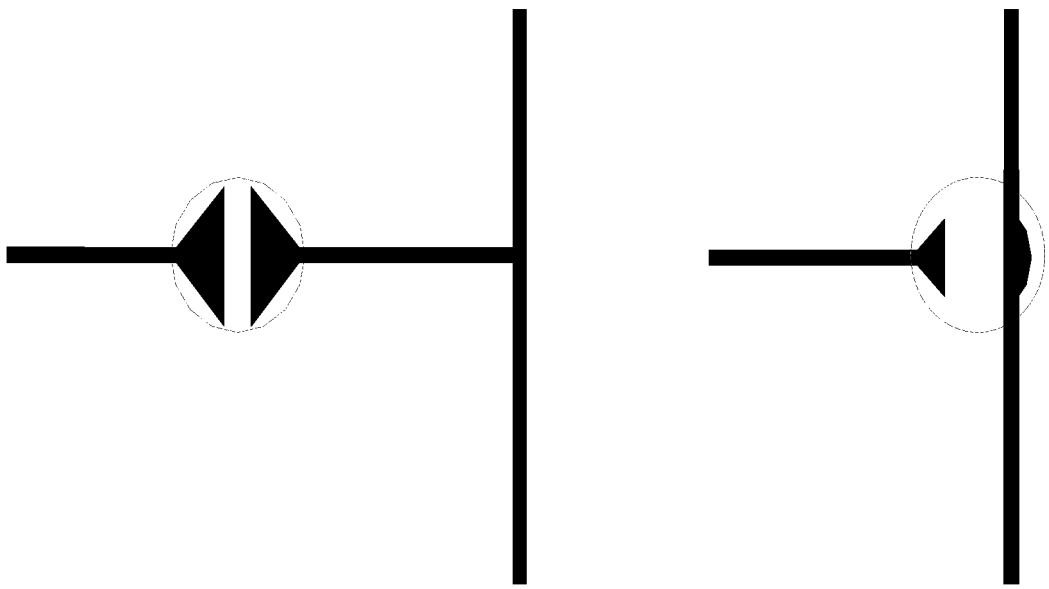
FIG. 25 contrasts on the left using a microvalve that is not at the junction on the left and an embodiment that connects a flowthrough valve as shown in FIG. 24 with another channel to eliminate the dead volume.

FIG. 25 illustrates the difference between the fluidic junctions that connects three channels. On the left, a standard MOV valve is shown to the left of a three way junction. On the right, a flow-through valve is shown. Both the conventional MOV valve and flow through valve can be used to regulate flow or as part of a pump, but the dead volume in the flow through valve is eliminated where as in the conventional MOV valve, the region from the valve to the channel intersection is dead volume.

Figure 24:
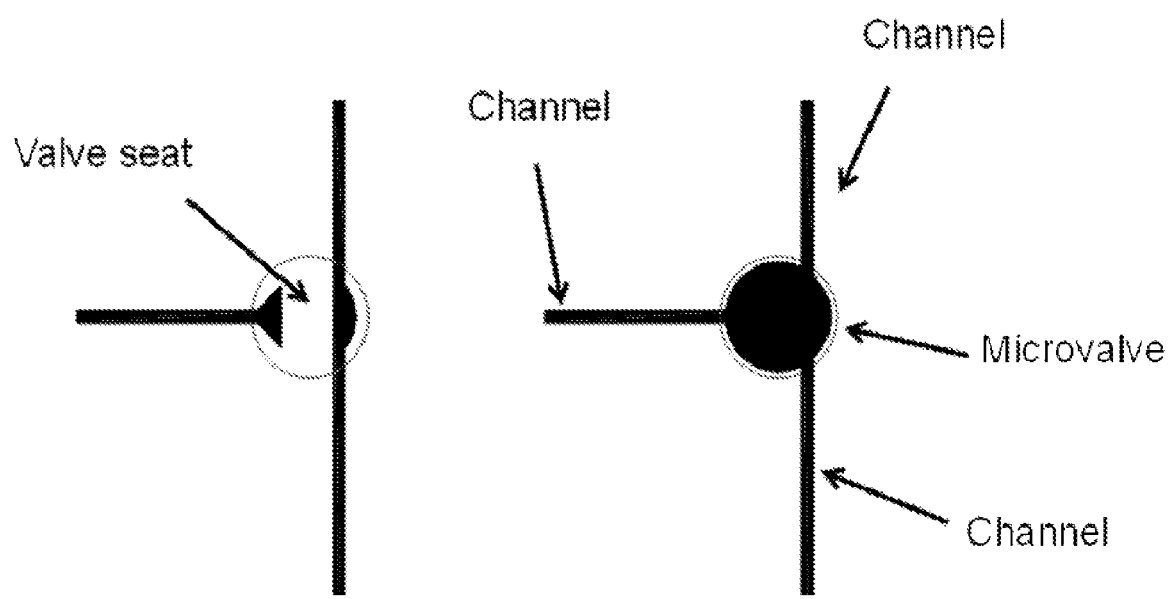
FIG. 24 shows a MOV flowthrough valve where two or more flows can be brought together.

The number of channels in this type of valve may also vary. The example illustrated in FIG. 24 shows one channel passing through and one channel terminating in the valve. In another embodiment a microstructure may be designed comprising multiple channels passing fluid through the valve and/or multiple channels terminating in a closed valve.

Figure 26:
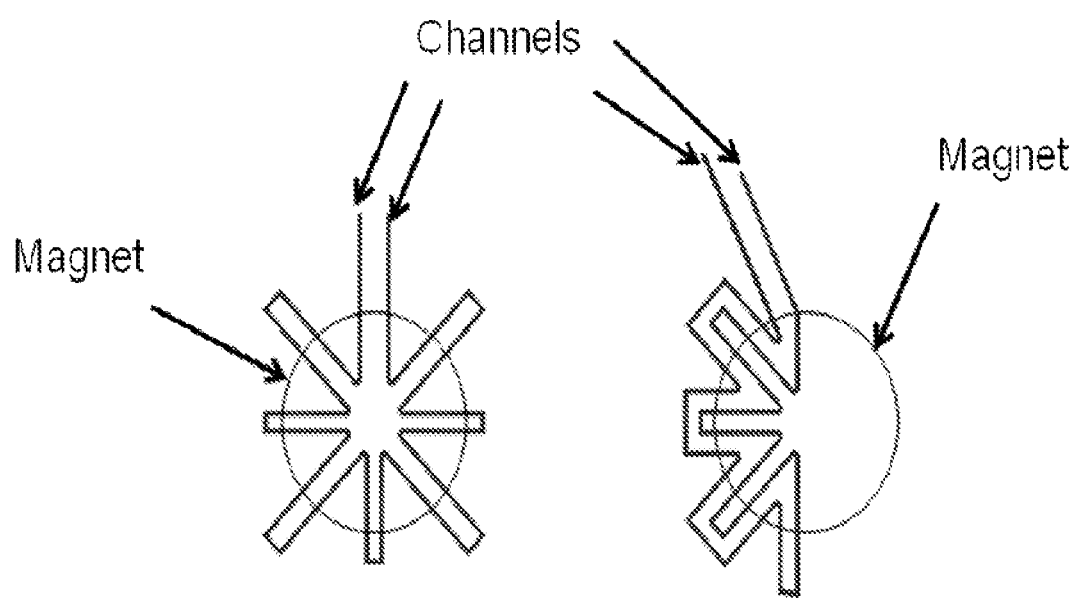
FIG. 26 shows using microfluidic circuits with features to improve the trapping of paramagnetic particles.

Manipulation of Magnetic Beads on Microchips and Other Fluidic Devices Star and Nested Star Capture Device In another aspect magnetic beads are captured as they move through a channel structure. In one embodiment magnetic bead capture is most effective at the edge of a magnetic field. In one embodiment microchannel structures are designed to take advantage of this property by passing a channel through the boundary of the magnet field multiple times. In FIG. 26, the thick lines represent the channel structures and the thin line represents the magnet. In this embodiment the capture efficiency of this system depends on a number of factors including, but not limited to, the sheering force put on the beads by the fluid passing through the channels and the force applied by the magnet. In one embodiment only a finite number of beads can be captured in each channel segment that crosses the magnet when the flow is high. When the beads are captured in the channel, they occupy a fixed amount of space, effectively reducing the channel cross section, and increasing both the fluid velocity and the sheering force. When this balance is reached and exceeded, additional beads are pushed farther along the channel to the next magnetic boundary. Microchannel designs with multiple magnetic boundary crossings allow for a larger amount of beads to be captured in the channel as compared to designs with a single magnetic boundary crossing.

In some embodiments the magnets may be electromagnetic magnets or permanent magnets including but not limited to rare earth magnets, fixed and mobile magnets.

In one embodiment a microchannel designs with multiple acute angles can be used to run thermal cycling. In another embodiment the length of a structure with multiple acute angles can be used for mixing. When liquids come together in a microfluidic system, laminar flow can keep liquids separated. A structure with multiple acute angles and many turns allows for mixing to occur through diffusion. The circuit on the left panel of FIG. 26 can be compacted into the nested star shown on the right or many other configurations. The nested star occupies a smaller space than the full star.

Capture of Beads by Change in the Cross-Sectional Area of a Microvalve

Figure 27:
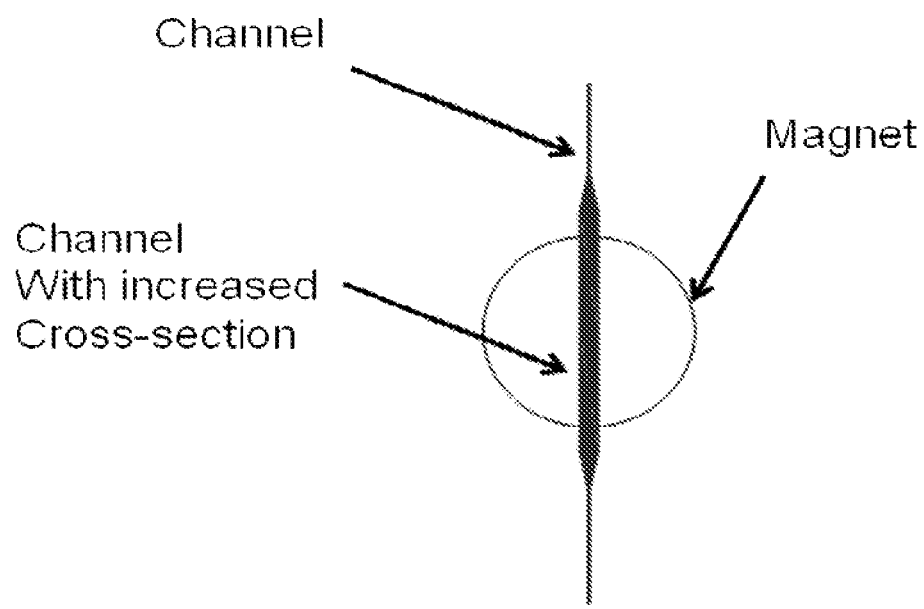
FIG. 27 shows changing the cross sectional area of a microfluidic channel to slow down flow and improve the trapping of particles by magnetic, optical and other methods.

In another aspect the capture of beads can be made more efficient by changing the geometry of the capture region to increase the cross section, FIG. 27. The vertical line represents a channel and the black circle a magnet. As the channel flows through the magnetic field, the width or depth of the channel can be increased. The change in cross section captures the beads more efficiently for a couple of reasons. The increased cross-section results in a slower velocity as compared to the normal channel section for a given flow rate. The slower flow means a smaller force pushing the beads out of the capture region. In addition to the slower velocity, the added volume gives the fluid a path to maneuver around beads that are captured in this portion. The specific geometry can be varied greatly. It can also be used in conjunction with the star and nested star geometries. This increase in cross-section can also serve a number of different functions including a reaction chamber or thermal cycling chamber.

Bead Capture in a Valve

Figure 28:
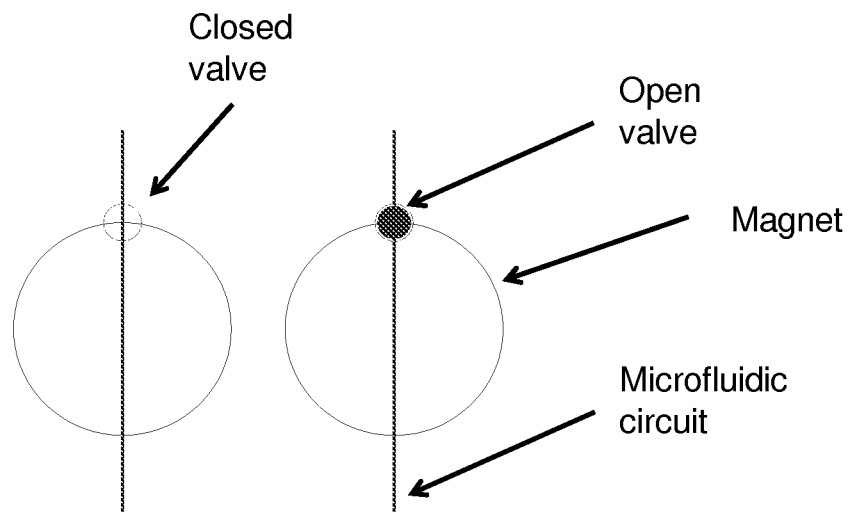
FIG. 28 shows changing the cross sectional area of a microfluidic channel by opening a MOV microvalve to slow down flow and improve the trapping of particles by magnetic, optical and other methods.

In another aspect the bead capture in a valve (FIG. 28) utilizes the same concepts as the capture through the use of an increase in channel cross-section from the above example. The microvalve allows for the cross section of the channel to be changed. When closed, the cross section of the channel remains uniform throughout. With the valve open, the cross section of the channel at the valve is increased significantly and in effect the opening of the valve creates space in the microfluidic channel. As magnetic particles or paramagnetic particles move through an open valve, the flow slows down and the magnet can trap the particles. Closing the valve can release the paramagnetic particles when the magnetic force is properly balanced. Repeated opening and closing the valve can be used to remove the paramagnetic particles. The release can also be affected by passing fluids that interact better with the beads to increase the drag force or by alternating air and liquids in boluses.

Reagent Distribution

In another aspect the interface between the macro world and microfluidic devices is often times one of the more difficult problem to solve. While the microfluidic device may use only volumes as small as nanoliter or picoliter of reagents in an assay, typically much larger volumes of reagents need to be connected to the assay device. For a separation device while only nanoliter or picoliter volumes are injected and processed, the device may need to access larger volumes of sample in order to load this small volume. It is also advantageous to minimize the total amount of reagent in channels to minimize dead volumes.

Common Reagent Reservoir

Figure 29:
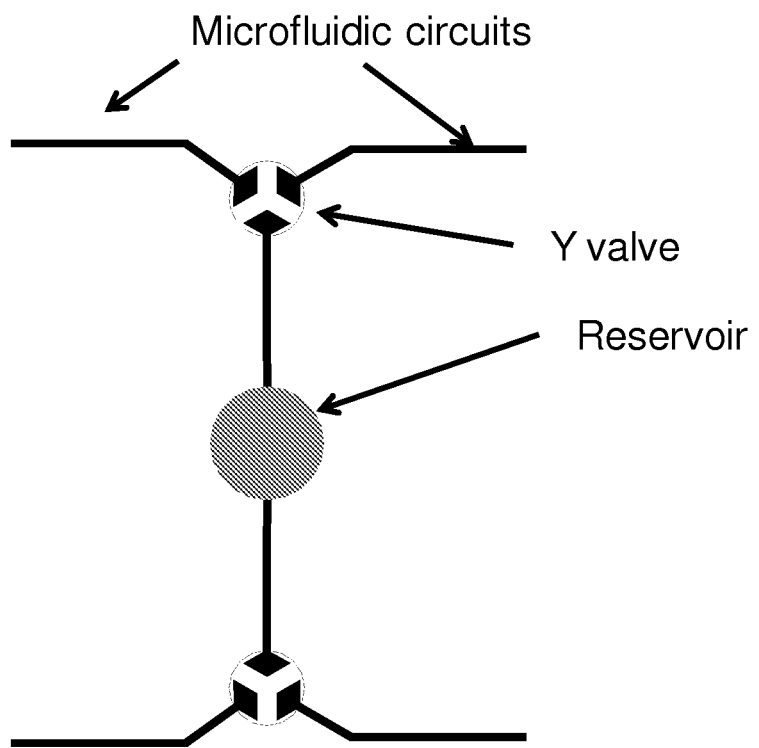
FIG. 29 shows connecting a reservoir or other fluidic source to multiple channels using MOV Y junctions.

In another aspect, a common reagent reservoir is shown in FIG. 29, where a reservoir in the center supplies two channels. In this case the minimum volume needed just to fill the bottom of the reservoir is shared between the two channels, thus the total volume needed to supply two channels is smaller than that of a design that has two channels connected to two independent reservoirs. In this example, each of the two supply channels is further split into two channels using a y-valve. The y-valve isolated the three channels that enter it. The isolation helps to reduce contamination resulting from unwanted flow in the channel that could be caused by evaporation, capillary forces, or other sources. In this embodiment, a single unusable volume required to cover the bottom of a well is shared among 4 channels reducing the total amount of fluid needed for this system. The number of channels that draw from a single well or the number of times the channels are split using an intersection or valve is virtually limitless.

This system could be used in the opposite direction to gather waste. In the example shown in FIG. 29, if the flow is towards the reservoir, four channels could move waste into a single reservoir. The advantage is fewer waste reservoirs that need to be emptied. The reservoir can also contain electrodes and connect four channels to an electrical potential or contain vacuum to pull materials through the four channels modulated by the y valves or other valves.

Reagent Delivery System

Figure 30:
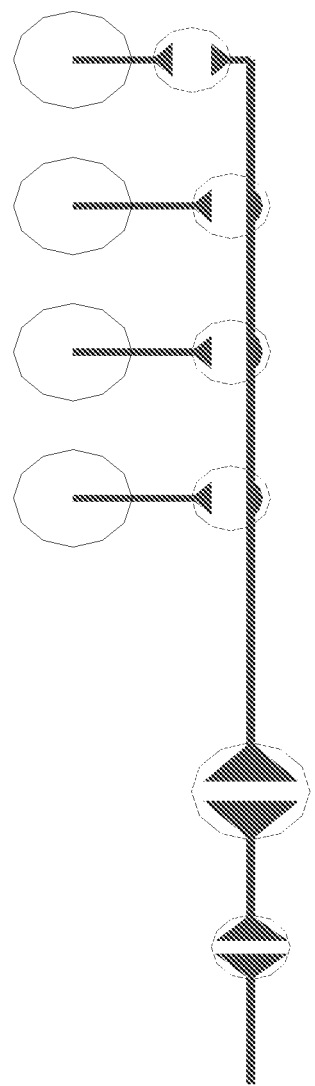
FIG. 30 shows deliver of reagent or sample utilizing the flow through valve to minimize the amount of dead volume at an intersection that allows the channels at the intersection that can be closed off from one another when desired.

In another aspect, a reagent or sample is delivered by utilizing the flow through valve to minimize the amount of dead volume at an intersection that allows the channels at the intersection that can be closed off from one another when desired (FIG. 30). The benefit of this arrangement is that all of the reagents in the chain are pumped using a common set of valves. Using a common set of pumping valves decreases the variation in the ratio of reagents mixed that would otherwise be introduced by variations in different pumping valves.

Reagent Loop

Figure 31:
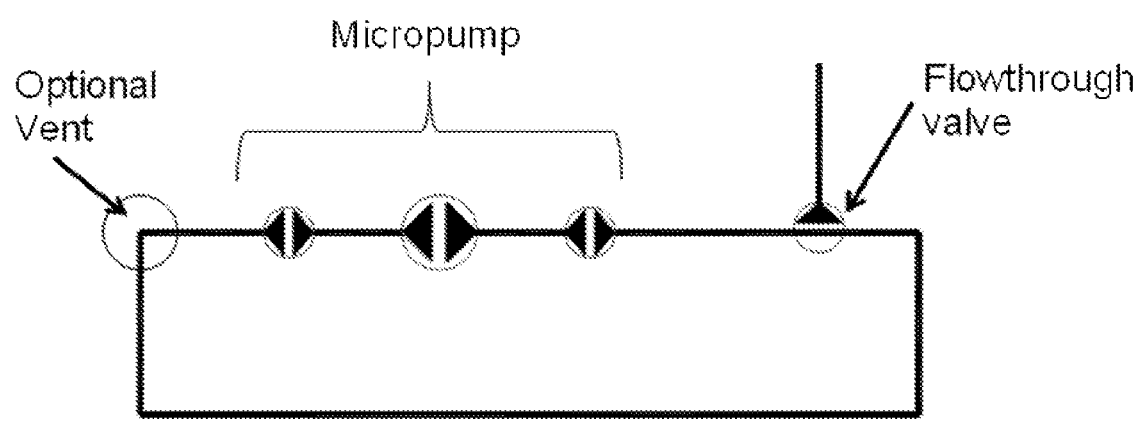
FIG. 31 shows a loop that contains a microvalve such as a MOV micropump.

In another aspect, a microstructure comprises three valves in a reagent loop to act as a micropump to circulate fluid within the loop and a fourth valve, the flow through valve, allows additional material to be moved into or out of the loop (FIG. 31). Multiple flowthrough valves can be used. Using this loop will allow a user to continuously circulate a minimum volume.

This system can also be utilized to elute off sample. Circulating elution solution along with the capture material will allow more time for the sample to elute off and for the high sample concentration regions around the capture material to diffuse away making resulting in an elution of higher concentration.

Integrated Designs

Figure 32:
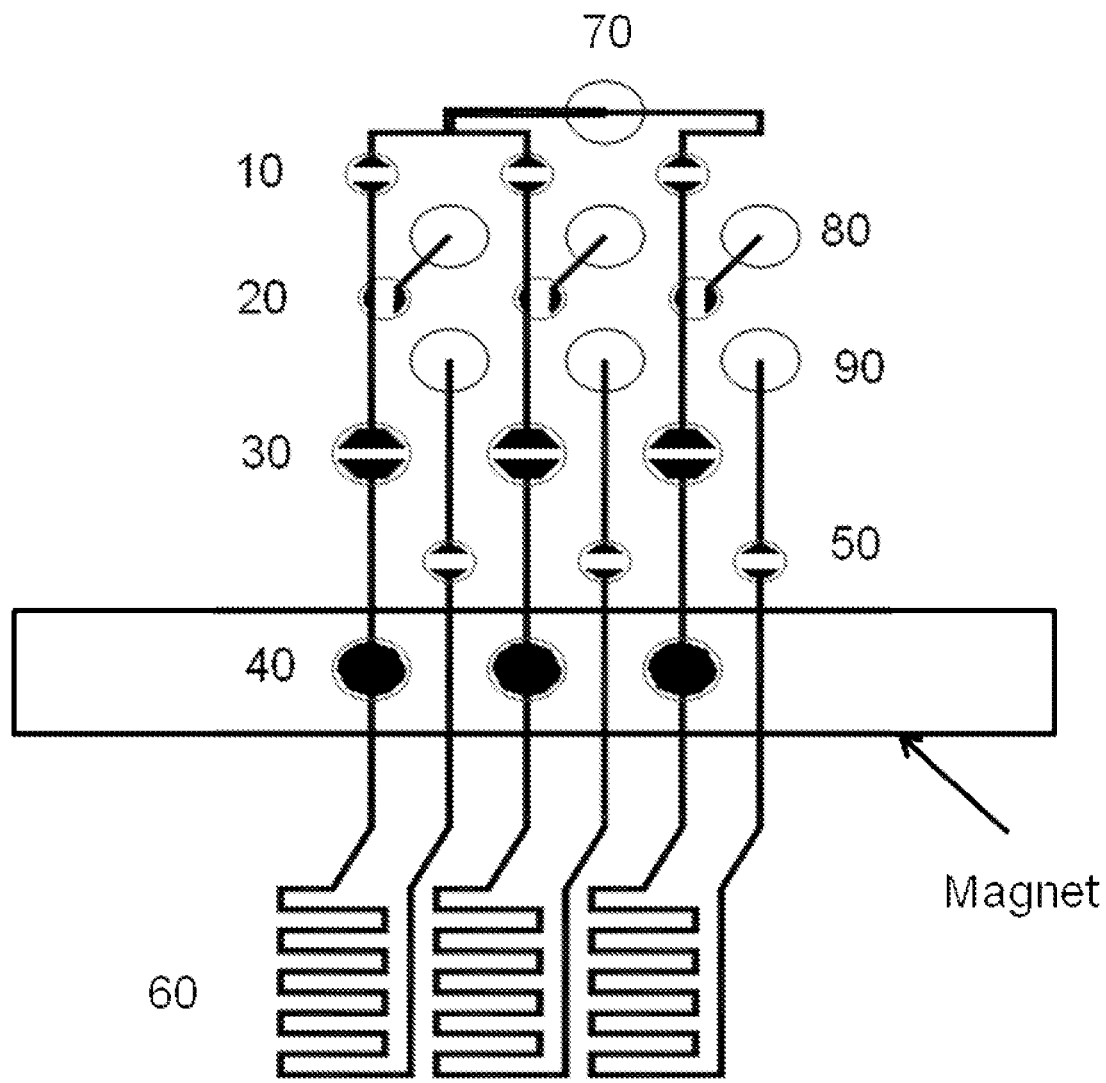
FIG. 32 shows a programmable microfluidic circuit that integrates multiple functions in a compact design.

In another aspect, a system comprising a microstructure is used to perform chemical and biological reactions. In one embodiment, for DNA sequencing, forensics and other application, FIG. 32, the common reagent reservoir is integrated with bead capture in a valve and a reagent delivery system. Three samples can be loaded into the sample reservoirs 80. The reagents from the common reagent reservoir 70s can then be pumped through the check valve 10 and to the flowthrough valves 20. The pumping can be by using valves 10, 30, 40, and 50 for example or by using external pressure with microvalve 10 to modulate the flow. When the flowthrough valve 20 is opened, the sample from the sample reservoir 80 is accessed and can be pumped into the flowthrough stream through microvalve 30 and microvalve 40 into reaction chamber 60. If thermal cycling is being performed, microvalves 40 and 50 can be closed to isolate the reaction chamber. The reaction chamber is shown in FIG. 32 as a channel; the reaction chamber can also be in a valve or moved between valves or channels or other fluidic components. The movement may be by use of on-device pumping or by off-device pumping, where in a preferred embodiment the microvalves may be programmed to direct flow in the desired manner to enable biochemical reactions to be integrated to produce reaction (s) which may also be assays. The product or products may be assayed on the device or moved to another device for assay.

The device shown in FIG. 32 may then perform a second reaction. In one embodiment the reaction may be a bead based reaction that performs biochemical or chemical reactions to further process the sample. The reaction may be interrogated on the device or moved to another device for assay.

In another embodiment, the device is programmed to integrate multiple steps of reactions for DNA sequencing applications. Common reagent reservoir 70 is loaded with cycle sequencing reagents which are mixed with DNA containing samples loaded into sample reservoirs 80 with the samples being in one embodiment PCR, plasmid, or other nucleic acid amplification products that are to be sequenced. The mixture containing the sample and cycle sequencing reagents can be moved by the programmable fluidics using microvalves to a reaction chamber 60 where cycle sequencing reactions are performed using thermal cycling. The cycle sequencing products can then be moved to Product reservoirs 90 for movement off the device for further processing or in a preferred embodiment the cycle sequencing products are moved to a reservoir and beads such as Agencourt SPRI beads are added to the cycle sequencing products with appropriate chemistry to have the desired cycle sequencing products bound to the beads to separate the products from the salts and unincorporated dye labeled terminators or primers which stay in solution. It is obvious to one skilled in the art that rather than binding the cycle sequencing products to the beads the reverse can be performed where the cycle sequencing products are left in solution and the salts and unincorporated dyes are bound to the beads. The term bead is used without restriction to include particles, paramagnetic particles, nanoparticles, gels, gels with affinity capture property or non-specific properties. If the bead and cycle sequencing products were contained in reservoir 80 the combined mixture is pumped through microvalves 20 and 30 to microvalve 40 which may be opened and have a fixed or movable magnet in proximity. The beads such as SPRI beads which are paramagnetic are captured as the flow slows down in the opened microvalve and the beads are captured in the magnetic field. Fluids such as ethanol may be added to reservoirs to then process the beads and remove the undesired impurities such as salts and unincorporated dye labeled reactants. The beads may be then pumped to product reservoirs 90. For cycle sequencing the products are ready to be analyzed on a separate device such as a CAE or microchip with separation. It is obvious to one skilled in the art that the different reservoirs may have other configurations and a single sample can be added to reservoirs 70 and multiple reagents may be added to reservoirs 80 to perform three different reactions on a single sample.

In another embodiment, the device is used for sequencing by ligation or sequencing by synthesis. Beads may be held in a configuration that they may be interrogated by a detector using laser induced fluorescence, Raman, Plasmon resonance or other methods. In this embodiment the bead may be held in a reaction chamber 32 and the reactants moved by micropumps past the beads where fluorescently labeled reactions occur and are read out with the detector. The reactants can then be removed by pumping other fluids to wash the beads to remove the reactants such as pyrosequencing, sequencing by synthesis, sequencing by ligation or other sequencing chemistries. The next reagent may then be added using either on device micropumps to move the reagents or using microvalves to modulate the flow of reagents to perform the next round of sequencing. The beads may be held by magnetics, optical trapping, or other energy methods or by physical constraint such by trapping in weir structures. (U.S. Pat. No. 7,312,611, which is herein incorporated by reference in its entirety). In one embodiment a microstructure comprises an on-chip packed reactor bed design using one or more weir structures that allow for an effective exchange or trapping of beads at a miniaturized level. In one embodiment each bead may perform a reaction or as currently used with pyrosequencing some beads may have additional reactants.

In another embodiment, the beads may be held and some beads intentionally not perform reactions to allow improvement in the detection. The improvement is gained by optically isolating the signal from a bead that has the DNA sample to be interrogated by physically separating beads with signal from other beads by physical dilution of the desired signal. This will improve the signal to noise of the reactions by allowing the control of the signal from other beads and enables the manipulation of crosstalk in channel or chamber. For example if a 100 beads of the same size that do not have DNA sample to be sequenced are added to per bead with DNA then there would be one signal every 100 beads which would improve crosstalk. Other dilutions are also possible.

Figure 33:
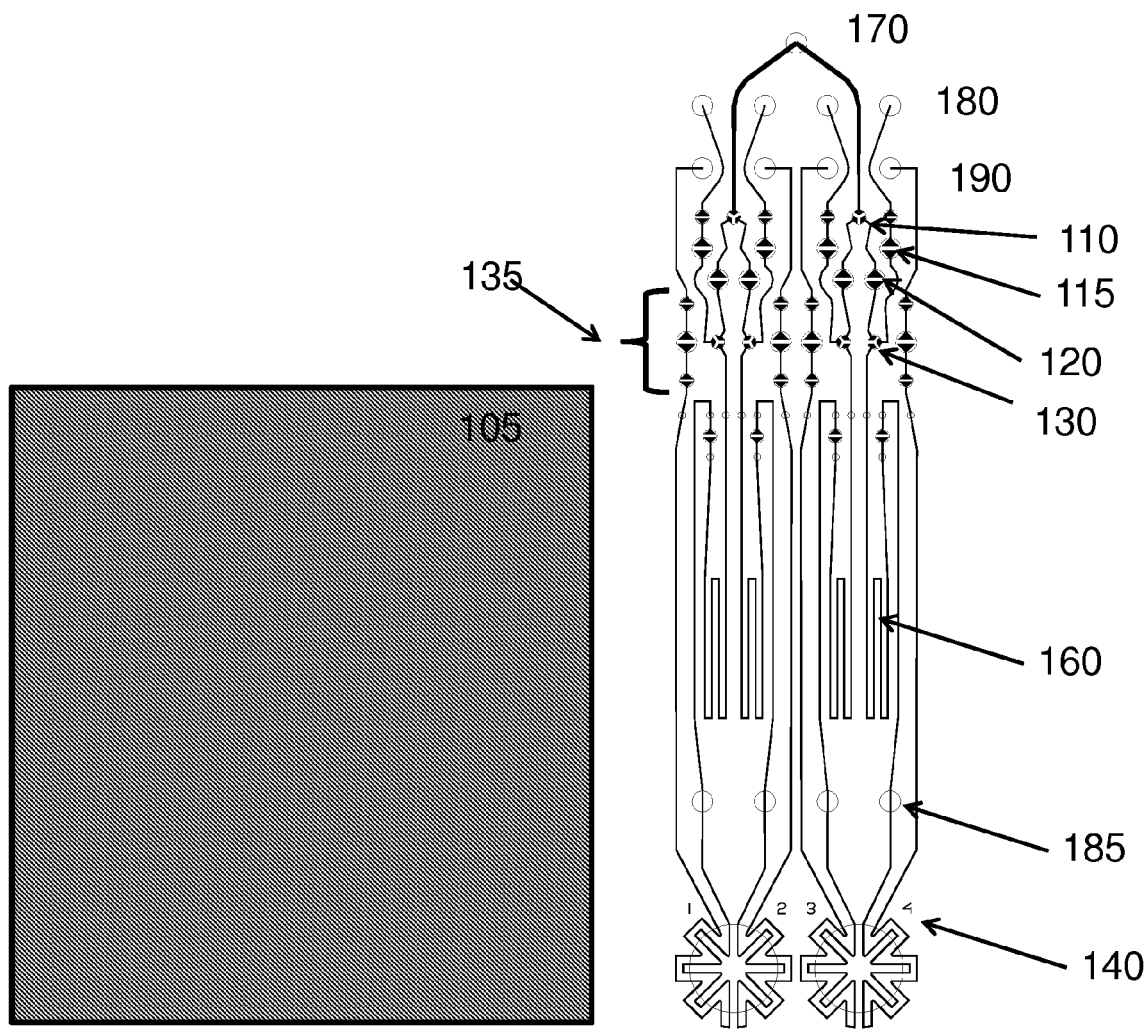
FIG. 33 shows a hybrid plastic microchip.

In another embodiment (FIG. 33), the elements of a common reagent reservoir 70, sample reservoir 80 and product reservoirs 90 and microvalves 10, 20, 30, and 40 are rearranged to use the star capture to produce a device that can perform a reaction and then clean up the reaction products using magnetic or other beads or other purification methods. FIG. 33 shows a different design than FIG. 32 that also can perform DNA sequencing. Samples can be added to reservoirs 180 and cycle sequencing reagents to reservoirs 170, mixed through microvalves 110, 115, 120, and 130 and moved into chambers 160 for cycle sequencing or other reactions. Reservoir 185 can be used to add beads to reaction products which are then moved to star capture circuit 140 for magnetic capture. Washed can be performed by adding different solutions such as for SPRI chemistry, or other bead based chemistries to move the solutions past the entrapped beads to remove the undesired products such as salts or unincorporated dyes.

In another embodiment, an integrated design is capable of running a variety of processes. It can accurately mix together two reagents, run a reaction on the mixture, and clean up the product of this reaction. Because this system has active pumping of fluid between two of the reservoirs, addition reagents can be supplied to the reaction. This design is very compact and has the advantages of using less space per circuit, being able to be packed into a microchip such that a portion can be diced off to improve microchip yield, and performance improvements.

In another embodiment, FIGS. 32 and 33 illustrate the coupling of biochemical and chemical reactions as described for cycle sequencing and chemical reactions such as SPRI cleanup. It is obvious to one skilled in the art that different biochemical and chemical reactions may be integrated by using microvalves on devices. For forensics, short tandem repeat (STR) reactions can be performed on a device incorporating programmable microvalves by using STR reactions such as PowerPlex 16 to amplify DNA and a bead cleanup to purify the reaction.

In vitro transcription reaction, translation reactions or coupled transcription and translation reactions may be performed in the programmable microfluidic circuits to assay DNA, or RNA respectively. This may be used to assay the effects of additional materials added such as microRNAs, inhibitors, drug candidates, chemicals, or other materials to be assayed. This may be employed as a screen for the impact of the added material on the transcription, translation, or coupled transcription and translation reactions. In one embodiment the coupled transcription and translation reactions produce energy harvesting products. In another embodiment a detector 105 is added to monitor reactions in the programmable microfluidic circuit.

The designs shown in FIGS. 32 and 33 are shown in a rectilinear design but it will be evident to one skilled in the art that other designs such as a radial design may be used. ("Roach, D., R. Loder, T. Armstrong, D. Harris, S. Jovanovich and R. Johnston. Robotic microchannel bioanalytical instrument. Sep. 30, 2003. U.S. Pat. No. 6,627,446"; "Roach, D., R. Loder, T. Armstrong, D. Harris, S. Jovanovich and R. Johnston. Robotic microchannel bioanalytical instrument. Jul. 20, 2004. U.S. Pat. No. 6,764,648", "Roach, D., R. Loder, T. Armstrong, D. Harris, S. Jovanovich and R. Johnston. Apparatus and Method for Filling and Cleaning Channels and Inlet Ports in Microchips Used for Biological Analysis. Sep. 7, 2004. U.S. Pat. No. 6,787,111." all of which are herein incorporated by reference, in their entirety). In one embodiment, the microvalves may perform reactions using chemical or biochemical processes to process materials to produce a product or products from a sample. The product is comprised of chemical or biochemical composition and may produce energy, store energy, or use patterns of storage to transform energy in controlled manners.

The integration of chemical or biochemical processes is disclosed on how to produce products or assay components either in the reaction or material added to the reaction to assay some property of the material. The term material is used without limitation and may mean matter or energy where in one embodiment the reaction is assayed by the production of light comprised of fluorescence, luminescence, or other alterations of the electromagnetic spectrum. In one example the programmable microfluidic circuit may perform reactions that are interrogated by a detector such as laser induced fluorescence detector for nucleic acids such by real time PCR, mass spectroscopy or other means well known to one skilled in the art or for proteins by reactions that can be assayed for chemical or biochemical transformations that are catalyzed by the reactants. In one embodiment the device may store energy in bulk or in patterns using chemicals or biochemicals to store the energy in a useful manner such as for visual or optical or manners. The device may be passive or programmable to alter its behavior. This may be employed to alter its signal production in manners that change the optical properties or other properties by chemical or biochemical transformations. This may be used to be a sensor of conditions, a reporter to identify physical objects, transform matter and energy.

The reservoirs may be used to connect the programmable microfluidic circuits to other upstream or downstream devices. A robot may be used to pipette or transfer fluids or modular microfluidic connections may directly connect to other microfluidic devices.

Microfluidic Chip Assembly Method—Thermally Bonded Membrane

In one aspect, a microfluidic chip (microchip) is built from two layers of glass or plastic joined by thermal bonding. Some medical test strips are built from using adhesive (typically in the form of a tape) to join plastic layers with channels and other features cut into one or more plastic and/or adhesive layers.

In one embodiment, programmable microfluidic circuits can be made from features that include MOV microvalves and related features in the chip. (Hereafter, we use "valves" to mean any of this family of features.) In the embodiment shown in FIG. 2, a stack is used with two layers of bonded glass with etched microfluidic channels and drilled holes, a layer of PDMS for the membrane, and a layer of glass into which pneumatic channels are etched to provide actuation pressures to the diaphragms. In this construction, the PDMS is moderately self-adhesive to the glass but can be locally separated from it in the valves and treated to reduce adherence in the valves. Three layer structures are also possible.

In one embodiment, pneumatically actuated microvalves are manufactured in plastic materials. As the material is changed plastic materials for the microfluidic and pneumatic layers, a PDMS membrane no longer has sufficient adherence to use the same construction as with glass and a new method must be developed.

In one embodiment, all-plastic chips have been assembled using heat and pressure to thermally bond a microfluidics layer, a membrane, and a pneumatics layer simultaneously. This process requires careful control to ensure that the layers bond strongly except in the valve area in which the lack of pressure prevents bonding of the membrane to the microfluidics layer—if the time, temperature, and pressure are right. It can be challenging to achieve uniform bonding over an entire chip and not bond in the microvalve.

Figure 34:
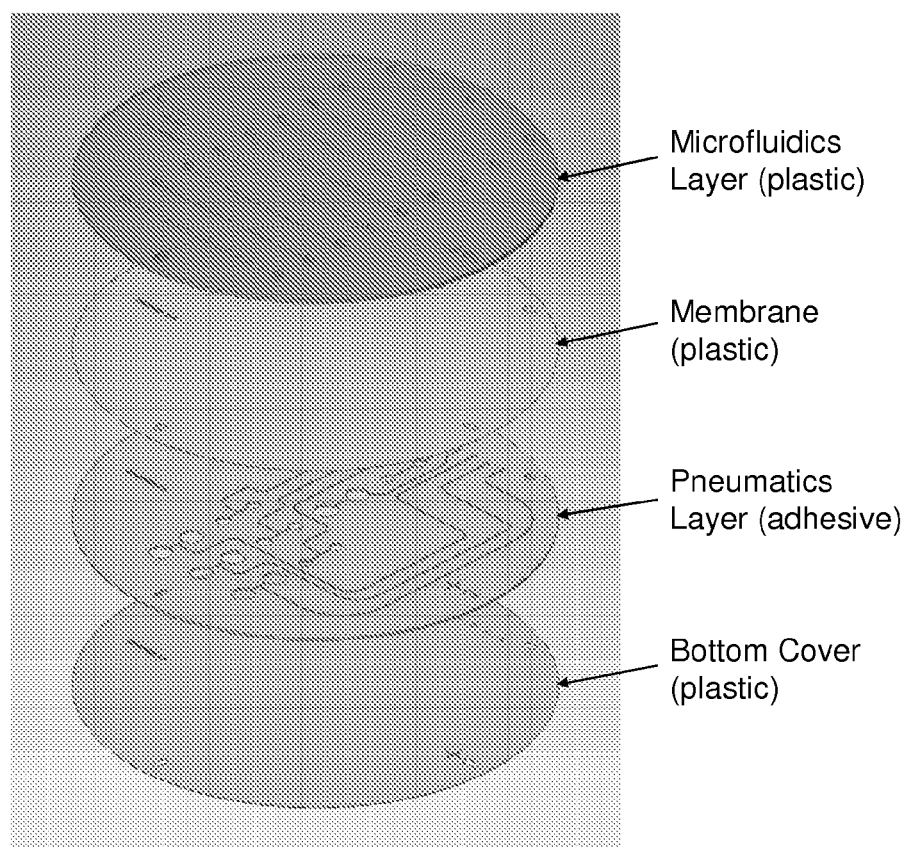
FIG. 34 shows a programmable microfluidic circuit that integrates multiple functions in a compact design using a star processing design and a detector.

FIG. 34 illustrates an example of a hybrid plastic microchip. In another embodiment of the invention, the membrane is thermally bonded to the microfluidics layer using one or more of several methods. Each of the methods avoids bonding the membrane in the valves by keeping its temperature there below the bonding temperature while the rest of it is heated and pressed onto the microfluidics layer. One factor aiding this approach is that the membrane can be made quite thin (e.g., 25 microns) while a typical valve might be 1 to 3 mm in diameter. This enables the use of an approach where the heat is applied to a heating plate that has areas removed in a pattern that matches the valve pattern. To get to the center of the valve from the sides, the heat for bonding must travel 20 or more times the distance it must go to reach the interface between the membrane and microfluidics layers. This makes it possible to heat the bonding area while keeping the valve area cool enough that it does not bond. The relevant areas of the valve seat that should not be bonded can also be surface modified by coating, including using photolithography masking, subtractive etch, chemical vapor deposition, and other methods well known to one skilled in the art. The relevant areas of the valve seat that should not be bonded can also be maintained at a different temperature by localized cooling or the assembly that heats the microfluidic and membrane layers can have regions removed at the valves such that the local area at each valve will receive less heat and thereby not reach its Tg and not bond.

In one embodiment, a membrane is attached to a microfluidics layer by a method comprising of (1) using a heated plate or roller with a profile cut into it so that it contacts the chip components only in areas where bonding is desired, typically everywhere except in the valve areas; (2) Using a laser to selectively heat the desired areas. In this approach it may be desirable for one of the layers to be transparent to the laser wavelength while the other is opaque to it. In this way, the laser energy is absorbed at the interface between the materials where we most want it. An additional stiff but transparent layer should be used to apply pressure to the interface. Alternatively, the "Clearweld" method can be used. In that method, the interface is painted with a special compound designed to absorb a laser wavelength that passes easily through the chip layers which can all be transparent; (3) using a high power IR source and a mask to shade the areas where bonding is not desired. Only the exposed areas would be heated; (4) Ultrasonic welding. Depending on the materials used, these heating methods may optionally be enhanced by selectively exposing the surfaces to be bonded (or not be bonded) to UV light and/or plasma to modify their bonding temperatures.

In another embodiment, pneumatic actuation can be built into a instrument that uses a microchip and the microchip is held against the instrument in a position to allow actuation of the valve membranes. There is great flexibility with this approach in how to make and attach the pneumatics layer. Some embodiments are (1) Cut the pneumatics channels through a transfer tape or double-sided tape (e.g. by laser-cutting or die cutting) and adhere the tape to a cover film and then adhere this assembly onto the microfluidics/membrane assembly or adhere the tape to the microfluidics/membrane assembly first and then add the cover; (2) Mill, engrave, or mold a plastic pneumatics piece so the channels don't go all the way through. Use a liquid adhesive to bond it to the microfluidics/membrane assembly; (3) Mill or engrave the pneumatics pattern through the adhesive side of a tape. (4) Use mechanical clamping to hold the microfluidics/membrane assembly against the pneumatics assembly. In this case, the pneumatics could be part of the chip or part of the instrument as desired; (5) thermally bond a pneumatics piece onto the microfluidics/membrane assembly. Note, can choose a lower-melting material for the pneumatics to avoid damaging the microfluidics/membrane assembly.

In one example a means to make plastic microfluidic chips is provided. Materials can be chosen so that a sample is exposed to only one material. If a supporting plate is at a cool temperature, then the microfluidics layer can stay cool during the bonding process, avoiding shrinkage. There is a choice of methods for generating the required heat. There is great flexibility in choosing materials and attachment methods for the pneumatics layer(s). It is inexpensive. It does not require significant new technology to be developed. It ensures good bonds along the microfluidics channels, even where pneumatic channels cross them. In the existing three-layer simultaneous bonding method, there is a chance that lack of pressure at these locations would prevent good bonding resulting in a leaky channel.

Mechanically Clamped Microchip

In another aspect a microfluidic chip is manufactured by mechanical bonding of the and/or layer to allow for seals to be made between parts that would otherwise not be joined.

In one embodiment (FIG. 35), a mechanically clamped chip allows for the use of a wide variety of membrane layers without the need to find bonding techniques for the variety of materials. This example contains layers that have different property requirements. The microfluidic and pneumatic layers both require the ability to hold small features, the membrane layer needs operate as a MOV valve, and the membrane and microfluidic layers must be compatible with the chemical or biological assays. The mechanical clamping makes the construction of such a part possible without the introduction of additional materials such as adhesives. The different layers are aligned and mechanically clamped together. FIG. 36 show a picture of a chip made in this manner.

Clamped Chip That Reduces Alignment Requirement

In this embodiment (FIG. 37), the fine features that need to be aligned are contained in two layers: the pneumatic layer and the microfluidic and valve layer. The features in microfluidic layer can be bonded by many methods to the sealing layer since both can be made of the same material. Features such as ridges and channels can be placed on the microfluidic and pneumatics layers to aid in sealing to the membrane layer. The pneumatics layer is mechanically clamped with the membrane to the assembled microfluidic and valve layer. The reduced area that needs to be clamped in this design reduces the tolerance stack and simplifies the manufacturing of the microchip.

Adhesive Laminated Microfluidic Chips

In another aspect a laminated microchip is disclosed. MOV microfluidic chips typically contain diaphragm valves and related features, such as pumps, routers, and variable volume chambers (hereafter, we use "valves" to mean any feature of this family), so far using glass for the rigid layers and PDMS for the diaphragm's membrane. Glass to glass interfaces are thermally bonded and the membrane's inherent properties provide sufficient adhesion to join it to the glass without an adhesive.

For many applications, it would be desirable to replace glass with plastic to lower the cost of the microfluidic chips. PDMS does not have sufficient inherent adhesion to plastics tried so far to withstand the pressures used in operating the valves. Further, the permeability of PDMS to gases can allow bubbles to form in valves that are held closed. Such bubbles can be detrimental to the performance of the chip.

In some embodiments adhesives are used to join layers to make microfluidic chips (U.S. Pat. Nos. 6,803,019 and 6,176, 962, which are herein incorporated by reference, in their entirety)

In one embodiment, the various layers of a microfluidic chip are joined using adhesives, and in some embodiments, features such as channels are formed in some or all of the adhesive layers. A key difference from other work in adhesive-laminated microfluidic structures is the inclusion of valve features and related structures. Two examples of embodiments of the concept are shown in FIG. 38 and FIG. 39. In the first embodiment in FIG. 38, the microfluidic layer, interface layer, and pneumatics layer are made of transfer tape which has had appropriate channels and holes cut through them, e.g., by laser cutting. The other layers are made in thin plastic sheets which also have appropriate features cut through them. Thus multiple layers can be made of transfer tape.

In another embodiment, FIG. 39, a microchip is constructed by etching the channels in a glass wafer and thermally bonding it to a glass via layer and using two adhesives to assemble in a different order. Thus manner arrangements are enabled by using multiple adhesive layers which may be transfer tape. The microfluidic layer could have been thermally bonded plastic or fabricated in other materials, with other shaping methods, and/or other joining methods.

In another embodiment, FIG. 40 illustrates a close-up view of a valve constructed by adhesive lamination. When pressure is applied to the valve chamber via channels in the pneumatics layer, the membrane is deformed until it presses against the two vias, sealing them which prevent fluids in one of the microfluidic channels from passing through the valve to the other channel. Vacuum applied to the valve chamber pulls the membrane away from the via openings allowing flow from one microfluidic channel to the other.

In another embodiment, an adhesive lamination method allows for great flexibility in design. There are few limits on what can be integrated into the design. For example, FIG. 41 illustrates an adhesive laminated chip with heaters and heat spreaders built in. Different embodiments add electrodes, optical components, other temperature control components such as heat pipes or heat sinks, sensors, printed markings. Since no heating or only moderate heating is needed to cure the adhesives, these types of additions can be made without damage to them, though they must withstand or be protected from the pressures used in the laminating process.

Adhesive lamination construction is an inexpensive way to create microfluidic chips. There is great flexibility in the choice of materials. Films and transfer tapes of many varieties are readily available off-the-shelf. The chip can be kept quite thin which can be useful for thermal control. If thin enough, it can be flexible enough to be stored in roll form. Features in each layer can be laser-cut, waterjet-cut, or die-cut as needed. These are all fast and flexible methods so prototyping and low volume production can be accomplished quickly. Design changes can be made with short lead time. The necessary technology to implement the method exists and there are multiple vendors capable of supplying the assembly. Mass production can be achieved quickly. Hybrid constructions in which one or more layers are made by different techniques are easily implemented. If desired, the interface adhesive can be made relatively thick to form a normally fully open valve. Such a valve does not require a vacuum source. It could be closed with pressure and the valve would open when the pressure is removed and the membrane returns to its minimal stress position (flat). Additional functionality can be incorporated easily, such as the incorporation of heaters, heat spreaders, optical components, etc.

Valve Arrays Integrated on Plastic Microfluidic Devices

In one aspect of the instant invention, three layers of same plastic material are laminated for obtaining the microfluidic chip. One embodiment is shown in FIG. 42. The bonding parameters for same plastic material are temperature and pressure. In the right conditions, the membrane will be permanently bonded to both top (microfluidic) and bottom (actuation) plates, except for the area above the valve chamber, where pressure conditions are different so the plastic membrane will move down if vacuum is applied in the valve chamber or up if pressure is applied. Pressure conditions are different in the area at the valve since it is not in contact with the bottom actuation layer due to the valve chamber it will experience less pressure during lamination or in a press. When a constant temperature is applied to the whole device or assembly, the pressure will be less on the materials contacting at the valve which will prevent bonding when the temperature is adjusted so bonding occurs only when pressure is transferred to the membrane. This is a normally closed valve. In another embodiment, a normally open valve can be made by adjusting a higher pressure in the microfluidic channels than in valve chamber during the lamination. A depressed membrane will be obtained after device cooling in FIG. 43. Only pressure is needed for actuation this valve. Pressure is available without electrical energy and this valve may be valuable for portable instruments. For these three layer structures, air channels can't cross more than two microfluidic channels and vice versa, because the membrane will not be bonded under the channels (no pressure there). This can be an impediment for ganging valves in a multi-channel device.

In another embodiment the intersecting air and microfluidic channels can be used with a four layer structure. FIG. 44 shows a cross-section of this structure. This valve is normally closed and it needs pressure and vacuum for actuation. The normally open version can be also produced, with pressure-only actuation.

In another embodiment a patternable material that can be selectively deposited on the valve seats and then removed after the bonding is completed, such as photoresist, like Shipley 1818, screen printing of water soluble polymers, light activated compounds such as UV activated polyacrylamide (ReproGel, GE Healthcare), that are compatible with the bonding temperature. An alternative embodiment modifies the surface properties of some areas by changing the melting temperature of the modified region for example by UV activation of plastics such as polycarbonate at areas where selective bonding is needed. In another embodiment, bonding of the membrane to the valve seat is disrupted by passage of liquids such as acetonitrile, preferentially viscous liquids comprising polyethylene glycol and propanediol.

Linear Array of Valves for Bead Cleanup in a Plastic Microchip

In another aspect, a linear array of valves was designed for a bead clean-up protocol. For example, FIG. 45 shows a mask design on the top panel and the picture of an acrylic 3 layer this chip in the bottom panel. A device was made from two 1.5 mm thick acrylic plates and a 0.04 mm acrylic film Microfluidic channels (blue) and actuation channels (red) were milled (0.25 mm wide and 0.1 mm deep) in each one of 1.5 mm plates respectively. Access holes were drilled in both acrylic plates. A special channel for junction temperature control was cut into one plate. The acrylic sandwich was aligned and placed on a planarizing chuck, covered with a glass plate and placed in a press with heated plates. The lamination was done at 100° C. and 1 ton pressure force. The chip was tested for continuous pumping for 3 days. No pump failure was observed.

In FIG. 46, the design and the picture of a three layer acrylic chip for forensic protocols is presented. The chip will mix sample with bead solution, use bead sample concentration in the big valves, mix cleaned sample with PCR reagents, perform PCR amplification and post-PCR clean-up. The chip dimensions are 30 mm×30 mm The channels are 0.25 mm wide and 0.15 mm deep. The amplification channel can hold about 1.5 µL. The microchip works as follows. Pneumatic line 211 actuates microvalves 210 and 220. Pneumatic line 212 actuates microvalve 215. Pneumatic line 213 actuates microvalves 250 and 255. Pneumatic line 214 actuates microvalve 276. Pneumatic line 216 actuates microvalve 240. Pneumatic line 217 actuates microvalve 230. Pneumatic line 219 actuates microvalve 246. The sample which has material attached to paramagnetic beads is loaded into reservoir 280 which is connected to microvalve 220. Pumping by microvalves 220, 230, and 245 can move the sample into microvalve 240 which is opened and has a magnetic field to trap beads. The beads are washed using wash buffer loaded into reservoir 275 controlled by microvalve 276 with pumping by microvalves 276, 230, and 245 with the wash going to waste 247. Reservoir 275 can then be filled with eluent and the purified samples from the beads elueted into buffer compatible with downstream processes and pumped through microvalve 246. At microvalve 255, reaction mixtures is added from reservoir 270 using microvalves 210, 215, and 255 to mix as taught with the elueted sample as it flows into reactor 260. Valves 250 and 255 can be closed if a thermal cycling process is being performed such as PCR or cycle sequencing. Following the reaction, the sample is pumped out to reservoir 290

These examples were designed for various sample preparation protocols like sample concentration, thermocycling (for cycle sequencing or PCR reactions), isothermal reactions, and sample purification. The plastic multi-layer lamination can provide low cost and disposable complex chips with valves and pumps These disposable chips are required in many application fields like forensics and molecular diagnostics. A disposable chip can make the instrument much simpler without preparations and cleaning steps. The use of normally open valves will not require a vacuum pump or a pressure pump. The actuation pressure can be provided by a pressurized cartridge and the whole apparatus power requirements can be acceptably low.

Rapid Movement of Fluids and Reactions in Valves

In another aspect a microstructure rapidly moves a fluid between two or more different spatial locations. There have been a number of approaches to performing thermocycling of reactions for PCR, cycle sequencing, and other purposes. These may generally be placed into two classes. In the first, the reaction components are located in a chamber whose temperature is varied with time. In the second, constant temperatures are maintained in two or more locations and the reaction components are moved from location-to-location and come to equilibrium with the temperature at each location. We may call these "temporal" and "spatial" cycling, respectively.

When performed in microfluidic applications to date, those using spatial cycling generally provide a fluid channel which meanders through the temperature zones, and they force the reaction fluids through this channel unidirectionally, usually at a constant speed. Flow is normally generated by application of pressure generated by devices external to the microfluidic structures.

In one embodiment, thermocycling is accomplished by moving the reaction components between or among zones of different temperatures in discrete steps by means of one or more pumps. The pumps could be external, but in the preferred embodiments, the pumps are internal to a microfluidic chip in which the reaction components are thermocycled. One embodiment is shown in FIG. 47. In this approach, one of our MOV pumps is used to move the sample between a hot zone and a cool zone. For simplicity this diagram illustrates only a two-temperature system. But the invention is not limited this way and it is easy to expand the idea for three or more temperatures.

For example, FIG. 48 shows a way to implement three-temperature cycling. Here an on-chip pump is used to move the sample through three temperature zones. In this case, the temperature zones extend over different volumes of the channels. With constant speed pumping, the sample would be exposed to each temperature for a time proportional to the volume of the channel in each zone. With the on-chip pumping, it would be easy to move the sample in discrete moves instead. In this way, the temperature zones could be made smaller, just big enough to contain the sample. Then the pump would only be actuated for a short period to move the sample from one zone to the next and the dwell at each temperature would be determined by the time between pump actuations. This gives flexibility for adjusting the temperature cycling profile without redesigning the channels or heaters. Note that the sample can be surrounded by an immiscible fluid to keep it from diffusing. Thus boluses and microemulsions are enabled by this programmable microfluidic circuit and the boluses and microemulsions can be assayed with a detector to perform real time reactions or endpoint reactions, for example, real time PCR in boluses or microemulsions. For a higher throughput system, it may be desirable to use a pipeline construction as shown in FIG. 50.

In FIG. 49, an alternative embodiment is shown in which the sample is moved between hot and cool zones without passing through a pump, eliminating interactions with the materials in the pump and loss of sample to dead volumes. Again, an immiscible fluid can be used on either size of the sample to help keep it from diffusing. It is not necessary to have two complete, three-chamber pumps as shown here.

If re-use of these features is needed, it may be necessary to wash or rinse them before re-use to prevent cross-contamination. Additional features may be added for these functions to clean the chambers as shown in FIG. 51 for a segment of a reactor.

In another embodiment, the temperature zones are located at the same positions as valves as shown in FIG. 52 for two-temperature cycling and in FIG. 53or three-temperature cycling. In this embodiment, the bulk of the reaction components can be transferred from one zone to another by closing the valve containing them while simultaneously opening the valve in the destination temperature zone. A portion of the reaction components will be left in the channel and thus not reach the intended temperatures which is undesirable. But by appropriately sizing the valves and channels, this fraction can be kept small. An advantage of this embodiment is that there is no possibility of the sample moving too much or too little and thus not being properly positioned in the temperature zone. The reactions in the valves can be in three layer microvalves where the elastomer or valve membrane is deformed to create a space or in a four layer microvalve where the reaction is performed in the via.

In FIG. 54, an alternative embodiment for three-chamber cycling is shown. In this implementation, the liquid is pumped with a circular rotation. That ensures that none of the sample stays in the channel repeatedly, but increases the channel volume relative to the valve volumes.

In some embodiments it is unnecessary for the valves in the temperature zones to actually make a seal. Only the volume changes as the valves are opened and closed is important. One option this allows is to leave out the valve seats so that the channel allows continuous flow through the thermocycling area. This has an advantage during the initial filling of the chip and movement of the reaction components into the thermocycling area. During filling, all but one of the valves can be left closed using the least necessary volume of reagents. If the valves have seats, they must be open to allow filling. If the chip is filled until the reaction components are seen to reach the far end of the thermocycling area.

In some embodiments, it is desirable perform thermocycling in a device that has one or more of the following characteristics: rapid temperature transitions; stable, accurate temperatures; small, lightweight package; disposable reaction container; small reaction volumes; low power requirements; automated mixing of sample and reagents; programmable control of temperature profile (temperatures and times); configurable for a range of sample sizes (nanoliters and up); configurable for a range of numbers of samples (from 1 per device to hundreds or more); low operating cost; low pressure requirements to move reaction components through the device.

In one embodiment a microstructure thermocyler is mobile or handheld. In another embodiment the microstructure thermocyler is not battery powered. In one embodiment a fixed zone heating approach is used to keep power requirements acceptably low and micropumps are used to move fluids between temperature zones. In another embodiment microvalves are used to control fluids comprising analytes, particles, nanoparticles, emulsions, microemulsions, reagents and combinations thereof.

Reactions in Microchips and Their Use in Library Construction and Analysis

Traditional Sanger shotgun sequencing has involved laborious, expensive, and time consuming in vivo cloning, selection, colony isolation, and amplification steps. The large genome centers have automated many of these processes with islands of robotic automation. Next generation technologies now under development or in early stage deployment by companies such as ABI, Solexa, and 454 may offer radically lower cost sequencing by performing reactions on small ensembles of molecules. At the same time, these technologies and others such as SuperPyroSequencing and single molecule sequencing—will vastly change sample preparation requirements and methods.

The 454 Corporation has now developed pyrosequencing in a miniaturized format with picoliters reactions on individual beads in a "Picotiter plate" with shotgun template generation by emulsion phase PCR (Margulies M, et al. Genome sequencing in microfabricated high-density picoliter reactors. *Nature,* 2005 Sep. 15; 437(7057):376-80. Epub 2005 Jul. 31.). Each four hour run generates about 25 M bases per run of sequence with average readlengths of about 108. The sample preparation procedure to support each run is complex with many manual steps. DNA adaptors are added to sheared DNA libraries, single-stranded DNA purified, and DNA amplified from single molecules on beads by emulsion PCR (emPCR). Emulsion PCR has the ability to generate millions to billions of separate compartments in a single tube using a conventional thermal cycler. Dressman et al. have produced clonal PCR amplicons attached to magnetic particles using emulsion PCR (Dressman D, Yan H, Traverso G, Kinzler K W, Vogelstein B. Transforming single DNA molecules into fluorescent magnetic particles for detection and enumeration of genetic variations. Proc Natl Acad Sci USA. 2003 Jul. 22; 100(15):8817-22. Epub 2003 Jul. 11.) and (Diehl F, Li M, He Y, Kinzler K W, Vogelstein B, Dressman D. BEAMing: single-molecule PCR on microparticles in water-in-oil emulsions. Nat Methods. 2006 July; 3(7):551-9.) and procedures for amplification of complex libraries have been developed (Williams R, Peisajovich S G, Miller O J, Magdassi S, Tawfik D S, Griffiths A D. Amplification of complex gene libraries by emulsion PCR. Nat Methods. 2006 July; 3(7):545-5). The process to produce the clonal libraries on beads takes about two days, with a number of manipulations with specialized equipment, and produces beads of about 375 bp. The sample preparation has become a major rate limiting step for the G20 throughput. It will not be possible to generate the over 100-fold increase in bead production to sequence a human genome per day without full automation. To extend the 454 sample preparation to de novo sequencing mammals and other complex genomes require a rapid hierarchical cloning strategy and the processing of hundreds of thousands of libraries per day. The same sample preparation can be applied to SOLiD sequencing by ligation In one aspect, miniaturized sample preparation is used to automate library processing into bead libraries through the use of microfabricated structures, microfluidics, and magnetic separation combined with improved emPCR. Massively parallel bead libraries, which are required to enable the automated hierarchal sequencing approach, can be constructed. For example, 4,032 individual libraries can be created every 45 min with each single, clonal microsphere carrying sufficient DNA template for pyrosequencing. In some embodiments devices are constructed with from one channel to hundreds of thousands of microchannels capable of processing up to a million individual sequences.

While the examples describe DNA pyrosequencing, the DNA analysis methods can be other reactions such as sequencing by synthesis such as by Solexa, Helicos, ligation reactions such as Agencourt/Applied Biosystems to sequence, and other DNA analysis methods.

In addition to creating libraries for DNA sequencing, the same approach can be made to make DNA libraries or samples for other DNA analyzes, RNA analysis, proteins, carbohydrates, lipids, and other biomolecules. These include samples that were produced by programming in vitro DNA-RNA-protein systems, such as coupled transcription-translation systems, systems that perform modifications to biomolecules, and products from those systems. Similarly, the approach can be extended to chemical libraries and synthesized biomolecules libraries.

The approach can also be used to implement molecular biology reactions in devices such as microchips.

In the following examples, ligation is used in many of the examples. In addition to ligation reactions, one skilled in the art can readily see that all biochemical and chemical reaction can be performed, e.g., restriction, DNA modification, polymerization, DNA—protein binding, and other biochemical reactions, as well as additions, cleavages, cyclicization, condensations, and other chemical reactions.

Automated Bead Based Cloning and Amplification in Fluidic Systems for Microbead-Based In Vitro Emulsion Phase PCR Library Construction In one aspect, bead-based cloning and amplification methods and instrumentation can be based upon an automated instrument, to rapidly process large numbers of sequences. For example, 128,000 input BAC or other libraries can be processed into 250,000,000 beads ready for SuperPyroSequencing (SPS) of a human-sized genome every day. FIG. 55 illustrates a high level depiction of the workflow and processes. The term SuperPyroSequencing is used to describe readout of the beads produced in the NanoBioPrepSPS where the beads contain a DNA library made from single copies of templates. In other implementations a different chemistry can be applied to additional workflows to perform Real Time PCR in boluses, emulsions, and microemulsions. Other biochemistries are also possible as described in this instant invention. The NanoBioPrepSPS' platform is one example of combining bead based chemistries for sample preparation for a DNA sequencing implementation. In some embodiments gene expression, protein expression, and other implementations can be adapted to bead based reactions, and reactions in fluidics (U.S. Pat. Nos. 6,190,616; 6,423,536; U.S. application Ser. No. 09/770,412; U.S. Pat. No. 6,870,185; U.S. application Ser. Nos. 10/125,045; 11/229,065; all of which are herein incorporated by reference in their entirety). In some embodiments boluses of samples in an immiscible fluid or microemulsions are analyzed, such as in the SuperPyroSequencing example. This is another example in this invention that teaches how to couple biochemical and chemical processes and perform multiple reaction steps with microfluidic devices. It is clear to one skilled in the art that modular microfluidic connections can enable moving samples produced as described herein.

In one embodiment the NanoBioPrepSPS could input 4,023 end-polished libraries per 45 min and in a Ligation Module perform 4,023 nanoscale individual ligations of keyed adaptors on 42 microchips, each with 96 channels. The Ligation Module then pools the libraries and bind single fragments onto single beads. The emPCR Module uses emulsion phase PCR (emPCR) to create a bead-based DNA library for SuperPyroSequencing.

In one embodiment, a single channel microchip can perform the ligations and commence development of scalable hardware, microchips, and software to fully automate the microchip portion of the Ligation Module. A 'BeadStorm' device as described below, can resuspend, mix, process, bind, and move magnetic and non-magnetic beads. For the emPCR process, hardware to accommodate up to and over 100 mL emPCR reactions and other parts of the workflow is disclosed for a single emPCR channel; other implementation can use additional channels which are within the scope of the present invention. A robust full scale procedure is may be used to produce high quality beads libraries.

In one embodiment, the NanoBioPrep SuperPyroSequencing (NanoBioPrepSPS) process (FIG. 55) automates library processing to ligate adaptors, construct a single-stranded DNA library, and perform emulsion phase PCR (emPCR) to produce beads, plastic, polystyrene, glass or other beads, with clonal populations of DNA fragments derived from Bacterial Artificial Chromosomes (BACs), BAC-equivalent libraries, reverse transcription products, single samples, whole genome amplification, pooled samples such as environmental samples including aerosol collectors for monitoring including biodefense applications (collectively termed libraries). The final products, a DNA bead library, supply a SuperPyroSequencing readout instrument to collect complete de novo mammalian-scale genome sequencing in a single day.

In this example, the NanoBioPrepSPS process inputs 4,032 individual libraries per run, which have been pre-sheared to a population centered around 1,000 base pairs undergone end-polishing and phosphorylation, from 10½ 384 well microtiter plates every 45 min. The NanoBioPrepSPS will thus process 128,000 libraries per day, generating up to 250,000,000 beads. The amounts of beads generated will be tunable. Each bead will harbor amplicons of up to 1,000 bp, sufficient to produce 60 B bases of sequence data per day—a human-sized genome at 10× coverage in a single day. The NanoBioPrepSPS instrument example teaches effective and efficient means of front-end sample preparation to produce shotgun libraries ready for SuperPyroSequencing for de novo and re-sequencing modalities as well as other microbead and microemulsion processes which can be combined with the biochemical and chemical processes enabled in this instant invention.

In another embodiment, the NanoBioPrepSPS instrument integrates two modules as shown in FIG. 55. The Ligation Module inputs the fragmented, sized, and end-polished, libraries (1) binds unique adaptors to the ends of the fragments, (2) repairs 3' nicks resulting from the ligation reactions, and (3) denatures to generate single-stranded (SS) DNA libraries for input into the second module, the emulsion PCR (emPCR) Module. The emPCR Module (1) anneals the SS libraries onto beads using bound capture primers under conditions whereby a single DNA molecule will bind to a single bead, (2) performs emPCR to amplify DNA on the beads, (3) denatures the double stranded DNA to produce glass beads covered with SS amplified library fragments, and (4) enriches DNA-containing beads from null beads by another magnetic bead capture using annealing primers. The final SS bead library is fed to the SuperPyroSequencing instrument for sequencing and analysis.

NanoBioPrep$^{SPS}$ Ligation Module

In one aspect, a device is provided that comprises massively a parallel microchip-based instrument utilizing MOV valves, pumps, and routers to automate the individual ligation of 4,032 different pairs of adaptors onto 4,032 different libraries of polished fragments per run, with subsequent pooled nick repair and denaturation to generate key-coded, single-stranded libraries. The NanoBioPrepSPS Ligation Module can consist of 42 microchips each with 96 channels (FIG. 56). Each channel of the microchip will process an individual library of fragments by ligating two adaptors onto each fragment. A single NanoBioPrepSPS microchip is described that implements the simultaneous addition of adaptors for 96 libraries.

Loading Libraries onto Microchips

In one embodiment libraries in microtiter plates such as 384 well can be transferred 96 samples at a time to a microchip (FIG. 57) using an array of capillary transfer tubes at 9 mm spacing, termed a capillary cassette. Lower and higher amounts of capillaries can be used. FIG. 58 shows a picture of a 96 channel capillary cassette used for reactions. For this NanoBioPrepSPS example, the capillaries can be just long enough to dip into a microtiter plate well and just wide enough to fill by capillary action. After filling from a microtiter plate, the transfer capillary cassette is moved robotically to the 96 input wells of microchip which has 96 ligation circuits in an 8×12 format at 9 nun spacing. The capillary cassette is then briefly cleaned before reuse to fill the next microchip. We have previous built capillary cassettes and cleaning stations.

Adaptor Ligation Reaction

In one embodiment, the microchip or other device can move the sample from the array of capillaries using pressure or vacuum, or electrical driven, centrifugation or other forces well known to one skilled in the art. For example, a 96 on-chip MOV pumps attached to the input wells can pump the libraries into the microchip as shown in FIGS. 59 and 60. The samples are mixed in a MOV mixer with 96 individual ligation mixtures, and pumped into a nano-ligation reaction chamber (FIG. 58), where they are incubated for example for 5 min. This produces mixtures of adaptors attached to the input sheared library sample DNA. FIG. 58 shows two ligation reaction circuits while FIG. 59 shows the mask design for a 96 channel NanoBioPrepSPS.

In one embodiment, each adaptor can have a key such as a six base that serves to identify the library after sequencing (provided that each set of 4,032 libraries is analyzed separately per SuperPyroSequencing analysis run which can be accomplished by simply dividing the reactors). The adaptors will contain nested PCR and sequencing priming sites, blunt 3' ends and 5' overhangs; one adaptor of each pair will have a biotin on the 5' end. Since a 6 base long sequence generates 4,096 individual keys, and a 42 microchip device with 96 channels requires 4,032 unique keys, the remaining available 64 keys can be used for quality controls incorporated into each NanoBioPrepSPS run, to monitor optimum performance. After ligation, each ligated fragment will contain a PCR priming site, sequencing primer site, and a six nucleotide long key sequence on one end, polished insert genomic library DNA, and a second end with both PCR and sequencing priming sites, as well as a key sequence.

In one embodiment, following ligation, the 96 uniquely encoded libraries will be pooled first from one microchip and then for all 42 microchips, and 20 quality control key sequences added, one group with ten control sequences of "normal" sequencing difficulty, five control sequences with increased difficulty, and five challenging control sequences including all four homopolymers runs.

In one embodiment, reaction chambers such as 800 mL can be used or other volumes such as 400 to 200 mL reactions performed. 384-channel microchips would create a Ligation Module that could for example process 512,000 libraries per day with 42 microchips and scale linearly with additional microchips or instruments.

In one embodiment, Pre-binding of one of the adaptors via for example a biotin-streptavidin linkage to a paramagnetic bead would result in bead-bound fragments with separate adaptors on each end to manipulate the 4,032 reactions using magnetics after ligation. The MOV micropumps routinely work with beads in microchips and captures beads in channels with magnets (FIG. 61).

Nick Repair

In one aspect, after ligation, the beads (or libraries) from all microchips in the device can be pooled and if on beads trapped by a magnetic field in a 5 mL Repair Reactor. The bead vortex and magnetic bead actuation devices used in its Sample Capture and Preparation Module (being developed for biodefense applications) enable a device termed BeadStorm™ device that dispenses, mixes, and traps magnetic bead suspensions in a temperature controlled chamber. The nicks at the ends of all ligated adaptors will be repaired by Bst DNA polymerase. Following nick repair, if the DNA has not yet been attached to beads, pre-washed and equilibrated streptavidin beads are added and the repaired DNA attached by the biotin bound to one set of adapters. The beads are washed to remove unattached fragments and adapters, alkaline denatured, and another set of 8 keyed single-stranded QC sequences added. The released single strands are moved to the emPCR module and the magnetic microspheres discarded. The Repair Reaction and denaturation steps should take approximately 40 min and will be done in a single batch per run. The upstream Ligation Module microchips are regenerated and another run begun which can be while the Repair Reaction is being processed.

In one embodiment quality of a library can be assessed using an Agilent 2100 or similar device or in the NanoBioPrepSPS instrument Automation may produce uniform libraries that lead to the elimination of the quality check at this point. If necessary a single-channel CE component can be added to for the Ligation Module.

NanoBioPrep$^{SPS}$ emPCR Module

In one aspect, the NanoBioPrepSPS emPCR Module will bind the DNA to optically-transparent capture beads to accommodate detection of downstream sequencing reactions, prepare and thermal cycle emulsion PCR (emPCR) at up to 100 mL volumes, denature the resulting amplicons, and isolate DNA containing beads as shown in FIG. 61.

Binding to DNA Capture Beads

In one aspect, SS DNA prepared in the Ligation Module with ligated priming and key sequences will be annealed to polystyrene or other beads containing a complementary DNA capture primer. The beads will be prepared separately off the device. Templates will be annealed by heating the solution to 80° C. in a 25 mL MBI BeadStorm processor and then ramping down the temperature with holds every ten degrees. The temperature ramp and hold times can be individually optimized. Another 8 keyed single stranded QC sequenced can be added at this step.

Emulsion Phase PCR Amplification

In one aspect, the emPCR reactions will be thermal cycled, the emulsion broken, and the beads with amplified double-stranded products purified. Scaleup to 42 microchips with approximately 30 mL of PCR reaction mixture in a total volume of 100 mL per run can be done. Because the total time for the emPCR step is about 6 hrs, which will encompass eight 45 min runs, 9 parallel emPCR reactors will be required, each capable of processing the 100 mL emPCR reactions for the throughput in this example.

The samples for each emPCR run of 4,032 libraries will be flowed into a 100 mL tube that runs through the emPCR reactor; alternatively, the emPCR may also be performed between two plates. Once the polymerase enzyme has been heat-activated in a pre-treatment chamber, the samples will be moved into the common reaction chamber which will cycle up to nine simultaneous large volume PCR reactions. The final 12 keyed QC sequenced beads are added at this step.

Figure 62:
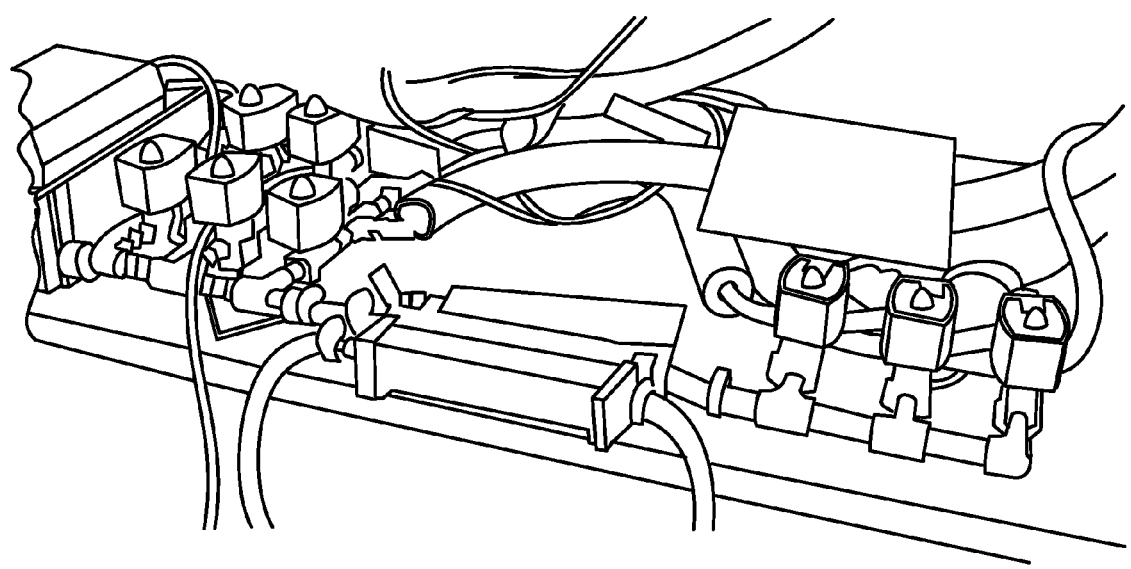
FIG. 62 shows a thermal cycler using circulating water.

In one embodiment emPCR can initially be done in conventional 96 well microtiter plates while the eight parallel emPCR reactors are designed. For large volume thermal cycling, in one embodiment three circulating water baths with selection valves can produce a thermal cycling instrument capable of processing high volumes with excellent ramps. This instrumentation has been previously built (FIG. 62) and shown to enable rapid thermocycling—due to the optimal heat-transfer properties of water—to work well for cycle sequencing and PCR. Software can control the three circulating water baths and operate the full scale valves that select the water and temperature to be circulated. Emulsion chemistries can create mono-disperse emulsions with sufficient volumes to produce 1,000 base long fragments per micro-emulsion. In addition to using three circulating sources of water the temperature can be changed by circulating air or liquids with different temperatures. In a simple implementation, essentially three hair driers set to three different temperatures could be used to quickly change the temperature of a sample. The heated air could be recirculated or a fixed temperature maintained by running the heaters or hair driers at constant temperatures.

Enrichment of Single-Strand DNA Beads

In one aspect, beads with single stranded DNA can be collected and then enriched with a magnetic pull-up, for example by the method of Margulies et al, by (1) replacing the MPC-S with our custom device, (2) replacing centrifugation steps by settling or filtration to change buffers and wash the beads, and (3) adjusting the procedure for the density of the optical beads rather than Sepharose beads. To collect the emPCR beads from the emulsion, the PCR amplified emPCR solution can have isopropyl alcohol added, the solution mixed and forced through a sieving filter using a syringe pump. The filter is washed and moved to a BeadStorm where annealing buffer with 0.1% Tween is added and the amplified DNA alkaline denatured. After incubation, the single stranded DNA containing beads can be concentrated by settling, the supernatant is removed, and annealing buffer added. After washing, magnetic capture beads are added to purify the beads with single stranded DNA by pull-down, the supernatant and unbound beads removed, and Melting Solution added to break the hybridization. The magnetic beads are trapped while the supernatant containing the enriched beads with single-strand template DNA is removed. The NanoBioPrepSPS can then output the pooled and keyed purified libraries ready for SuperPyroSequencing.

42 Microchip Ligation Device and an emPCR Module and Integration

In one aspect, the Ligation Module can be expanded from 1 to 42 microchips and latching valves as described below used to design a 42 microchip device. The workflow with a single microchip Ligation Module and a single channel emPCR Module can be used to process human-derived cancer cell line libraries in a non-integrated workflow. A single Ligation Module microchip and downstream processes can be integrated with a single-channel, flowthrough 100 mL emPCR thermal cycler to make an automated integrated prototype capable of processing 96 libraries per run.

In one embodiment To complete the NanoBioPrepSPS, the 42 microchip Ligation Module can be integrated with a nine-channel emPCR Module as disclosed in this instant invention. The microchip Ligation Module can be integrated physically and through software with the one channel emPCR Module in a breadboard. The full 42 microchip Ligation Module can be built and integrated with a 9-channel emPCR Module. A fully integrated NanoBioPrepSPS can be optimized and samples analyzed on the SuperPyroSequencing device to perform DNA sequencing for example by pyrosequencing, sequencing by synthesis, sequencing by ligation or other methods well known to one skilled in the art to achieve a system capable of complete human de novo sequencing in one day.

Figure 63:
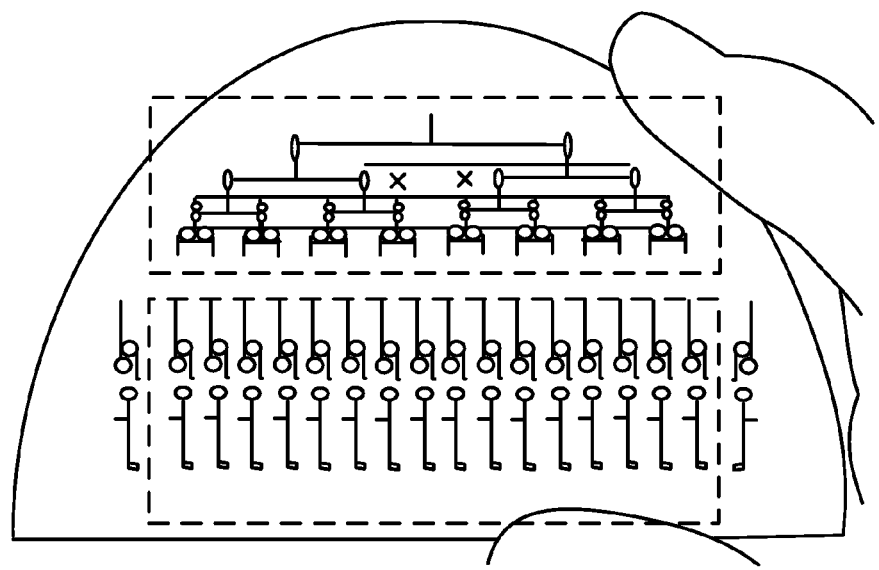
FIG. 63 shows a multiplexed latching microvalve device.

In one embodiment, the ligation module can be expanded from 1 to 42 microchips. The latching valves can be used to control the 42 microchips and will begin to design the full system hardware. In one embodiment latching microfluidic valve structures controlled independently using an on-chip pneumatic demultiplexer are used (FIG. 63). These structures are based on the pneumatic MOV valves and depend upon their normally-closed nature. Vacuum or pressure pulses as short as 120 ms are adequate to hold these latching valves open or closed for several minutes. In addition, an on-chip demultiplexer was demonstrated that requires only n pneumatic inputs to control 2(n−1) independent latching valves. Latching valves consisting of both three- and four-valve circuits have been demonstrated (W. H. Grover, R. H. C. Ivester, E. C. Jensen and R. A. Mathies. 2006. Development and multiplexed control of latching pneumatic valves using microfluidic logical structures. Lab-on-a-chip. Electronic publication). This technology in effect moves banks of solenoids onto the microchip and reduces cost and complexity.

In one embodiment, a pneumatic controlled NanoBioPrep microchip can be built using latching valves for example for 42 microchips. The capillary cassette transfer mechanism interfaces a robotics system with the capillary cassette to load a four microchip device with 2,500 valves.

In one embodiment, the emPCR Module can handle 100 mL in a single channel for example. A high capacity circulating thermal cycler (as shown in FIG. 64) can be built with three different independently thermal cycling regions. Nine separate 100 mL emPCR reactors will be required to share the main circulating thermal cycler, which will continuously perform the same cycling protocol. A pretreatment chamber can accommodate binding to polystyrene or other beads and prepare the emulsion, before adjusting the temperature to accommodate quick start requirements. A post-treatment chamber enables post treatment requirements such as breaking the emulsions and extractions. All three thermo-cycling chambers can share the bulk circulating water; 4° C. water and additional temperatures as needed will be added; this is simply another circulating water bath and three full scale COTS valves and solenoids. Engineering calculations, studies, and experiments can determine effects of surface-to-volume ratios and the depth (mm) of reaction tolerated by the demands of cycling uniformity to define optimal geometry for the reactors, i.e., long thick tubes, oval tubing, or parallel plates, and validated with scientific experiments defining performance. Separation of those beads carrying amplicons from null beads can occur in the BeadStorm module, as a final step before SuperPyroSequencing or other analysis methods. Hardware to implement devices can be integrated under software control.

For example, a single microchip Ligation Module and the single channel emPCR Module can be used to process human cell line libraries in a non-integrated workflow. Control processing can be performed manually with GS20 reagents and procedures.

In another embodiment the NanoBioPrepSPS can be scaled-up and the Ligation Module and emPCR Module fully integrated. A full 42 microchip Ligation Module can be built by means well known to one skilled in the art. For example (1) a tower can be fabricated to hold the microchips, (2) build the Microchip Controller which will operate the latching MOV valves, pumps, and routers, (3) the NanoBioPrep robotic platform and the first 42 microchips can be microfabricated and tested, and (4) the 42 microchip Ligation Module can be integrated and tested. In parallel, the BeadStorm design can be evolved to process the pooled samples. The emPCR Module can be expanded to hold 9 runs from a Ligation Module. The emPCR performance can be optimized using both the 454 GS20 and SuperPyroSequencing. The 42 microchip Ligation Module can be plumbed to the fully expanded emPCR module and the process optimized, based on the one microchip-one channel device already developed. With the NanoBioPrepSPS as described, a 10% of a complete human genome can be done or a complete human de novo sequencing.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
   a) providing a microfluidic device comprising:
      i) at least one microfluidic circuit, wherein the at least one microfluidic circuit comprises:
         (A) a first microfluidic channel;
         (B) a first port;
         (C) a second port;
         (D) a first valve, wherein the first valve has a first position and a second position in which the cross-sectional area of the first valve is increased;
         (E) a second channel that converges with the first channel at a nexus, wherein the nexus comprises a valve that, when open, allows for fluid communication between said first and second channels and, when closed, interrupts fluid flow between the first and second channels but not along the first channel, and wherein the second channel is fluidically connected to a third port;
         (F) a reactor; and
         (G) at least one diaphragm pump comprising at least three diaphragm valves configured to pump fluid from the first port and the third port into the first valve, into the reactor and into the second port; and ii) a magnet configured to produce a magnetic field within the first valve;

b) pumping reagent from the first port and sample from the third port into the first channel to form a mixture;

c) pumping the mixture into the reactor and performing a chemical or biochemical reaction on the mixture to create a product;

d) contacting the product in the device with particles, wherein the particles bind the product;

e) positioning the first valve in the second position;

f) moving the particles through the first channel into the first valve; and g) capturing the particles in the first valve with the magnetic field.

2. The method of claim 1, further comprising:

h) washing the particles.

3. The method of claim 2, further comprising:

i) collecting the product.

4. The method of claim 1, wherein the chemical or biochemical reaction comprises PCR, cycle sequencing, isothermal nucleic acid amplification, ligation, restriction, second strand synthesis, transcription, translation, DNA modification, polymerization, DNA-protein binding, addition, cleavage, cyclization or condensation.

5. The method of claim 1, further comprising varying the temperature in the reactor while performing the reaction in the reactor.

6. A microfluidic device comprising:

i) at least one microfluidic circuit, wherein the at least one microfluidic circuit comprises:

(A) a first microfluidic channel;

(B) a first port;

(C) a second port;

(D) a first valve, wherein the first valve has a first position and a second position in which the cross-sectional area of the first valve is increased;

(E) a second channel that converges with the first channel at a nexus, wherein the nexus comprises a valve that, when open, allows for fluid communication between said first and second channels and, when closed, interrupts fluid flow between the first and second channels but not along the first channel, and wherein the second channel is fluidically connected to a third port;

(F) a reactor; and (G) at least one diaphragm pump comprising at least three diaphragm valves configured to pump fluid from the first port and the third port into the first valve, into the reactor and into the second port;

ii) a magnet configured to produce a magnetic field within the first valve; and iii) particles, wherein the particles are configured to move through the first channel into the first valve and to be captured in the first valve by the magnetic field when the first valve is in the second position.

7. The device of claim 6, which is configured to:

a) pump reagent from the first port and sample from the third port into the first channel to form a mixture;

b) pump the mixture into the reactor and perform a chemical or biochemical reaction on the mixture to create a product;

c) contact the product in the device with the particles, wherein the particles bind the product;

d) position the first valve in the second position;

e) move the particles through the first channel into the first valve; and f) capture the particles in the first valve with the magnetic field.

8. The device of claim 7, which is further configured to:

g) wash the particles.

9. The device of claim 8, which is further configured to:

h) collect the product.

10. The device of claim 7, wherein the chemical or biochemical reaction comprises PCR, cycle sequencing, isothermal nucleic acid amplification, ligation, restriction, second strand synthesis, transcription, translation, DNA modification, polymerization, DNA-protein binding, addition, cleavage, cyclization or condensation.

11. The device of claim 7, wherein the temperature in the reactor is varied while the reaction is performed in the reactor.

* * * * *